US012558325B2

(12) United States Patent
Ford et al.

(10) Patent No.: US 12,558,325 B2
(45) **Date of Patent: *Feb. 24, 2026**

(54) METHODS FOR IMPROVING NEUROLOGICAL DISEASES AND DISORDERS

(71) Applicant: CuraSen Therapeutics, Inc., San Carlos, CA (US)

(72) Inventors: Anthony P. Ford, San Carlos, CA (US); Gabriel Vargas, San Carlos, CA (US)

(73) Assignee: CuraSen Therapeutics, Inc., San Carlos, CA (US)

( * ) Notice: Subject to any disclaimer, the term of this patent is extended or adjusted under 35 U.S.C. 154(b) by 273 days.

This patent is subject to a terminal disclaimer.

(21) Appl. No.: 18/107,886

(22) Filed: Feb. 9, 2023

(65) Prior Publication Data

US 2023/0181492 A1 Jun. 15, 2023

Related U.S. Application Data

(63) Continuation of application No. 17/125,741, filed on Dec. 17, 2020, now Pat. No. 11,607,395.

(60) Provisional application No. 63/034,364, filed on Jun. 3, 2020, provisional application No. 62/950,077, filed on Dec. 18, 2019.

(51) Int. Cl.

| | |
|---|---|
| ***A61K 31/136*** | (2006.01) |
| ***A61K 31/138*** | (2006.01) |
| ***A61P 25/16*** | (2006.01) |
| ***A61P 25/24*** | (2006.01) |
| ***A61P 25/28*** | (2006.01) |

(52) U.S. Cl.

CPC .......... *A61K 31/136* (2013.01); *A61K 31/138* (2013.01); *A61P 25/16* (2018.01); *A61P 25/24* (2018.01); *A61P 25/28* (2018.01)

(58) Field of Classification Search

CPC ..... A61K 31/136; A61K 31/138; A61P 25/16; A61P 25/24; A61P 25/28

See application file for complete search history.

(56) References Cited

U.S. PATENT DOCUMENTS

| | | | | |
|---|---|---|---|---|
| 5,552,442 | A | 9/1996 | Maltin | |
| 7,135,497 | B1 | 11/2006 | Zeman et al. | |
| 7,528,175 | B2 | 5/2009 | Bond | |
| 8,026,073 | B2 | 9/2011 | Pei | |
| 9,320,724 | B2 | 4/2016 | Salehi et al. | |
| 9,539,221 | B2 | 1/2017 | Bond | |
| 10,259,877 | B2 | 4/2019 | Sun | |
| 10,328,082 | B2 | 6/2019 | Chekler | |
| 10,947,196 | B2 | 3/2021 | Ford et al. | |
| 11,607,395 | B2 * | 3/2023 | Ford | A61K 31/138 |
| 2004/0034087 | A1 | 2/2004 | Kilian et al. | |
| 2007/0021421 | A1 | 1/2007 | Hampton | |
| 2008/0033027 | A1 | 2/2008 | Bascomb et al. | |
| 2010/0216805 | A1 | 8/2010 | Barlow et al. | |
| 2010/0240764 | A1 | 9/2010 | Greb et al. | |
| 2011/0046090 | A1 | 2/2011 | Barlow et al. | |
| 2012/0263764 | A1 | 10/2012 | Watson | |
| 2013/0096126 | A1 | 4/2013 | Shamloo et al. | |
| 2013/0116215 | A1 | 5/2013 | Coma et al. | |
| 2014/0235726 | A1 | 8/2014 | Salehi et al. | |
| 2014/0256822 | A1 | 9/2014 | McCarty | |
| 2015/0011630 | A1 | 1/2015 | Goldstein et al. | |
| 2015/0080703 | A1 | 3/2015 | Reiman | |
| 2016/0184241 | A1 | 6/2016 | Salehi et al. | |
| 2016/0184315 | A1 | 6/2016 | Shamloo et al. | |
| 2016/0311913 | A1 | 10/2016 | Sun | |
| 2016/0324862 | A1 | 11/2016 | Tagliati et al. | |
| 2018/0030744 | A1 | 2/2018 | Apostolopoulos | |
| 2018/0311240 | A1 | 11/2018 | Broka | |
| 2019/0256607 | A1 | 8/2019 | Sun | |
| 2019/0358204 | A1 | 11/2019 | Bristow et al. | |
| 2020/0108065 | A1 | 4/2020 | Ford | |
| 2020/0237724 | A1 | 7/2020 | Shamloo et al. | |
| 2020/0308114 | A1 | 10/2020 | Ford | |
| 2020/0308115 | A1 | 10/2020 | Ford | |
| 2021/0121444 | A1 | 4/2021 | Ford | |
| 2021/0186897 | A1 | 6/2021 | Ford et al. | |
| 2023/0414588 | A1 * | 12/2023 | Ford | A61K 31/44 |

FOREIGN PATENT DOCUMENTS

| | | | |
|---|---|---|---|
| EP | 4161496 | A1 | 4/2023 |
| WO | WO 2004/009090 | A1 | 1/2004 |
| WO | WO 2006/108424 | | 10/2006 |
| WO | WO 2011/133226 | A2 | 10/2011 |
| WO | WO 2017/115873 | | 7/2017 |

(Continued)

OTHER PUBLICATIONS

EP Extended Search Report in European Application No. Dec. 22, 2023, 13 pages.

McNamee et al., "Noradrenaline acting at central @b-adrenoceptors induces interleukin-10 and suppressor of cytokine signaling-3 expression in rat brain: Implications for neurodegeneration", Brain, Behavior and Immunity, May 2010, 24(4):660-671.

PCT International Search Report and Written Opinion in International Application No. PCT/US2023/84572, dated Apr. 12, 2024, 18 pages.

Simon, "Experimental and clinical evidence of the antidepressant effect of a beta-adrenergic stimulant", Psychological Medicine, May 1978, 8:335-338.

EP Extended Search Report in European Application No. 20878218.5, dated Oct. 17, 2023, 8 pages.

Coutellier et al., "Beta 1-Adrenergic Receptor Activation Enhances Memory in Alzheimer's Disease Model," *Annals of Clinical and Translational Neurology* (May 2014), 1(5):348-360.

(Continued)

*Primary Examiner* — Sarah Pihonak

(74) *Attorney, Agent, or Firm* — DLA Piper LLP (US)

(57) ABSTRACT

In various aspects and embodiments provided are compositions and methods for identifying patients in need of improving cognition and/or treating a neurodegenerative disease in a patient and treating such patient. More specifically, the disclosure in some embodiments includes administration of a β-AR agonist and a peripherally acting β-blocker (PABRA) to a patient in need thereof.

23 Claims, 15 Drawing Sheets

(56) References Cited

FOREIGN PATENT DOCUMENTS

| | | | |
|---|---|---|---|
| WO | WO 2018/195473 | | 10/2018 |
| WO | WO 2019/241744 | A1 | 12/2019 |

OTHER PUBLICATIONS

Follesa and Mocchetti, "Regulation of Basic Fibroblast Growth Factor and Nerve Growth Factor mRNA by Beta-Adrenergic Receptor Activation and Adrenal Steroids in Rat Central Nervous System," *Molecular Pharmacology* (Feb. 1993), 43(2):132-138.
Geyer and Frampton, "Peripheral Mediation of Effects of Clenbuterol on Locomotor and Investigatory Behavior in Rats," *Pharmacol. Biochem. Behav.* (Jun. 1998), 30(2):417-420.
Gliebus and Lippa, "The Influence of Beta-Blockers on Delayed Memory Function in People with Cognitive Impairment," *Am. J. Alzheimers Dis. Other Demen.* (2007), 22(1):57-61.
Mittal et al., "Beta2-Adrenoreceptor is a Regulator of the Alpha-Synuclein Gene Driving Risk of Parkinson's Disease," *Science* (2017) 357:891-898.
PCT International Search Report and Written Opinion in International Application No. PCT/US2020/065655, dated Mar. 8, 2021, 13 pages.
PCT International Search Report and Written Opinion in International Application No. PCT/US2019/037371, dated Sep. 11, 2019, 16 pages.
PCT International Search Report and Written Opinion in International Application No. PCT/US2019/037358, dated Sep. 23, 2019.
Ramos et al., "Beta2 Adrenergic Agonist, Clenbuterol, Enhances Working Memory Performance in Aging Animals," *Neurobiology of Aging* (2008) 29(7):1060-1069.
Snyder, Evan Y., "Finding a New Purpose for Old Drugs," *Science* (2017), 357(6354):869-870.
Uc et al., "Beta-Adrenergics Enhance Brain Extraction of Levodopa," *Mov. Disord.* (2002), 17(1):54-59.
Yoon, et al., "Rapid Screening of Blood-Brain Barrier Penetration of Drugs Using the Immobilized Artificial Membrane Phosphatidylcholine Column Chromatography," 2006, SLAS Discovery, 11, 2006, pp. 13-20.
Tartaglia, et al., "Differentiation between primary lateral sclerosis and amyotrophic lateral sclerosis: examination of symptoms and signs at disease onset and during follow-up," Arch Neurol, Feb. 2007, 64(2), Abstract only.
Wheeldon et al., "The effects of lower than conventional doses of oral nadolol on relative beta1/beta2-adrenoceptor blockade", Br J Clin Pharmac, 1994, 38, pp. 103-108.
Nomura et al., "Clinical significance of REM sleep behavior disorder in Parkinson's disease", 2013, Sleep Medicine, 14, pp. 131-135.
Ridler, "Asthma drug could protect against PD", Nature Reviews Neurology, 2017, 1 page.
Nathan, "Diabetes: Advances in Diagnosis and Treatment", JAMA, 2015, 314, pp. 1052-1062.
Bartus et al., "B2-Adrenoceptor agonists as novel, safe and potentially effective therapies for Amyotrophic lateral sclerosis (ALS)", Neurobiol Dis, Jan. 2016, 85: 11-24.
Gurney, "The use of transgenic mouse models of amyotrophic lateral sclerosis in preclinical drug studies", J Neurol Sci, Oct. 1997, 152(Suppl 1):S-67-73.
Kobayashi et al., "Effects of Early Albuterol (Salbutamol) Administration on the Development of posttraumatic Stress Symptoms", Psychiatry Research, 2011, 185(1-2): 296-298.
Wang et al., "Determination of the Competitive Adsorption Isotherms of Nadolol Enantiomers by an Improved h-Root Method", Industrial & Engineering Chemistry Research, 2003, 42(24): 6171-6180.
Lodeweyckx et al., "Safety, Tolerability and Cerebral Blood Flow After Single Doses of the Beta2-Agonist, Clenbuterol, In Patients with Mild Cognitive Impairment Or Parkinson's Disease", 2021, Journal of Prevention of Alzheimer's Disease, 8 (Suppl 1), S87-S88.
Teng et al., "Therapeutic effects of clenbuterol in a murine model of amyotrophic lateral sclerosis", Neuroscience Letters, Jan. 2006, 397(1-2):155-158.
Drugs.com, "Albuterol Dosage", first available 2010, Drugs.com (Year: 2010).
Drugs.com, "Albuterol Inhalation", first available 2010, Drugs.com (Year: 2010).
Chen et al., "Comorbidity and dementia: A nationwide survey in Taiwan", 2017, PLOS ONE, 12, pp. 1-12 (Year: 2017).
Drugs.com, "Nadolol Dosage", 2023, Drugs.com (Year: 2023).
Jessen et al., "Beta2-adrenergic agonist clenbuterol increases energy expenditure and fat oxidation, and induces mTOR phosphorylation in skeletal muscle of young healthy men", 2020, Drug Testing and Analysis, 12, pp. 610-618 (Year: 2020).
International Search Report and the Written Opinion for PCT/US2025/018417 mailed Jun. 6, 2025, 15 pages.
Extended European Search Report for EP21865003.4 mailed Aug. 26, 2024, 16 pages.
U.S. Office Action for U.S. Appl. No. 18/198,191 mailed Aug. 23, 2024, 52 pages.
International Search Report and Written Opinion for PCT/US2023/084629 mailed Apr. 12, 2024, 14 pages.
International Search Report and Written Opinion for PCT/US2023/022422 mailed Aug. 16, 2023, 20 pages.

* cited by examiner

β₂-AR Agonists Clenbuterol and Salbutamol Improve Delayed Word Recall in the Visual Verbal Learning Test: Mean Change from Placebo in Number of Correct Words Recalled Data are plotted as mean (± standard error) from all available data (N=17).

METHODS FOR IMPROVING NEUROLOGICAL DISEASES AND DISORDERS

CROSS-REFERENCE TO RELATED APPLICATIONS

This application is a continuation application of U.S. application Ser. No. 17/125,741 filed Dec. 17, 2020; which claims the benefit under 35 USC § 119(e) to U.S. Application Ser. No. 63/034,364 filed Jun. 3, 2020 and to U.S. Application Ser. No. 62/950,077 filed Dec. 18, 2019. The disclosure of each of the prior applications is considered part of and is incorporated by reference in the disclosure of this application.

FIELD OF THE INVENTION

The present disclosure relates generally to compositions and methods for improving cognition and/or treating a neurodegenerative disease in a patient.

BACKGROUND

United States Patent Application Publication Number 20130096126 discloses "a method for enhancing learning or memory of both in a mammal having impaired learning or memory or both from a neuro-degenerative disorder, which entails the step of administering at least one compound or a salt thereof which is a $\beta_1$-ARenergic receptor agonist, partial agonist or receptor ligand in an amount effective to improve the learning or memory or both of said mammal."

United States Patent Application Publication Number 20140235726 discloses "a method of improving cognition in a patient with Down syndrome, which entails administering one or more $\beta_2$ adrenergic receptor agonists to the patient in an amount and with a frequency effective to improve cognition of the patient as measured by contextual learning tests."

United States Patent Application Publication Number 20160184241 discloses "a method of improving cognition in a patient with Down syndrome, which entails intranasally administering one or more $\beta_2$-AR agonists or pharmaceutically-acceptable salts of either or both to the patient in an amount and with a frequency effective to improve cognition of the patient as measured contextual learning tests."

PCT Application Publication Number WO2017115873 discloses "a combination of two or more compounds selected from the group consisting of compounds represented by the Compound No. 1-130, a preventive or therapeutic agent for Alzheimer's disease (AD)" and states "In an attempt to achieve the aforementioned object, the present inventors have screened an existing drug library consisting of 1280 kinds of pharmaceutical compounds approved by the Food and Drug Administration (FDA) in America by using nerve cells induced to differentiate from iPS cells derived from AD patients, and extracted 129 kinds (including one kind of concomitant drug) of compounds that improve Aβ pathology in the nerve cells as candidate therapeutic drugs for AD."

PCT Application Publication Number WO2006108424 states "[t]he invention furthermore relates to dermatological compositions without skin sensitization properties and which contain an enantiomerically pure enantiomer of a $\beta_2$ adrenoceptor agonist.

PCT Application Publication Number WO2018195473 provides "methods of treating a subject who has a synucleinopathy (e.g., Parkinson's disease) that include administering to a subject in need of such treatment therapeutically effective amounts of a $\beta_2$-adrenoreceptor agonist and at least one therapeutic agent."

SUMMARY OF THE INVENTION

In one aspect, a method for improving cognitive function and/or treating a neurodegenerative disease is provided wherein the method includes administering a therapeutically effective amount of β-AR agonist and a sub-therapeutic dose of a peripherally acting β-blocker (PABRA) to a patient. In one embodiment, a method for improving cognitive function and/or treating a neurodegenerative disease is provided wherein the method includes administering a therapeutically effective amount of $\beta_2$-AR agonist and a sub-therapeutic dose of a peripherally acting β-blocker (PABRA) to a patient. In one embodiment, a method for improving cognitive function and/or treating a neurodegenerative disease is provided wherein the method includes administering a therapeutically effective amount of $\beta_1$-AR agonist and a sub-therapeutic dose of a peripherally acting β-blocker (PABRA) to a patient.

In some embodiments of the methods and compositions provided herein, the purpose of the PABRA is not to directly treat a specific disease indication or condition, but rather to offset undesirable peripheral side effects of the β-AR agonist (e.g., the PABRA may be administered to reduce, restrict, or counter any adverse effect(s) of the β-AR agonist, such as cardiac effects or performance-enhancing effects, thus, reducing the likelihood of abuse), and therefore in some embodiments, the PABRA dose may be lower than that generally used in previously approved therapeutic situations and indications where the PABRA is intended to directly treat a specific disease. As used herein, the term "sub-therapeutic dose" means a dose of an agent that is less than the minimum dose that is independently effective to treat a specific disease indication. In some embodiments, a sub-therapeutic dose is less than the lowest dose for which an agent is independently approved to treat any specific disease indication by a regulatory agency. In some embodiments, a sub-therapeutic dose is less than the lowest dose for which an agent is approved to treat any specific disease indication by the United States FDA. In some embodiments, a sub-therapeutic dose is less than the lowest dose for which an agent is approved to treat any specific disease indication by a regulatory agency (such as the US FDA). In certain embodiments, a subtherapeutic dose of a PABRA is sufficient to off-set or counter one or more undesirable side effects of a β-AR agonist, but the dose is less than what would generally be administered to independently treat a disease or disorder. For example, in some embodiments a sub-therapeutic dose may be 90% or less; or 85% or less; or 80% or less; or 75% or less; or 70% or less; or 65% or less; or 60% or less; or 55% or less; or 50% or less; or 45% or less; or 40% or less; or 35% or less; or 30% or less; or 25% or less; or 20% or less; or 15% or less; or 10% or less; or 5% or less; or 4% or less; or 3% or less; or 2.5% or less; or 2% or less; or 1.5% or less; or 1% or less; or 0.5% or less as compared to a dose that the agent is effective for, or approved for treating a specific disease indication. In certain embodiments, a sub-therapeutic dose for a PABRA may be about 90%; or about 85%; or about 80%; or about 75%; or about 70%; or 6 about 5%; or about 60%; or about 55%; or about 50%; or about 45%; or about 40%; or about 35%; or about 30%; or 25%; or about 20%; or about 15%; or about 10% or less; about 5%; or about 4%; or about 3%; or about 2.5%; or about 2%; or about 1.5% or less; or about 1%; or about 0.5% as compared to a dose that the agent is effective for, or approved for, treating a specific disease indication. For example, the PABRA nadolol at a dose of 40 mg once daily is approved in the United States for treatment of hypertension and angina pectoris, therefore a sub-therapeutic dose of nadolol in certain embodiments would be a dose that is less than 40 mg daily; for example a sub-therapeutic dose of nadolol may be 90% or less; or 85% or less; or 80% or less; or 75% or less; or 70% or less; or 65% or less; or 60% or less; or 55% or less; or 50% or less; or 45% or less; or 40% or less; or 35% or less; or 30% or less; or 25% or less; or 20% or less; or 15% or less; or 10% or less; or 5% or less; or 4% or less; or 3% or less; or 2.5% or less; or 2% or less; or 1.5% or less; or 1% or less; or 0.5% or less as compared to the 40 mg daily dose; or in some embodiments a sub-therapeutic dose of nadolol may be about 90%; or about 85%; or about 80%; or about 75%; or about 70%; or 6 about 5%; or about 60%; or about 55%; or about 50%; or about 45%; or about 40%; or about 35%; or about 30%; or 25%; or about 20%; or about 15%; or about 10% or less; about 5%; or about 4%; or about 3%; or about 2.5%; or about 2%; or about 1.5% or less; or about 1%; or about 0.5% of a 40 mg daily dose. In some embodiments, the peripherally acting β-blocker (PABRA) is nadolol and is administered in a total daily dose of about 0.01 to 15 mg, 0.1 to 15 mg, 0.1 to 10 mg, 0.1 to 1 mg, 0.1 to 0.5 mg, 0.2 to 0.3 mg, 0.23 to 0.27 mg; 0.1 to 5 mg, 1 to 15 mg, 1 to 10 mg, 1 to 5 mg, 5 to 10 mg, 10 mg or less, 7 mg or less, 5 mg or less, 1 mg or less, about 0.01 mg, about 0.05 mg; about 0.1 mg, about 0.2 mg, about 0.25 mg, about 0.3 mg, about 0.4 mg, about 0.5 mg, about 1 mg, about 2 mg, about 3 mg, about 4 mg, about 5 mg, about 6 mg, about 7 mg, about 8 mg, about 9 mg, or about 10 mg. In some embodiments the aforementioned doses of nadolol are weekly doses, or are twice-weekly doses. Another example of a PABRA that could be used in the methods described herein is Atenolol. Atenolol approved for various indications including hypertension, angina pectoris prophylaxis, angina pectoris, and myocardial infarction at doses ranging from 25-200 mg once daily. Accordingly, a sub-therapeutic dose of atenolol in certain embodiments would be a dose that is less than 25 mg daily; for example a sub-therapeutic dose of atenolol may be 90% or less; or 85% or less; or 80% or less; or 75% or less; or 70% or less; or 65% or less; or 60% or less; or 55% or less; or 50% or less; or 45% or less; or 40% or less; or 35% or less; or 30% or less; or 25% or less; or 20% or less; or 15% or less; or 10% or less; or 5% or less; or 4% or less; or 3% or less; or 2.5% or less; or 2% or less; or 1.5% or less; or 1% or less; or 0.5% or less as compared to a 25 mg daily dose; or in some embodiments a sub-therapeutic dose of atenolol may be about 90%; or about 85%; or about 80%; or about 75%; or about 70%; or 6 about 5%; or about 60%; or about 55%; or about 50%; or about 45%; or about 40%; or about 35%; or about 30%; or 25%; or about 20%; or about 15%; or about 10% or less; about 5%; or about 4%; or about 3%; or about 2.5%; or about 2%; or about 1.5% or less; or about 1%; or about 0.5% of a 25 mg daily dose. In some embodiments, the peripherally acting β-blocker (PABRA) is atenolol and is administered in a dose of about 0.01 to 15 mg, 0.1 to 15 mg, 0.1 to 10 mg, 0.1 to 1 mg, 0.1 to 0.5 mg, 0.2 to 0.3 mg, 0.23 to 0.27 mg; 0.1 to 5 mg, 1 to 15 mg, 1 to 10 mg, 1 to 5 mg, 5 to 10 mg, 10 mg or less, 7 mg or less, 5 mg or less, 1 mg or less, about 0.01 mg, about 0.05 mg; about 0.1 mg, about 0.2 mg, about 0.25 mg, about 0.3 mg, about 0.4 mg, about 0.5 mg, about 1 mg, about 2 mg, about 3 mg, about 4 mg, about 5 mg, about 6 mg, about 7 mg, about 8 mg, about 9 mg, or about 10 mg. In some embodiments the aforementioned doses of atenolol are weekly doses or are twice-weekly doses.

In certain embodiments, a PABRA as used herein may have relatively limited CNS (blood-brain barrier) penetration and thus be preferentially active in the periphery.

In certain embodiments of the methods and compositions disclosed herein, the β-AR agonist is administered in a dose that is therapeutically effective in improving cognition and/or treating a neurodegenerative disease in a patient. In some embodiments, the β-AR agonist can be administered at a dose of from about 30 to 160 μg. In some embodiments, the β-AR agonist can be administered at a dose of from about 50 to 160 μg. For some embodiments, the β-AR agonist can be administered at a dose of from about 1 to 300 μg, 5 to 200 μg, 10 to 180 μg, 10 to 40 μg, 20 to 50 μg, 40 to 80 μg, 50 to 100 μg, 100 to 200 μg, 30 to 160 μg, 50 to 160 μg, 80 to 160 μg, 100 to 160 μg, 120 to 160 μg, 140 to 160 μg, 150 to 170 μg, 30 to 140 μg, 50 to 140 μg, 80 to 140 μg, 100 to 140 μg, 120 to 140 μg, 30 to 120 μg, 50 to 120 μg, 80 to 120 μg, 100 to 120 μg, 30 to 100 μg, 50 to 100 μg, 80 to 100 μg, 30 to 80 μg, 50 to 80 μg, 30 to 50 μg, about 10 μg, about 20 μg, about 25 μg, about 30 μg, about 40 μg, about 50 μg, about 60 μg, about 70 μg, about 80 μg, about 90 μg, about 100 μg, about 110 μg, about 120 μg, about 125 μg, about 130 μg, about 140 μg, about 150 μg, or about 160 μg, about 170 μg, about 175 μg, about 180 μg, about 190 μg, about or 200 μg. In some embodiments, the β-AR agonist can be administered in a dose from 150 μg to 1 mg; or from 200 μg to 500 μg, or about 250 μg, or about 300 μg, or about 400 μg, or about 500 μg. In some embodiments, the β-AR agonist can be administered in a dose from 0.5-20 mg; or 1-10 mg; or 2-8 mg; or about 1 mg; or about 2 mg; or about 3 mg; or about 4 mg, or about 5 mg; or about 6 mg; or about 7 mg; or about 8 mg; or about 10 mg. In some embodiments of the aspects or embodiments provided herein the β-AR agonist is clenbuterol and the dose is 1 to 300 μg, 5 to 200 μg, 10 to 180 μg, 10 to 40 μg, 20 to 50 μg, 40 to 80 μg, 50 to 100 μg, 100 to 200 μg, 30 to 160 μg, 50 to 160 μg, 80 to 160 μg, 100 to 160 μg, 120 to 160 μg, 140 to 160 μg, 150 to 170 μg, 30 to 140 μg, 50 to 140 μg, 80 to 140 μg, 100 to 140 μg, 120 to 140 μg, 30 to 120 μg, 50 to 120 μg, 80 to 120 μg, 100 to 120 μg, 30 to 100 μg, 50 to 100 μg, 80 to 100 μg, 30 to 80 μg, 50 to 80 μg, 30 to 50 μg, about 10 μg, about 20 μg, about 25 μg, about 30 μg, about 40 μg, about 50 μg, about 60 μg, about 70 μg, about 80 μg, about 90 μg, about 100 μg, about 110 μg, about 120 μg, about 125 μg, about 130 μg, about 140 μg, about 150 μg, or about 160 μg, about 170 μg, about 175 μg, about 180 μg, about 190 μg, or about 200 μg. In some embodiments of the aspects or embodiments provided herein the β-AR agonist is tulobuterol and the dose is from 0.5-20 mg; or 1-10 mg; or 2-8 mg; or about 1 mg; or about 2 mg; or about 3 mg; or about 4 mg; or about 5 mg; or about 6 mg; or about 7 mg; or about 8 mg; or about 10 mg. In some embodiments the aforementioned doses are daily doses, twice daily doses, weekly doses, or twice-weekly doses.

For some embodiments the doses of any agent provided herein can be a total daily dose. In some embodiments the total daily dose as provided herein is achieved by dosing once daily, in some embodiments the total daily dose is achieved by dosing twice daily, and in yet other embodiments the total daily dose is achieved by dosing more than two times daily. In certain embodiments, the doses of any agent provided herein can be a dose administered weekly or twice weekly. For some embodiments, the therapeutically effective amount of β-AR agonist and the sub-therapeutic dose of the peripherally acting β-blocker (PABRA) are administered for a period of weeks or more; or three weeks or more; or five weeks or more; or ten weeks or more; or twenty weeks or more; or a year or more.

In one aspect, a method for improving cognitive function and/or treating a neurodegenerative disease is provided wherein the method includes administering a therapeutically effective amount of β-AR agonist and a peripherally acting β-blocker (PABRA) to a patient, wherein the peripherally acting β-blocker (PABRA) is administered in a dose of about 15 mg or less. In some embodiments, the peripherally acting β-blocker (PABRA; such as nadolol or atenolol) is administered in a dose of about 0.01 to 15 mg, 0.1 to 15 mg, 0.1 to 10 mg, 0.1 to 1 mg, 0.1 to 0.5 mg, 0.2 to 0.3 mg, 0.23 to 0.27 mg; 0.1 to 5 mg, 1 to 15 mg, 1 to 10 mg, 1 to 5 mg, 5 to 10 mg, 10 mg or less, 7 mg or less, 5 mg or less, 1 mg or less, about 0.01 mg, about 0.05 mg; about 0.1 mg, about 0.2 mg, about 0.25 mg, about 0.3 mg, about 0.4 mg, about 0.5 mg, about 1 mg, about 2 mg, about 3 mg, about 4 mg, about 5 mg, about 6 mg, about 7 mg, about 8 mg, about 9 mg, or about 10 mg. For some embodiments where it is not indicated differently, the above-mentioned doses are a total daily dose. For some, the above-mentioned doses are a total weekly dose. For some embodiments, the therapeutically effective amount of β-AR agonist and the dose of the peripherally acting β-blocker (PABRA) are administered for a period of weeks or more.

The methods provided herein may further include subjecting the patient to brain imaging to determine regional metabolic activation and/or cerebral perfusion in cerebrocortical, forebrain, midbrain and brainstem areas and/or to identify whether said patient is in need of or desiring improvement of cognitive function and/or treatment of a neurodegenerative disease. In some embodiments, the brain imaging is fluorodeoxyglucose positron emission tomography (FDG-PET), used alone or in combination with other imaging approaches such as magnetic resonance imaging (MRI) and CT. In some embodiments, the brain imaging is, or can include, magnetic resonance imaging-arterial spin labeling (MRI-ASL), or magnetic resonance imaging-blood oxygenation level dependent computerized tomography (MRI-BOLD). In some embodiments the brain imaging may include MRI-ASL used to monitor cerebral blood flow, including, for example, cerebral blood flow to the hippocampus or thalamus. In some embodiments, of the aspects and embodiments disclosed herein, "improving cognition and/or treating a neurodegenerative disease" in a patient may include improving cognitive and executive function, improving inflammatory status in cerebral or cerebrospinal fluid (CSF) samples, attenuating proteinopathy burden (for example, based on imaging or CSF sampling) and/or improving regional cerebral metabolic status (reversing hypometabolism) or perfusion in the patient. In certain embodiments of the methods and compositions disclosed herein the β-AR agonist is administered in a dose that is therapeutically effective in improving cognition and/or treating a neurodegenerative disease in a patient. As such, in certain embodiments, "identifying a patient in need of or desiring improvement of cognitive function and/or treatment of a neurodegenerative disease" may include identifying a patient in need of or desiring improvement of cognitive and executive function, improvement of inflammatory status in cerebral or CSF samples, attenuation of proteinopathy burden (for example, based on imaging or CSF sampling) and/or improvement of regional cerebral metabolic/perfusion status (reversing hypometabolism or hypoperfusion). In another aspect, a method is provided wherein the method includes subjecting a patient to brain imaging to determine regional metabolic activation or perfusion in cerebrocortical, forebrain, midbrain and brainstem areas and/or to identify whether said patient is in need of or desiring improvement of cognitive function and/or treatment of a neurodegenerative disease, and administering to said patient a β-AR agonist and a peripherally acting β-blocker (PABRA) to improve cognition and/or treat a neurodegenerative disease in said patient, wherein the peripherally acting β-blocker (PABRA) is administered in a dose of about 15 mg or less. In a similar aspect, a method is provided wherein the method includes subjecting a patient to brain imaging to determine regional metabolic or perfusion activation in cerebrocortical, forebrain, midbrain and brainstem areas and/or to identify whether said patient is in need of or desiring improvement of cognitive function and/or treatment of a neurodegenerative disease, and administering to said patient a β-AR agonist and a peripherally acting β-blocker (PABRA) to improve cognition and/or treat a neurodegenerative disease in said patient, wherein the peripherally acting β-blocker (PABRA) is administered in a sub-therapeutic dose.

The method can further include subsequently re-subjecting said patient to brain imaging to determine any improvement in regional metabolic activation in cerebrocortical, forebrain, midbrain and brainstem areas, cognitive function and/or treatment of said neurodegenerative disease. In some embodiments, the brain imaging is FDG-PET, used alone or in combination with other imaging approaches such as MRI and CT. In some embodiments, the brain imaging is, or can include, MRI-ASL or MRI-BOLD.

In yet another aspect, a method is provided wherein the method includes subjecting a patient to brain imaging to determine regional metabolic activation in forebrain, midbrain and brainstem areas, and administering to said patient a β-AR agonist and a peripherally acting β-blocker (PABRA), wherein the peripherally acting β-blocker (PABRA) is administered in a dose of about 15 mg or less. In a related aspect, a method is provided wherein the method includes subjecting a patient to brain imaging to determine regional metabolic activation in forebrain, midbrain and brainstem areas, and administering to said patient a β-AR agonist and a peripherally acting β-blocker (PABRA), wherein the peripherally acting β-blocker (PABRA) is administered in a sub-therapeutic dose. The method can further include subsequently re-subjecting said patient to brain imaging to determine any improvement in regional metabolic or perfusion activation in cerebrocortical, limbic, forebrain, midbrain and brainstem areas, cognitive function. In some embodiments, the brain imaging is FDG-PET, used alone or in combination with other imaging approaches such as MRI and CT. In some embodiments, the brain imaging is, or can include, MRI-ASL or MRI-BOLD. In some embodiments the brain imaging may include MRI-ASL used to monitor cerebral blood flow, including, for example, cerebral blood flow to the hippocampus; and an improvement of cerebral blood flow (for example to the hippocampus) in the subsequent MRI-ASL is indicative of effective action of the of β-AR agonist and/or improved cognition in the patient.

In some embodiments, a detectable label is provided, which can generate a spatial pattern of the brain imaging result. In some embodiments, 2-[$^{18}$F]fluoro-2-deoxy-D-glucose ($^{18}$FDG) can be used for FDG-PET, which can provide characteristic spatial patterns of brain metabolism and can help clinicians to make a reasonably accurate and early diagnosis for appropriate management or prognosis.

In some embodiments a detectable label on blood water molecules is produced by magnetic RF treatment of blood in the neck, which can generate a spatial pattern of the brains perfusion as an imaging result. In some such embodiments, MRI-ASL is used, which can provide characteristic spatial patterns of brain perfusion and can help clinicians to make a reasonably accurate and early diagnosis for appropriate management or prognosis.

In some aspects, a method for improving cognitive function and/or treating a neurodegenerative disease is provided wherein the method includes administering to said patient a β-AR agonist and a peripherally acting β-blocker (PABRA) to improve cognition and/or treat a neurodegenerative disease in said patient, wherein the peripherally acting β-blocker (PABRA) is administered in a dose of about 15 mg or less. In some related aspects, a method for improving cognitive function and/or treating a neurodegenerative disease is provided wherein the method includes administering to said patient a β-AR agonist and a peripherally acting β-blocker (PABRA) to improve cognition and/or treat a neurodegenerative disease in said patient, wherein the peripherally acting β-blocker (PABRA) is administered in a sub-therapeutic dose.

The method in some embodiments may further include subjecting a patient to brain imaging to determine regional metabolic activation in forebrain, midbrain and brainstem areas and/or to identify whether said patient is in need of or desiring improvement of cognitive function and/or treatment of a neurodegenerative disease. In some embodiments, the brain imaging is fluorodeoxyglucose positron emission tomography (FDG-PET), used alone or in combination with other imaging approaches such as magnetic resonance imaging (MRI) and CT. In some embodiments, the brain imaging is, or can include, MRI-ASL or MRI-BOLD. In some embodiments of the aspects and embodiments disclosed herein, "improving cognition and/or treating a neurodegenerative disease" in a patient may include improving cognitive and executive function, improving inflammatory status in cerebral or cerebrospinal fluid (CSF) samples, attenuating proteinopathies burden (for example, based on imaging or CSF sampling) and/or improving regional cerebral metabolic status (reversing hypometabolism) in the patient. Likewise, in certain embodiments, "identifying a patient in need of or desiring improvement of cognitive function and/or treatment of a neurodegenerative disease" may include identifying a patient in need of or desiring improvement of cognitive and executive function, improvement of inflammatory status in cerebral or CSF samples, attenuation of proteinopathies burden (for example, based on imaging or CSF sampling) and/or improvement of regional cerebral metabolic status (reversing hypometabolism). In another aspect, a method is provided wherein the method includes subjecting a patient to brain imaging to determine regional metabolic activation in forebrain, midbrain and brainstem areas and/or to identify whether said patient is in need of or desiring improvement of cognitive function and/or treatment of a neurodegenerative disease, and administering to said patient a βAR agonist and a peripherally acting β-blocker (PABRA) to improve cognition and/or treat a neurodegenerative disease in said patient, wherein the peripherally acting β-blocker (PABRA) is administered in a dose of about 15 mg or less. In a related aspect, a method is provided wherein the method includes subjecting a patient to brain imaging to determine regional metabolic activation in forebrain, midbrain and brainstem areas and/or to identify whether said patient is in need of or desiring improvement of cognitive function and/or treatment of a neurodegenerative disease, and administering to said patient a β-AR agonist and a peripherally acting β-blocker (PABRA) to improve cognition and/or treat a neurodegenerative disease in said patient, wherein the peripherally acting β-blocker (PABRA) is administered in a sub-therapeutic dose. ARFor some embodiments, the peripherally acting β-blocker (PABRA) is administered to reduce, restrict, or counter any adverse effects of the β-AR agonist, e.g., performance-enhancing effects, and reduces the likelihood of abuse.

The method can further include subsequently re-subjecting said patient to brain imaging to determine any improvement in regional metabolic or perfusion activation in cerebrocortical, forebrain, midbrain and brainstem areas, cognitive function and/or treatment of said neurodegenerative disease. In some embodiments, the brain imaging is FDG-PET, used alone or in combination with other imaging approaches such as MRI and CT. In some embodiments, the brain imaging is, or can include, MRI-ASL or MRI-BOLD. In yet another aspect, a method is provided wherein the method includes subjecting a patient to brain imaging determine regional metabolic activation in forebrain, midbrain and brainstem areas; administering to said patient a β-AR agonist and a peripherally acting β-blocker (PABRA); and subsequently re-subjecting said patient to brain imaging to determine any improvement in regional metabolic activation in forebrain, midbrain and brainstem areas, cognitive function. In some embodiments, the brain imaging is FDG-PET, used alone or in combination with other imaging approaches such as MRI and CT. In some embodiments, the brain imaging is, or can include, MRI-ASL or MRI-BOLD. In some embodiments, the patient does not have Alzheimer's disease. In some embodiments, the patient does not have Down Syndrome. In some embodiments, the patient does not have Parkinson's disease. In some embodiments, the patient does not have dementia with Lewy bodies.

In some embodiments, the β-AR agonist can be administered at a dose of from about 30 to 160 μg. In some embodiments, the β-AR agonist can be administered at a dose of from about 50 to 160 μg. For some embodiments, the β-AR agonist can be administered at a dose of from about 30 to 160 μg, 50 to 160 μg, 80 to 160 μg, 100 to 160 μg, 120 to 160 μg, 140 to 160 μg, 30 to 140 μg, 50 to 140 μg, 80 to 140 μg, 100 to 140 μg, 120 to 140 μg, 30 to 120 μg, 50 to 120 μg, 80 to 120 μg, 100 to 120 μg, 30 to 100 μg, 50 to 100 μg, 80 to 100 μg, 30 to 80 μg, 50 to 80 μg, 30 to 50 μg, 30 μg, 40 μg, 50 μg, 60 μg, 70 μg, 80 μg, 90 μg, 100 μg, 110 μg, 120 μg, 130 μg, 140 μg, 150 μg, or 160 μg. For some embodiments, the $\beta_2$-AR agonist can be administered at a dose of from 0.5-20 mg; or 1-10 mg; or 2-8 mg; or about 1 mg; or about 2 mg; or about 3 mg; or about 4 mg; or about 5 mg; or about 6 mg; or about 7 mg; or about 8 mg; or about 10 mg. For some embodiments, the above-mentioned doses are a total daily dose. For some embodiments, the above-mentioned doses are a total weekly dose. For some embodiments, the dose of β-AR agonist and the peripherally acting β-blocker (PABRA) are administered or weekly for a period of weeks or more.

In one aspect, a method for improving cognitive function and/or treating a neurodegenerative disease is provided wherein the method includes administering to said patient clenbuterol and nadolol to improve cognition and/or treat a neurodegenerative disease in said patient, wherein nadolol is administered in a dose of about 15 mg or less. In one aspect, a method for improving cognitive function and/or treating a neurodegenerative disease is provided wherein the method includes administering to said patient clenbuterol and nadolol to improve cognition and/or treat a neurodegenerative disease in said patient, wherein nadolol is administered in a sub-therapeutic dose. The method can further include subjecting a patient to brain imaging to determine regional metabolic activation in forebrain, midbrain and brainstem areas and/or to identify whether said patient is in need of or desiring improvement of cognitive function and/or treatment of a neurodegenerative disease.

For some embodiments, nadolol is a mixture of four diastereomers. For some embodiments, the nadolol administered is a specific enantiomerically pure isomer.

In some embodiments, the brain imaging is fluorodeoxyglucose positron emission tomography (FDG-PET), used alone or in combination with other imaging approaches such as magnetic resonance imaging (MRI) and CT. In some embodiments, the brain imaging is, or can include, MRI-ASL or MRI-BOLD. In some embodiments of the aspects and embodiments disclosed herein, "improving cognition and/or treating a neurodegenerative disease" in a patient may include improving cognitive and executive function, improving inflammatory status in cerebral or cerebrospinal fluid (CSF) samples, attenuating proteinopathies burden (for example, based on imaging or CSF sampling) and/or improving regional cerebral metabolic status (reversing hypometabolism) in the patient. Likewise, in certain embodiments, "identifying a patient in need of or desiring improvement of cognitive function and/or treatment of a neurodegenerative disease" may include identifying a patient in need of or desiring improvement of cognitive and executive function, improvement of inflammatory status in cerebral or CSF samples, attenuation of proteinopathies burden (for example, based on imaging or CSF sampling) and/or improvement of regional cerebral metabolic status (reversing hypometabolism). In another aspect, a method is provided wherein the method includes subjecting a patient to brain imaging to determine regional metabolic activation in forebrain, midbrain and brainstem areas and/or to identify whether said patient is in need of or desiring improvement of cognitive function and/or treatment of a neurodegenerative disease, and administering to said patient clenbuterol and nadolol to improve cognition and/or treat a neurodegenerative disease in said patient, wherein nadolol is administered in a dose of about 15 mg or less. In a related aspect, a method is provided wherein the method includes subjecting a patient to brain imaging to determine regional metabolic activation in forebrain, midbrain and brainstem areas and/or to identify whether said patient is in need of or desiring improvement of cognitive function and/or treatment of a neurodegenerative disease, and administering to said patient clenbuterol and nadolol to improve cognition and/or treat a neurodegenerative disease in said patient, wherein nadolol is administered in a sub-therapeutic dose.

For some embodiments, nadolol is a mixture of four diastereomers. For some embodiments, the nadolol administered is a specific enantiomerically pure isomer.

The method can further include subsequently re-subjecting said patient to brain imaging to determine any improvement in regional metabolic activation in forebrain, midbrain and brainstem areas, cognitive function and/or treatment of said neurodegenerative disease. In some embodiments, the brain imaging is FDG-PET, used alone or in combination with other imaging approaches such as MRI and CT. In some embodiments, the brain imaging is, or can include, MRI-ASL or MRI-BOLD. In yet another aspect, a method is provided wherein the method includes subjecting a patient to brain imaging determine regional metabolic activation in forebrain, midbrain and brainstem areas; administering to said patient clenbuterol and nadolol, wherein nadolol is administered in a dose of about 15 mg or less, and subsequently re-subjecting said patient to brain imaging to determine any improvement in regional metabolic activation in forebrain, midbrain and brainstem areas, cognitive function. In a similar aspect, a method is provided wherein the method includes subjecting a patient to brain imaging determine regional metabolic activation in forebrain, midbrain and brainstem areas; administering to said patient clenbuterol and nadolol, wherein nadolol is administered in a sub-therapeutic, and subsequently re-subjecting said patient to brain imaging to determine any improvement in regional metabolic activation in forebrain, midbrain and brainstem areas, cognitive function.

Clenbuterol is a $\beta_2$ agonist having the following chemical structure:

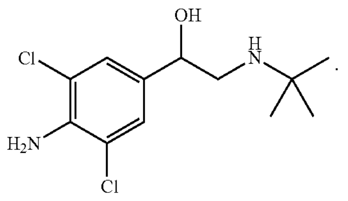 [SMILES: CC(C)(C)NCC(O)c1cc(Cl)c(N)c(Cl)c1]

In certain embodiments, clenbuterol as used herein refers to a racemic mixture. In other embodiments, the clenbuterol used herein may be (S)-clenbuterol that is substantially free of the (R)-clenbuterol isomer. In other embodiments, the clenbuterol used herein may be (R)-clenbuterol that is substantially free of the (S)-clenbuterol isomer. In one aspect, a method for improving cognitive function and/or treating a neurodegenerative disease is provided wherein the method includes administering to said patient clenbuterol and a PABRA to improve cognition and/or treat a neurodegenerative disease in said patient, wherein the PABRA is administered in a dose of about 15 mg or less. In one aspect, a method for improving cognitive function and/or treating a neurodegenerative disease is provided wherein the method includes administering to said patient clenbuterol and nadolol (PABRA) to improve cognition and/or treat a neurodegenerative disease in said patient, wherein nadolol is administered in a dose of about 15 mg or less. In one aspect, a method for improving cognitive function and/or treating a neurodegenerative disease is provided wherein the method includes administering to said patient clenbuterol and a PABRA to improve cognition and/or treat a neurodegenerative disease in said patient, wherein the PABRA is administered in a sub-therapeutic dose. In one aspect, a method for improving cognitive function and/or treating a neurodegenerative disease is provided wherein the method includes administering to said patient clenbuterol and nadolol to improve cognition and/or treat a neurodegenerative disease in said patient, wherein nadolol is administered in a sub-therapeutic dose. The method can further include subjecting a patient to brain imaging to determine regional metabolic activation in forebrain, midbrain and brainstem areas and/or to identify whether said patient is in need of or desiring improvement of cognitive function and/or treatment of a neurodegenerative disease. In some embodiments, nadolol is administered in a dose of about 0.01 to 15 mg, 0.1 to 15 mg, 0.1 to 10 mg, 0.1 to 1 mg, 0.1 to 0.5 mg, 0.2 to 0.3 mg, 0.23 to 0.27 mg; 0.1 to 5 mg, 1 to 15 mg, 1 to 10 mg, 1 to 5 mg, 5 to 10 mg, 10 mg or less, 7 mg or less, 5 mg or less, 1 mg or less, about 0.01 mg, about 0.05 mg; about 0.1 mg, about 0.2 mg, about 0.25 mg, about 0.3 mg, about 0.4 mg, about 0.5 mg, about 1 mg, about 2 mg, about 3 mg, about 4 mg, about 5 mg, about 6 mg, about 7 mg, about 8 mg, about 9 mg, or about 10 mg. In some embodiments, clenbuterol can be administered at a dose of from about 30 to 160 μg. In some embodiments, clenbuterol can be administered at a dose of from about 50 to 160 μg or 80 to 160 μg For some embodiments, the above-mentioned doses are a total daily dose. For some embodiments, the above-mentioned doses are a weekly dose. For some embodiments, the dose of clenbuterol and nadolol are administered for a period of weeks or more. For some embodiments, nadolol is a mixture of four diastereomers. For some embodiments, the nadolol administered is a specific enantiomerically pure isomer.

In some embodiments, the brain imaging is fluorodeoxyglucose positron emission tomography (FDG-PET), used alone or in combination with other imaging approaches such as magnetic resonance imaging (MRI) and CT. In some embodiments, the brain imaging is, or can include, MRI-ASL or MRI-BOLD. In some embodiments of the aspects and embodiments disclosed herein, "improving cognition and/or treating a neurodegenerative disease" in a patient may include improving cognitive and executive function, improving inflammatory status in cerebral or cerebrospinal fluid (CSF) samples, attenuating proteinopathies burden (for example, based on imaging or CSF sampling) and/or improving regional cerebral metabolic status (reversing hypometabolism) in the patient. Likewise, in certain embodiments, "identifying a patient in need of or desiring improvement of cognitive function and/or treatment of a neurodegenerative disease" may include identifying a patient in need of or desiring improvement of cognitive and executive function, improvement of inflammatory status in cerebral or CSF samples, attenuation of proteinopathies burden (for example, based on imaging or CSF sampling) and/or improvement of regional cerebral metabolic status (reversing hypometabolism). In another aspect, a method is provided wherein the method includes subjecting a patient to brain imaging to determine regional metabolic activation in forebrain, midbrain and brainstem areas and/or to identify whether said patient is in need of or desiring improvement of cognitive function and/or treatment of a neurodegenerative disease, and administering to said patient clenbuterol or tulobuterol and nadolol to improve cognition and/or treat a neurodegenerative disease in said patient, wherein nadolol is administered in a dose of about 15 mg or less. In a related aspect, a method is provided wherein the method includes subjecting a patient to brain imaging to determine regional metabolic activation in forebrain, midbrain and brainstem areas and/or to identify whether said patient is in need of or desiring improvement of cognitive function and/or treatment of a neurodegenerative disease, and administering to said patient clenbuterol or tulobuterol and nadolol to improve cognition and/or treat a neurodegenerative disease in said patient, wherein nadolol is administered in a sub-therapeutic dose.

The method can further include subsequently re-subjecting said patient to brain imaging to determine any improvement in regional metabolic activation in forebrain, midbrain and brainstem areas, cognitive function and/or treatment of said neurodegenerative disease. In some embodiments, the brain imaging is FDG-PET, used alone or in combination with other imaging approaches such as MRI and CT. In some embodiments, the brain imaging is, or can include, MRI-ASL or MRI-BOLD. In yet another aspect, a method is provided wherein the method includes subjecting a patient to brain imaging determine regional metabolic activation in forebrain, midbrain and brainstem areas; administering to said patient clenbuterol or tulobuterol and nadolol to improve cognition and/or treat a neurodegenerative disease in said patient, wherein nadolol is administered in a dose of about 15 mg or less; and subsequently re-subjecting said patient to brain imaging to determine any improvement in regional metabolic activation in forebrain, midbrain and brainstem areas, cognitive function. In some embodiments, the brain imaging is FDG-PET, used alone or in combination with other imaging approaches such as MRI and CT. In some embodiments, the brain imaging is, or can include, MRI-ASL or MRI-BOLD.

Tulobuterol is a long-acting $\beta_2$ agonist having the following chemical structure:

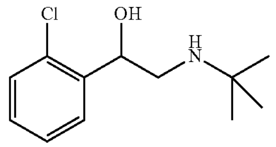

Tulobuterol is marketed in Japan as a racemic mixture for administration as a transdermal patch. In certain embodiments, tulobuterol as used herein refers to a racemic mixture. In other embodiments, the tulobuterol used herein may be (S)-tulobuterol that is substantially free of the (R)-tulobuterol isomer. In other embodiments, the tulobuterol used herein may be (R)-tulobuterol that is substantially free of the (S)-tulobuterol isomer. In one aspect, a method for improving cognitive function and/or treating a neurodegenerative disease is provided wherein the method includes administering to said patient tulobuterol and a PABRA to improve cognition and/or treat a neurodegenerative disease in said patient, wherein the PABRA is administered in a sub-therapeutic dose. In one aspect, a method for improving cognitive function and/or treating a neurodegenerative disease is provided wherein the method includes administering to said patient tulobuterol and nadolol to improve cognition and/or treat a neurodegenerative disease in said patient, wherein nadolol is administered in a dose of about 15 mg or less. In one aspect, a method for improving cognitive function and/or treating a neurodegenerative disease is provided wherein the method includes administering to said patient tulobuterol and a PABRA to improve cognition and/or treat a neurodegenerative disease in said patient, wherein the PABRA is administered in a sub-therapeutic dose. In one aspect, a method for improving cognitive function and/or treating a neurodegenerative disease is provided wherein the method includes administering to said patient tulobuterol and nadolol to improve cognition and/or treat a neurodegenerative disease in said patient, wherein nadolol is administered in a sub-therapeutic dose. The method can further include subjecting a patient to brain imaging to determine regional metabolic activation in forebrain, midbrain and brainstem areas and/or to identify whether said patient is in need of or desiring improvement of cognitive function and/or treatment of a neurodegenerative disease. In some embodiments, nadolol is administered in a dose of about 0.01 to 15 mg, 0.1 to 15 mg, 0.1 to 10 mg, 0.1 to 1 mg, 0.1 to 0.5 mg, 0.2 to 0.3 mg, 0.23 to 0.27 mg; 0.1 to 5 mg, 1 to 15 mg, 1 to 10 mg, 1 to 5 mg, 5 to 10 mg, 10 mg or less, 7 mg or less, 5 mg or less, 1 mg or less, about 0.01 mg, about 0.05 mg; about 0.1 mg, about 0.2 mg, about 0.25 mg, about 0.3 mg, about 0.4 mg, about 0.5 mg, about 1 mg, about 2 mg, about 3 mg, about 4 mg, about 5 mg, about 6 mg, about 7 mg, about 8 mg, about 9 mg, or about 10 mg. In some embodiments, tulobuterol can be administered in a dose from 0.5-20 mg; or 1-10 mg; or 2-8 mg; or about 1 mg; or about 2 mg; or about 3 mg; or about 4 mg;

or about 5 mg; or about 6 mg; or about 7 mg; or about 8 mg; or about 10 mg. For some embodiments, the above-mentioned doses are a total daily dose. For some embodiments, the above-mentioned doses are a weekly dose. For some embodiments, the dose of tulobuterol and nadolol are administered for a period of weeks or more. For some embodiments, nadolol is a mixture of four diastereomers. For some embodiments, the nadolol administered is a specific enantiomerically pure isomer.

In some aspects, a method is provided which includes treating a subject identified as having diminished cognitive function and/or being in need of or desiring improvement of cognitive function and/or treatment of a neurodegenerative disease by administering the subject a pharmaceutical composition including a $\beta_1$-AR agonist, a $\beta_2$-AR agonist, a peripherally acting β-blocker (PABRA), or any combination thereof. In some embodiments, the method further includes assessing effectiveness of the treatment. In some embodiments, the treatment is assessed by subjecting the subject to a test to assess improved cognitive function or amelioration of the neurodegenerative disease. In some embodiments, the method further includes adjusting administration of the pharmaceutical composition by adjusting dosage of the pharmaceutical composition and/or timing of administration of the pharmaceutical composition.

In some embodiments of any of the aspects or embodiments provided herein, the methods or compositions include a β-AR agonist and a PABRA. In some embodiments of any of the aspects or embodiments provided herein, the methods or compositions include a $\beta_2$-AR agonist and a PABRA. In some embodiments, the pharmaceutical composition includes clenbuterol and nadolol. In some embodiments, the pharmaceutical composition includes clenbuterol and atenolol. In some embodiments, the $\beta_2$-AR agonist can be administered at a dose of from about 30 to 160 μg. In some embodiments, the $\beta_2$-AR agonist can be administered at a dose of from about 50 to 160 μg. For some embodiments, the $\beta_2$-AR agonist can be administered at a dose of from about 1 to 300 μg, 5 to 200 μg, 10 to 180 μg, 10 to 40 μg, 20 to 50 μg, 40 to 80 μg, 50 to 100 μg, 100 to 200 μg, 30 to 160 μg, 50 to 160 μg, 80 to 160 μg, 100 to 160 μg, 120 to 160 μg, 140 to 160 μg, 150 to 170 μg, 30 to 140 μg, 50 to 140 μg, 80 to 140 μg, 100 to 140 μg, 120 to 140 μg, 30 to 120 μg, 50 to 120 μg, 80 to 120 μg, 100 to 120 μg, 30 to 100 μg, 50 to 100 μg, 80 to 100 μg, 30 to 80 μg, 50 to 80 μg, 30 to 50 μg, about 10 μg, about 20 μg, about 25 μg, about 30 μg, about 40 μg, about 50 μg, about 60 μg, about 70 μg, about 80 μg, about 90 μg, about 100 μg, about 110 μg, about 120 μg, about 125 μg, about 130 μg, about 140 μg, about 150 μg, or about 160 μg, about 170 μg, about 175 μg, about 180 μg, about 190 μg, about or 200 μg. In some embodiments, the $\beta_2$-AR agonist can be administered in a dose from 150 μg to 1 mg; or from 200 μg to 500 μg, or about 250 μg, or about 300 μg, or about 400 μg, or about 500 μg. In some embodiments, the $\beta_2$-AR agonist can be administered in a dose from 0.5-20 mg; or 1-10 mg; or 2-8 mg; or about 1 mg; or about 2 mg; or about 3 mg; or about 4 mg; or about 5 mg; or about 6 mg; or about 7 mg; or about 8 mg; or about 10 mg. In some embodiments of the aspects or embodiments provided herein the $\beta_2$-AR agonist is clenbuterol and the dose is 1 to 300 μg, 5 to 200 μg, 10 to 180 μg, 10 to 40 μg, 20 to 50 μg, 40 to 80 μg, 50 to 100 μg, 100 to 200 μg, 30 to 160 μg, 50 to 160 μg, 80 to 160 μg, 100 to 160 μg, 120 to 160 μg, 140 to 160 μg, 150 to 170 μg, 30 to 140 μg, 50 to 140 μg, 80 to 140 μg, 100 to 140 μg, 120 to 140 μg, 30 to 120 μg, 50 to 120 μg, 80 to 120 μg, 100 to 120 μg, 30 to 100 μg, 50 to 100 μg, 80 to 100 μg, 30 to 80 μg, 50 to 80 μg, 30 to 50 μg, about 10 μg, about 20 μg, about 25 μg, about 30 μg, about 40 μg, about 50 μg, about 60 μg, about 70 μg, about 80 μg, about 90 μg, about 100 μg, about 110 μg, about 120 μg, about 125 μg, about 130 μg, about 140 μg, about 150 μg, or about 160 μg, about 170 μg, about 175 μg, about 180 μg, about 190 μg, about or 200 μg. In some embodiments of the aspects or embodiments provided herein the $\beta_2$-AR agonist is tulobuterol and the dose is from 0.5-20 mg; or 1-10 mg; or 2-8 mg; or about 1 mg; or about 2 mg; or about 3 mg; or about 4 mg; or about 5 mg; or about 6 mg; or about 7 mg; or about 8 mg; or about 10 mg. For some embodiments, the above-mentioned doses are a total daily dose. For some embodiments, the above-mentioned doses are a total weekly dose. For some embodiments, the dose of agonist and PABRA are administered for a period of weeks or more.

As used herein, the term "$\beta_1$ agonist" is used to mean $\beta_1$-adrenergic receptor agonist or $\beta_1$-AR agonist. In certain embodiments the term $\beta_1$ agonist is understood to include compounds that are primarily $\beta_1$ agonists, but which may also exhibit some peripheral agonism for other adrenergic receptors, such as $\beta_2$-adrenergic receptors. In this application, the terms "$\beta_1$-adrenergic receptor agonist", "$\beta_1$-AR agonist", "$\beta_1$ AR agonist" and "$\beta_1$ agonist" may be used interchangeably. In certain embodiments, the term $\beta_1$-AR agonist expressly includes both selective and partial agonists, as well as biased and non-biased agonists. Examples of $\beta_1$ adrenergic agonists include, for example, xamoterol, noradrenalin, isoprenaline, dopamine and dobutamine and the pharmaceutically-acceptable salts of any of the above. Partial agonists and ligands of the $\beta_1$-AR are known. Further, using the methodology of Kolb et al., but for $\beta_1$-AR instead, one skilled in the art could determine new ligands by structure-based discovery. See *Proc. Natl. Acad. Sci. USA* 2009, 106, 6843-648.

As used herein, the term "$\beta_2$ agonist" is used to mean $\beta_2$-adrenergic receptor agonist or $\beta_2$-AR agonist. In certain embodiments, the term $\beta_2$ agonist is understood to include compounds that are primarily $\beta_2$ agonists, but which may also exhibit some peripheral agonism for other adrenergic receptors, such as $\beta_1$-adrenergic receptors. In this application the terms "$\beta_2$-adrenergic receptor agonist", "$\beta_2$-AR agonist", "$\beta_2$AR agonist" and "$\beta_2$ agonist" may be used interchangeably. In some embodiments the term $\beta_2$-AR agonist expressly includes both selective and partial agonists. $\beta_2$ agonists that may be used in accordance with various aspects and embodiments of the present disclosure may be short-acting, long-acting or ultra long-acting. Examples of short-acting $\beta_2$ agonists that may be used are salbutamol, levosalbutamol, terbutaline, pirbuterol, procaterol, metaproterenol, bitolterol mesylate, oritodrine, isoprenaline, salmefamol, fenoterol, terbutaline, albuterol, and isoetharine. Examples of long-acting $\beta_2$ agonists that may be used are salmeterol, bambuterol, formoterol and clenbuterol. Examples of ultra long-acting $\beta_2$ agonists include indacaterol, vilanterol and olodaterol. Other examples of $\beta_2$ agonists include tulobuterol, mabuterol, and ritodrine.

As used herein, the term "peripherally acting β-blocker (PABRA)" means a β adrenergic receptor antagonist or simply a $\beta_1$-, $\beta_2$- or non-selective β-blocker. Examples of selective peripherally acting β-blockers (PABRA) that may in certain embodiments be used in the methods disclosed herein include nadolol, atenolol, sotalol and labetalol. In certain embodiments a β-blocker that can be used in the methods herein is one or more selected from the group consisting of acebutolol, betaxolol, bisoprolol, celiprolol, esmolol, metaprolol and nevivolol; in other embodiments the methods do not use acebutolol, betaxolol, bisoprolol, celiprolol, esmolol, metaprolol or nevivolol as a β-blocker. Peripherally acting β-blocker (PABRA) can be used to reduce, restrict, or counter any adverse effects of the $\beta_1$-AR agonist and/or $\beta_2$-AR agonist, e.g., performance enhancing effects, and therefore reduces any risk of abuse. For example, nadolol can be used to reduce, restrict, or counter any peripheral β agonist effects of clenbuterol.

The term "about" as used herein means in quantitative terms plus or minus 10%. For example, "about 3%" would encompass 2.7-3.3% and "about 10%" would encompass 9-11%. Moreover, where "about" is used herein in conjunction with a quantitative term it is understood that in addition to the value plus or minus 10%, the exact value of the quantitative term is also contemplated and described. For example, the term "about 3%" expressly contemplates, describes and includes exactly 3%.

In certain embodiments a peripherally acting β-blocker (PABRA) is administered to the patient prior to administration of a $\beta_1$-AR agonist, a $\beta_2$-AR agonist, clenbuterol, and/or tulobuterol. In other embodiments, a peripherally acting β-blocker (PABRA) is administered to the patient concurrently with the administration of a $\beta_1$-AR agonist, a $\beta_2$-AR agonist, clenbuterol, and/or tulobuterol. In other embodiments, a peripherally acting β-blocker (PABRA) is co-administered to the patient in a single dosing formulation, in a single tablet and/or in a single capsule.

In certain embodiments of the compositions and methods provided herein, one or more peripherally acting β-blocker (PABRA) are administered prior to or concurrently with a $\beta_1$-AR agonist, a $\beta_2$-AR agonist, clenbuterol, and/or tulobuterol in order to inhibit or preclude agonism of peripheral $\beta_1$ and/or $\beta_2$ adrenergic receptors by the $\beta_1$-AR agonist, $\beta_2$-AR agonist, clenbuterol, and/or tulobuterol. In various embodiments it is preferred to block peripheral $\beta_1$ and/or $\beta_2$ adrenergic receptors in accordance with the compositions and methods of the present disclosure in order to preclude, or at least minimize, any adverse effects, e.g., peripheral cardiac effects, on humans being treated.

In certain embodiments of the methods provided herein, the $\beta_1$-AR agonist, $\beta_2$-AR agonist, clenbuterol, and/or tulobuterol is administered orally, intravenously, intramuscularly, transdermally, by inhalation or intranasally. In certain embodiments of the methods provided herein, the $\beta_1$-AR agonist, $\beta_2$-AR agonist, clenbuterol, and/or tulobuterol is administered orally.

In certain embodiments of the methods provided herein, the peripherally acting β-blocker (PABRA) is administered orally, intravenously, intramuscularly, by inhalation or intranasally. In certain embodiments of the methods provided herein, the peripherally acting β-blocker (PABRA) is administered orally.

In certain embodiments of the methods provided herein, the $\beta_1$-AR agonist, $\beta_2$-AR agonist, clenbuterol, and/or tulobuterol and the peripherally acting β-blocker (PABRA) are administered to the patient in a single formulation. In some embodiments, the single formulation is in the form of a tablet. For some embodiments both agents (β-AR agonist and PABRA) are present in a tablet. For some embodiments, the tablet includes 30 to 160 μg of clenbuterol, and/or 0.1 mg to 10 mg of tulobuterol, and from about 0.1 to 15 mg of the peripherally acting β-blocker (PABRA). For some embodiments, the tablet includes 30 to 160 μg of clenbuterol, and/or 0.1 mg to 10 mg of tulobuterol, and a PABRA in a sub-therapeutic dose. For some embodiments, the tablet includes from about 0.5 to 20 mg of the $\beta_1$-AR agonist, $\beta_2$-AR agonist, clenbuterol, and/or tulobuterol, and from about 0.1 to 15 mg of the peripherally acting β-blocker (PABRA). In some embodiments, the tablet includes the peripherally acting β-blocker (PABRA) in a sub-therapeutic dose. In some embodiments, the tablet includes the peripherally acting β-blocker (PABRA) in an amount that is 0.01 to 15 mg, 0.1 to 15 mg, 0.1 to 10 mg, 0.1 to 1 mg, 0.1 to 0.5 mg, 0.2 to 0.3 mg, 0.23 to 0.27 mg; 0.1 to 5 mg, 1 to 15 mg, 1 to 10 mg, 1 to 5 mg, 5 to 10 mg, 10 mg or less, 7 mg or less, 5 mg or less, 1 mg or less, about 0.01 mg, about 0.05 mg; about 0.1 mg, about 0.2 mg, about 0.25 mg, about 0.3 mg, about 0.4 mg, about 0.5 mg, about 1 mg, about 2 mg, about 3 mg, about 4 mg, about 5 mg, about 6 mg, about 7 mg, about 8 mg, about 9 mg, or about 10 mg. In some embodiments, the tablet includes the peripherally acting β-blocker (PABRA, such as nadolol or atenolol) in an amount that results in a dose of about 90% or less; or 85% or less; or 80% or less; or 75% or less; or 70% or less; or 65% or less; or 60% or less; or 55% or less; or 50% or less; or 45% or less; or 40% or less; or 35% or less; or 30% or less; or 25% or less; or 20% or less; or 15% or less; or 10% or less; or 5% or less; or 4% or less; or 3% or less; or 2.5% or less; or 2% or less; or 1.5% or less; or 1% or less; or 0.5% or less as compared to the 5 mg twice daily (or 10 mg total daily) dose; or in some embodiments a sub-therapeutic dose of a PABRA in the tablet may be about 90%; or about 85%; or about 80%; or about 75%; or about 70%; or 6 about 5%; or about 60%; or about 55%; or about 50%; or about 45%; or about 40%; or about 35%; or about 30%; or 25%; or about 20%; or about 15%; or about 10% or less; about 5%; or about 4%; or about 3%; or about 2.5%; or about 2%; or about 1.5% or less; or about 1%; or about 0.5% as compared to a dose that the agent is effective for, or approved for treating a specific disease indication. For some embodiments the tablet having the aforementioned doses is administered daily. For some embodiments the tablet having the aforementioned doses is administered weekly. In some embodiments, the tablet includes the peripherally acting β-blocker (PABRA) in an amount from about 5 to 10 mg. In some embodiments, the $\beta_1$-AR agonist, $\beta_2$-AR agonist, clenbuterol, and/or tulobuterol is present in the tablet from about 50 to 160 μg or 80 to 160 μg. For some embodiments, the $\beta_1$-AR agonist, $\beta_2$-AR agonist, clenbuterol, and/or tulobuterol is present in the tablet from about 30 to 160 μg, 50 to 160 μg, 80 to 160 μg, 100 to 160 μg, 120 to 160 μg, 140 to 160 μg, 30 to 140 μg, 50 to 140 μg, 80 to 140 μg, 100 to 140 μg, 120 to 140 μg, 30 to 120 μg, 50 to 120 μg, 80 to 120 μg, 100 to 120 μg, 30 to 100 μg, 50 to 100 μg, 80 to 100 μg, 30 to 80 μg, 50 to 80 μg, 30 to 50 μg, 30 μg, 40 μg, 50 μg, 60 μg, 70 μg, 80 μg, 90 μg, 100 μg, 110 μg, 120 μg, 130 μg, 140 μg, 150 μg, or 160 μg. For some embodiments, the $\beta_1$-AR agonist, $\beta_2$-AR agonist, clenbuterol, and/or tulobuterol is present in the tablet from 0.5-20 mg; or 1-10 mg; or 2-8 mg; or about 1 mg; or about 2 mg; or about 3 mg; or about 4 mg; or about 5 mg; or about 6 mg; or about 7 mg; or about 8 mg; or about 10 mg. For some embodiments, the above-mentioned doses are a total daily dose. For some embodiments, the above-mentioned doses are a weekly dose. For some embodiments, the dose of $\beta_1$-AR agonist, $\beta_2$-AR agonist, clenbuterol, and/or tulobuterol and the peripherally acting β-blocker (PABRA) in a tablet are administered for a period of weeks or more.

In certain embodiments of the methods provided herein, the $\beta_1$-AR agonist, $\beta_2$-AR agonist, clenbuterol, and/or tulobuterol and the peripherally acting β-blocker (PABRA) are administered to the patient in a joint formulation. For some embodiments, joint formulation includes from about 30 to 160 μg of the $\beta_1$-AR agonist, $\beta_2$-AR agonist, clenbuterol, and/or tulobuterol, and 15 mg or less of the peripherally acting β-blocker (PABRA). For some embodiments, joint formulation includes from about 0.5 to 20 mg of the $\beta_1$-AR agonist, $\beta_2$-AR agonist, clenbuterol, and/or tulobuterol, and 15 mg or less of the peripherally acting β-blocker (PABRA). In some embodiments, the joint formulation includes the peripherally acting β-blocker (PABRA) in an amount from about 0.1 to 15 mg, 0.1 to 10 mg, 0.1 to 1 mg, 0.1 to 5 mg, 1 to 15 mg, 1 to 10 mg, 1 to 5 mg, 10 mg or less, 7 mg or less, 5 mg or less, 1 mg or less, 0.1 mg, 0.5 mg, 1 mg, 2 mg, 3 mg, 4 mg, 5 mg, 6 mg, 7 mg, 8 mg, 9 mg, or 10 mg. In some embodiments, the joint formulation includes the peripherally acting β-blocker (PABRA) in an amount from about 5 to 10 mg. In some embodiments, the $\beta_1$-AR agonist, $\beta_2$-AR agonist, clenbuterol, and/or tulobuterol is present in the joint formulation from about 50 to 160 μg or 80 to 160 μg. For some embodiments, the $\beta_1$-AR agonist, $\beta_2$-AR agonist, clenbuterol, and/or tulobuterol is present in the joint formulation from about 30 to 160 μg, 50 to 160 μg, 80 to 160 μg, 100 to 160 μg, 120 to 160 μg, 140 to 160 μg, 30 to 140 μg, 50 to 140 μg, 80 to 140 μg, 100 to 140 μg, 120 to 140 μg, 30 to 120 μg, 50 to 120 μg, 80 to 120 μg, 100 to 120 μg, 30 to 100 μg, 50 to 100 μg, 80 to 100 μg, 30 to 80 μg, 50 to 80 μg, 30 to 50 μg, 30 μg, 40 μg, 50 μg, 60 μg, 70 μg, 80 μg, 90 μg, 100 μg, 110 μg, 120 μg, 130 μg, 140 μg, 150 μg, or 160 μg. In some embodiments, the $\beta_1$-AR agonist, $\beta_2$-AR agonist, clenbuterol, and/or tulobuterol is present in the joint formulation from about 0.5-20 mg. For some embodiments, the $\beta_1$-AR agonist, $\beta_2$-AR agonist, clenbuterol, and/or tulobuterol is present in the joint formulation from 0.5-20 mg; or 1-10 mg; or 2-8 mg; or about 1 mg; or about 2 mg; or about 3 mg; or about 4 mg; or about 5 mg; or about 6 mg; or about 7 mg; or about 8 mg; or about 10 mg. For some embodiments, the above-mentioned doses are a total daily dose. For some embodiments the doses of the joint formulations are administered weekly and the dose is total weekly dose. For some embodiments, the dose of $\beta_1$-AR agonist, $\beta_2$-AR agonist, clenbuterol, and/or tulobuterol and the peripherally acting β-blocker (PABRA) are administered daily or weekly for a period of weeks or more.

For some embodiments of the methods and compositions provided herein, both clenbuterol and nadolol are administered to the patient orally. For some embodiments, of the methods provided herein, clenbuterol and nadolol are administered to the patient orally and both agents are present in a tablet. For some embodiments, the tablet includes from about 30 to 160 μg of clenbuterol, and from about 0.1 to 15 mg of nadolol. In some embodiments, the tablet includes nadolol in an amount from about 5 to 10 mg. In some embodiments, the tablet includes nadolol in an amount from about 0.1 to 15 mg, 0.1 to 10 mg, 0.1 to 1 mg, 0.1 to 5 mg, 1 to 15 mg, 1 to 10 mg, 1 to 5 mg, 10 mg or less, 7 mg or less, 5 mg or less, 1 mg or less, 0.1 mg, 0.5 mg, 1 mg, 2 mg, 3 mg, 4 mg, 5 mg, 6 mg, 7 mg, 8 mg, 9 mg, or 10 mg. For some embodiments, nadolol is a mixture of four diastereomers. For some embodiments, the nadolol administered is a specific enantiomerically pure isomer.

In some embodiments, clenbuterol is present in a tablet from about 50 to 160 μg or 80 to 160 μg. For some embodiments, clenbuterol is present in the tablet from about 30 to 160 μg, 50 to 160 μg, 80 to 160 μg, 100 to 160 μg, 120 to 160 μg, 140 to 160 μg, 30 to 140 μg, 50 to 140 μg, 80 to 140 μg, 100 to 140 μg, 120 to 140 μg, 30 to 120 μg, 50 to 120 μg, 80 to 120 μg, 100 to 120 μg, 30 to 100 μg, 50 to 100 μg, 80 to 100 μg, 30 to 80 μg, 50 to 80 μg, 30 to 50 μg, 30 μg, 40 μg, 50 μg, 60 μg, 70 μg, 80 μg, 90 μg, 100 μg, 110 μg, 120 μg, 130 μg, 140 μg, 150 μg, or 160 μg. For some embodiments, the tablet would be a total daily dose and is expected to be administered daily for a period of weeks or more. For some embodiments, the tablet would be a total weekly dose and is expected to be administered weekly for a period of weeks or more. For some embodiments, nadolol can reduce, restrict, or counter any adverse effects of clenbuterol, e.g., performance enhancing effects, which reduce the likelihood of abuse.

For some embodiments of the methods and compositions provided herein, both tulobuterol and nadolol are administered to the patient orally. For some embodiments, of the methods provided herein, tulobuterol and nadolol are administered to the patient orally and both agents are present in a tablet. For some embodiments, the tablet includes from about 0.5-20 mg of tulobuterol, and from about 0.1 to 15 mg of nadolol. In some embodiments, the tablet includes nadolol in an amount from about 0.1 to 15 mg, 0.1 to 10 mg, 0.1 to 1 mg, 0.1 to 5 mg, 1 to 15 mg, 1 to 10 mg, 1 to 5 mg, 10 mg or less, 7 mg or less, 5 mg or less, 1 mg or less, 0.1 mg, 0.5 mg, 1 mg, 2 mg, 3 mg, 4 mg, 5 mg, 6 mg, 7 mg, 8 mg, 9 mg, or 10 mg. In some embodiments, the tablet includes nadolol in an amount from about 5 to 10 mg. For some embodiments, nadolol is a mixture of four diastereomers. For some embodiments, the nadolol administered is a specific enantiomerically pure isomer. In some embodiments, tulobuterol is present in the tablet from about 0.5-20 or 2-8 mg. For some embodiments, the tablet would be a total daily dose and is expected to be administered daily for a period of weeks or more. For some embodiments, the tablet would be a total weekly dose and is expected to be administered weekly for a period of weeks or more.

Clenbuterol, and certain other β-agonists, have hypertrophic and lipolytic properties side effect that have resulted in illicit abuse by athletes and individuals desiring muscle building, athletic performance-enhancing, and/or weight loss. These side effects and propensity for abuse have created hurdles for regulatory approval (such as FDA approval) and create a certain level of a public health risk. However, the hypertrophic and lipolytic actions are caused in large part by activation of peripheral β receptors; accordingly the hypertrophic and lipolytic side effects and propensity for abuse can be reduced, mitigated or eliminated by co-administering a PABRA such as disclosed herein in combination with a β-agonist. In particular if the β-agonist and PABRA are made and sold only in single formulations having both agents such as described herein, then it will be very difficult or impossible for those seeking illicit use or abuse to separate the agents to make a product that would be effective for muscle building, athletic performance-enhancing, or weight loss illicit use. Accordingly, in some aspects and embodiments, provided are compositions and methods that involve a single formulation (such as, for example an oral tablet) having a β-agonist and PABRA, that is effective for improving cognition (a CNS action) but that have a reduced risk of illicit use/abuse as compared to a formulation having only a β-agonist without a PABRA. In many embodiments a sub-therapeutic dose of the PABRA is sufficient to counteract the side effects of the β-agonist, accordingly, a single formulation (such as, for example an oral tablet) as described herein having a β-agonist and PABRA may have a therapeutically active dose of the β-agonist and a sub-therapeutic dose of the PABRA.

In some embodiments of the aspects and embodiments provided herein, the patient is identified as having a neurodegenerative disease that is one or more selected from the group consisting of MCI (mild cognitive impairment), aMCI (amnestic MCI), Vascular Dementia, Mixed Dementia, FTD (fronto-temporal dementia; Pick's disease), HD (Huntington disease), Rett Syndrome, PSP (progressive supranuclear palsy), CBD (corticobasal degeneration), SCA (spinocerebellar ataxia), MSA (Multiple system atrophy), SDS (Shy-Drager syndrome), olivopontocerebellar atrophy, TBI (traumatic brain injury), CTE (chronic traumatic encephalopathy), stroke, WKS (Wernicke-Korsakoff syndrome; alcoholic dementia & thiamine deficiency), normal pressure hydrocephalus, hypersomnia/narcolepsy, ASD (autistic spectrum disorders), FXS (fragile X syndrome), TSC (tuberous sclerosis complex), prion-related diseases (CJD etc.), depressive disorders, DLB (dementia with Lewy bodies), PD (Parkinson's disease), PDD (PD dementia), ADHD (attention deficit hyperactivity disorder), Alzheimer's disease (AD), early AD, and Down Syndrome (DS). In some embodiments the of the patient is identified as having a neurodegenerative disease that is one or more selected from the group consisting of MCI, aMCI, Vascular Dementia, Mixed Dementia, FTD (fronto-temporal dementia; Pick's disease), HD (Huntington disease), Rett Syndrome, PSP (progressive supranuclear palsy), CBD (corticobasal degeneration), SCA (spinocerebellar ataxia), MSA (Multiple system atrophy), SDS (Shy-Drager syndrome), olivopontocerebellar atrophy, TBI (traumatic brain injury), CTE (chronic traumatic encephalopathy), stroke, WKS (Wernicke-Korsakoff syndrome; alcoholic dementia & thiamine deficiency), normal pressure hydrocephalus, hypersomnia/narcolepsy, ASD (autistic spectrum disorders), FXS (fragile X syndrome), TSC (tuberous sclerosis complex), prion-related diseases (CJD etc.), depressive disorders, DLB (dementia with Lewy bodies), PD (Parkinson's disease), PDD (PD dementia), and ADHD (attention deficit hyperactivity disorder). In some embodiments the patient does not have Alzheimer's disease (AD). In some embodiments the patient does not have Down Syndrome. In some embodiments the patient does not have Parkinson's disease. In some embodiments the patient does not have dementia with Lewy bodies.

In some embodiments, the patient is subjected to a cognition test or model after said administration. In some embodiments, the patient is subjected to a cognition test or model after said administration wherein the cognition test or model is a memory test; a diagnostic indicator of mental status, brain function, mental condition; a contextual learning test and/or brain imaging. In some embodiments, the patient is subjected to a cognition test or model before said administration. In some embodiments, the patient is subjected to a cognition test or model before said administration wherein the cognition test or model is a memory test; a diagnostic indicator of mental status, brain function, mental condition; a contextual learning test and/or brain imaging. In some embodiments the patient is subjected to a cognition test or model such as a memory test; a diagnostic indicator of mental status, brain function, mental condition; a contextual learning test and/or brain imaging before said administration and the cognition test or model is used to identify a patient in need of or desiring improvement of cognitive function and/or treatment of a neurodegenerative disease in accordance with the methods and compositions provided herein. In some embodiments, the patient is subjected to a cognition test or model before and after said administration. In some embodiments, the patient is subjected to a cognition test or model before and after said administration wherein the cognition test or model is a memory test; a diagnostic indicator of mental status, brain function, mental condition; a contextual learning test and/or brain imaging.

In certain embodiments, the patient demonstrates improved cognition following said administration. In some embodiments, the patient demonstrates improved cognition as demonstrated by an improvement in a cognition test or model; a memory test; a diagnostic indicator of mental status, brain function, mental condition; a contextual learning test; brain imaging or the like in the patient.

"Improving cognition," "improved cognition" or "improvement in cognition" means an improvement in an individual's cognitive capacity, or memory, or the like. In certain embodiments, the methods described herein result in an improvement cognition, for example as demonstrated by an improvement in a cognition test, a memory test, brain imaging and/or a contextual learning test in the patient. In some embodiments, the methods described herein result in an improvement in a contextual learning test in the patient wherein said contextual learning test is a spatial contextual learning test or Arizona Cognitive Test Battery (ACTB).

In some embodiments, the patient is a mammal. In some embodiments the patient is a human. In some embodiments, the patient is a child human. In some embodiments the patient is an adult human. Child, as used herein, means a human from about 5 to 20 years of age. Adult, as used herein, means a human from about 21 years of age and older.

BRIEF DESCRIPTION OF THE DRAWINGS

The accompanying drawings, which are incorporated in and constitute a part of this specification, exemplify various embodiments of the present invention and, together with the description, serve to explain and illustrate principles of the present disclosure. The drawings are intended only to illustrate major features of the exemplary embodiments in a diagrammatic manner.

DETAILED DESCRIPTION OF THE INVENTION

Figure 1:
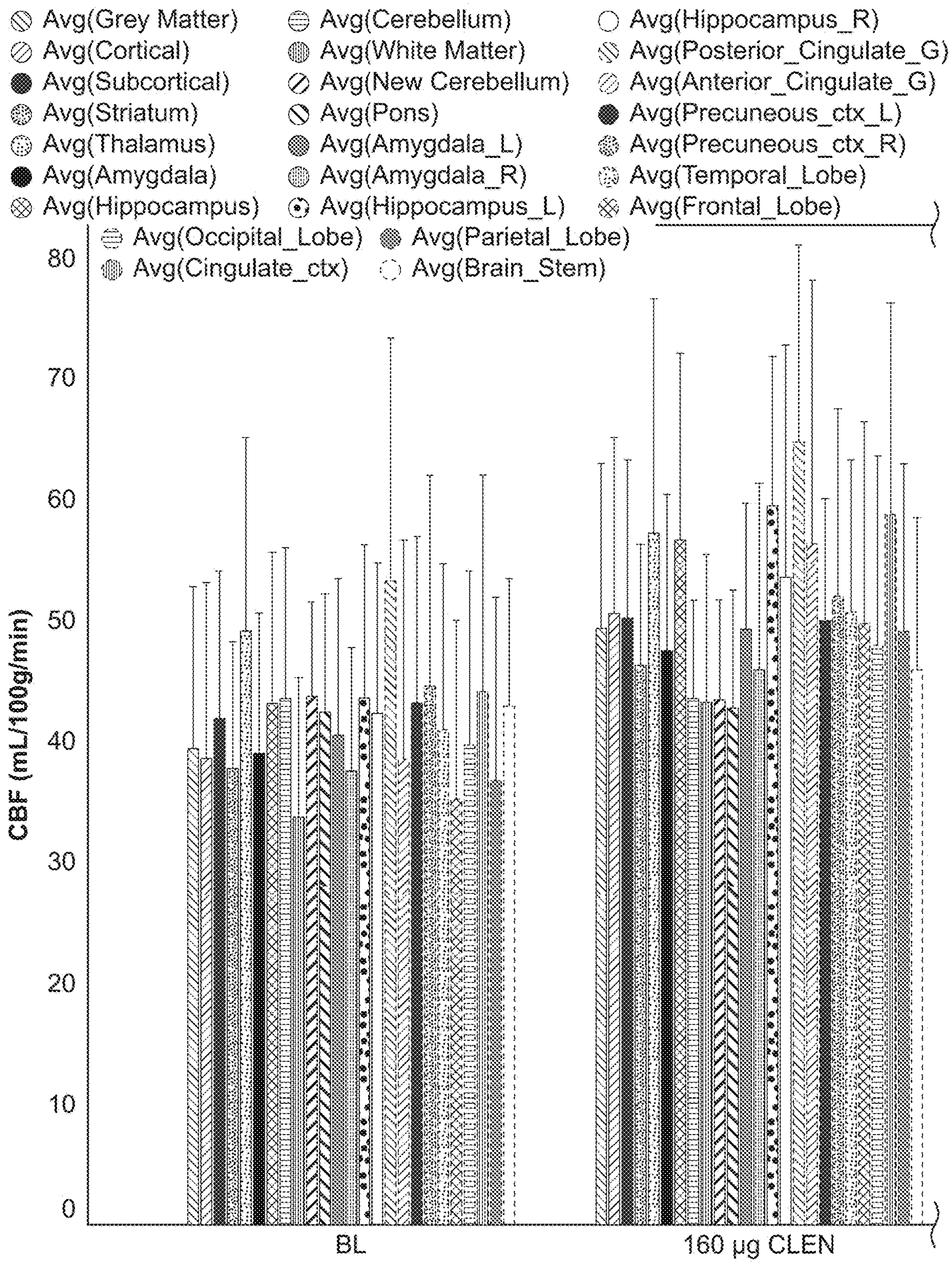
FIG. 1 shows a graph of cerebral blood flow in patients after being administered a single dose of clenbuterol and/or nadolol relative to their baseline.
Figure 1:
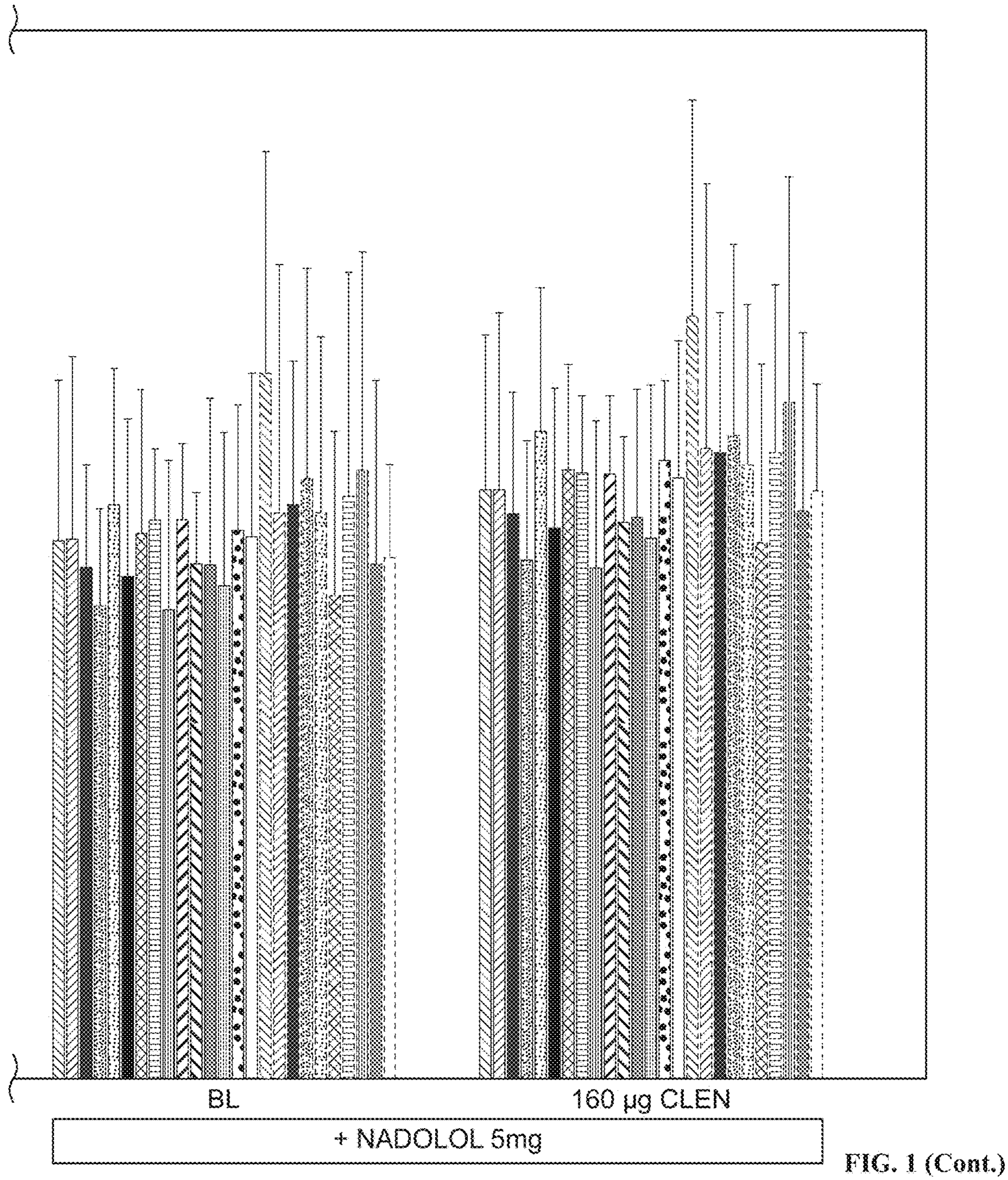
Figure 2:
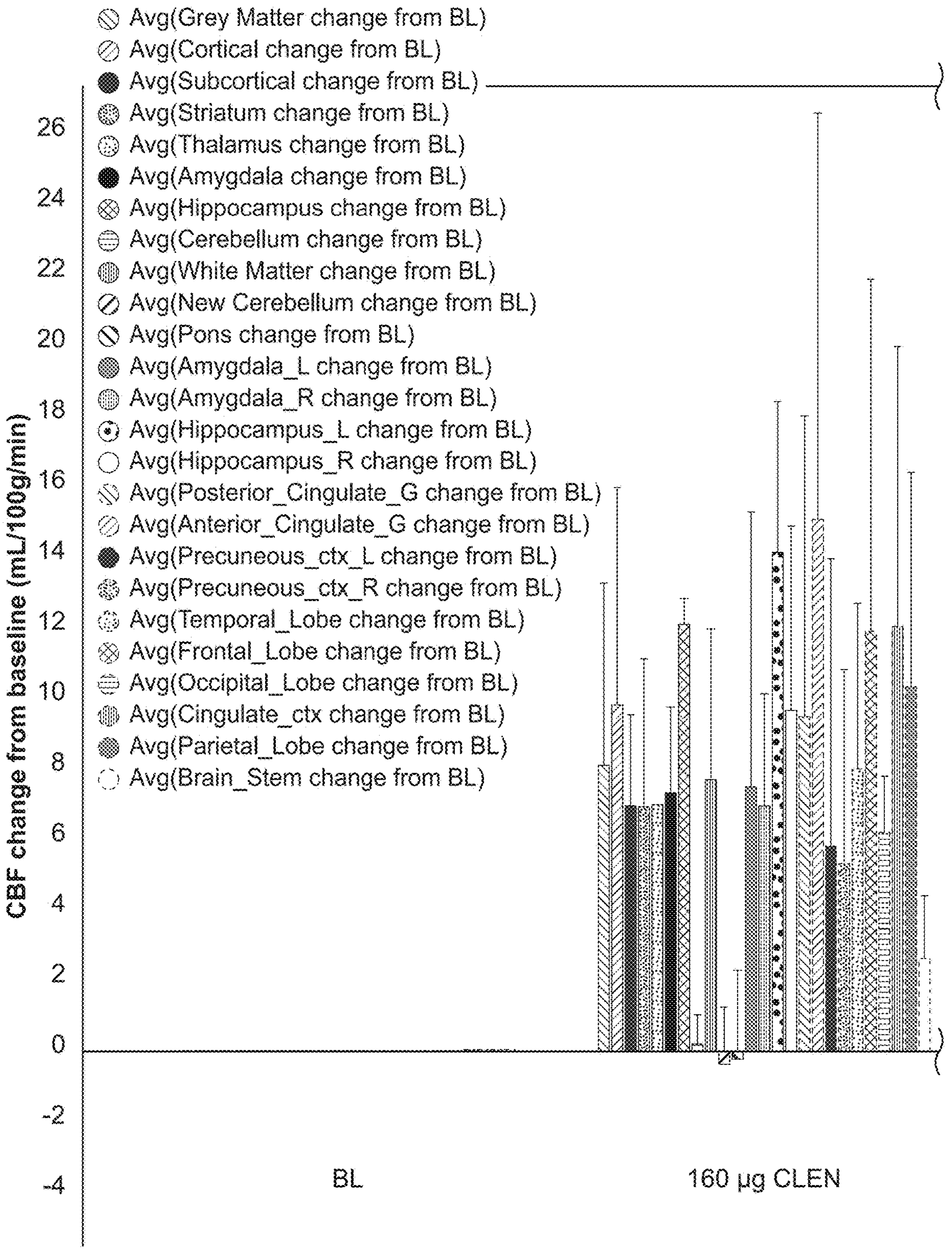
FIG. 2 shows a graph of cerebral blood flow in patients after being administered a single dose of clenbuterol and/or nadolol relative to their baseline.
Figure 2:
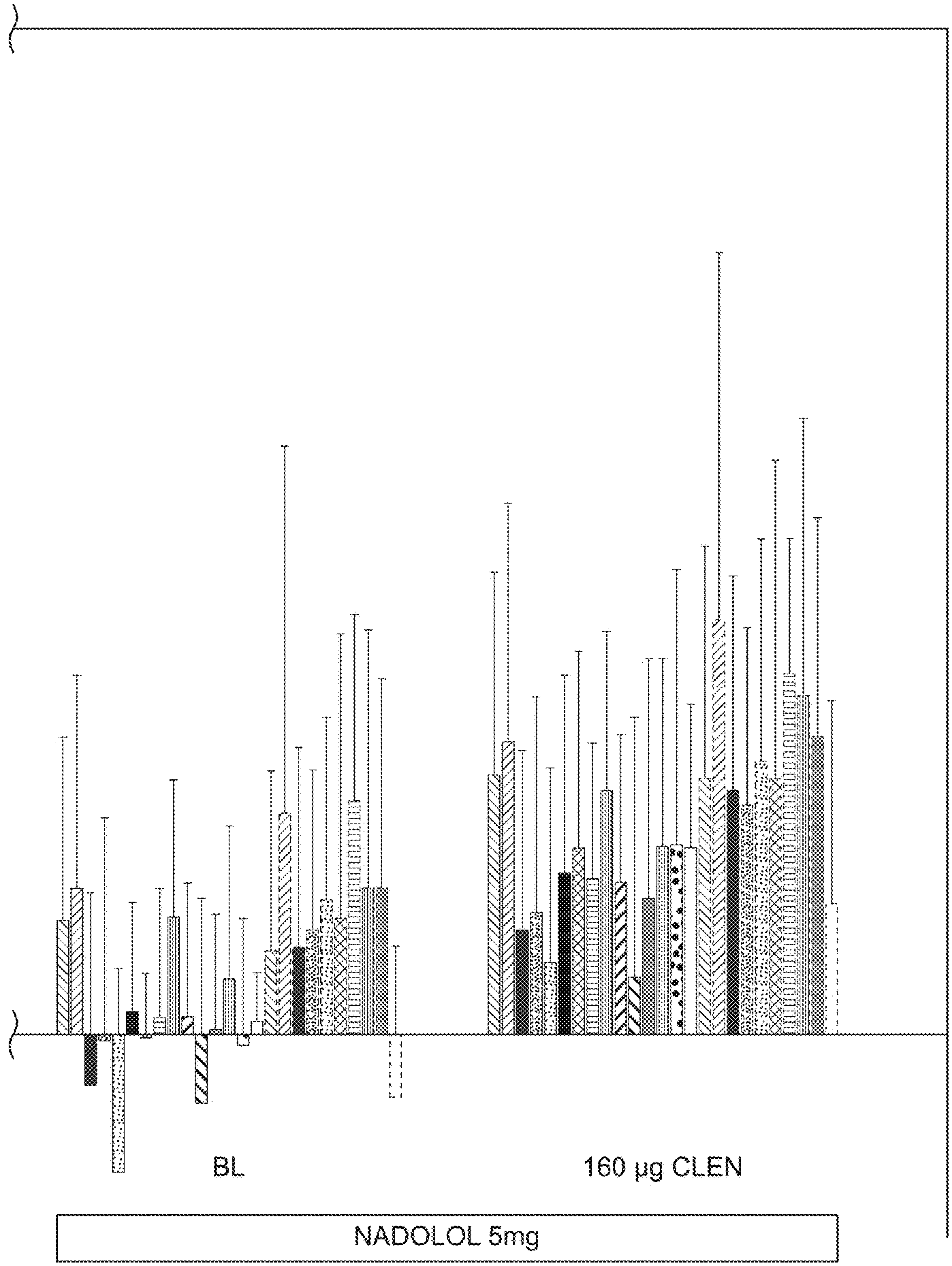

In certain aspects and embodiments of the present disclosure, compositions and methods result in an improved cognition, raised cerebral metabolic activity and/or improved inflammatory control in a patient. In some embodiments, the methods described herein result in an improvement cognition, for example as demonstrated by an improvement in a cognition test or model; a memory test; a diagnostic indicator of mental status, brain function, mental condition; a contextual learning test; or the like in the patient. Such cognitive tests, diagnostics and models are well known in the art. In various aspects and embodiments, any of many accepted contextual learning tests for animals or humans can be used to assess baseline cognitive function and/or to measure or quantify improved cognitive function. In some embodiments, the compositions and methods described herein may result in an improvement one or more tests, diagnostics and models as follows. Likewise for the raised cerebral metabolic activity and improved inflammatory control—these in certain embodiments may be imaged via FDG-PET and via sampling of cerebrospinal fluid (CSF) allowing measures of inflammatory cytokines and markers of glial cell activation. In some embodiments, magnetic resonance imaging-arterial spin labeling (MRI-ASL) can be used for neuroimaging. In some embodiments, magnetic resonance imaging-blood oxygenation level dependent computerized tomography (MRI-BOLD) can be used for neuroimaging. In various embodiments, FDG-PET may be used alone or in combination with CT and/or MRI including MRI-ASL and/or MRI-BOLD. For example, FDG-PET and MRI-BOLD may be used, or FDG-PET and MRI-ASL may be used. Alternatively, FDG-PET, MRI-BOLD and MRI-ASL may be used. Alternatively, MRI, including MRI-BOLD and MRI-ASL, may be used alone or in combination, and optionally with CT.

Human Models/Tests

There are many contextual learning tests used that are acknowledged and/or accepted in the art that in various embodiments may be used in conjunction with the compositions and methods disclosed herein to assess baseline cognitive function and/or to measure or quantify improved cognitive function in human subjects. For example, the contextual learning test used may be based upon single task learning, multiple task learning or spatial contextual memory. Contextual learning test evaluations based upon spatial contextual memory may be advantageous in assessing, for example, how well an individual is able to navigate a shopping mall, his or her neighborhood or a city transit or subway system as well as assessing any improvements in the ability to execute these tasks resulting from the treatment methods described herein.

An example of a simple spatial contextual learning test is contextual cuing, where humans learn to use repeated spatial configurations to facilitate a target search. A higher order spatial contextual learning test is serial learning, where humans learn to use subtle sequence regularities to respond more quickly and accurately to a series of events. See, for example, J. H. Howard Jr., et al., Neuropsychology, Vol. 18(1), January 2004, 124-134.

In some embodiments, cognition may be evaluated using the Mini-Mental State Examination (MMSE) and/or the Montreal Cognitive Assessment (MOCA).

Arizona Cognitive Test Battery (ACTB)

A testing protocol that may be used in various embodiments is the Arizona Cognitive Test Battery (ACTB). See Edgin, J., et al. J. Neurodevelop. Disord. (2010) 2: 149-164. The ACTB has been developed specifically to assess the cognitive phenotype in DS and includes various tests with various task demands and links with brain function. In more detail, tests are included for: 1) benchmarks, such as KBIT II verbal subscale and KBIT II non-verbal subscale IQ tests, 2) hippocampal function, 3) prefrontal function, 4) cerebellar function, 5) Finger sequencing tasks, 6) NEPSY visuomotor precision and 7) simple reaction time.

In some embodiments, cognition may be evaluated using the Cambridge Neuropsychological Test Automated Battery (CANTAB) assessment (see, for example, Sahakian, et al., (1988). *Brain.* 111 (3): 695-718). Cognitive domains, such as attention, visuospatial working memory, episodic memory, speed of process and executive function can be assessed using the CANTAB Battery Test, which includes the following:

- Reaction Time (RTI),
- Paired Associates Learning (PAL),
- Verbal Recognition Memory (VRM) Immediate Free Recall,
- Rapid Visual Information Processing (RVP),
- Spatial Working Memory (SWM),
- Adaptive Tracking, and
- VRM Delayed Free recall and Forced-Choice Recognition.

A correlation of domain/test, test description and certain primary abilities assessed in accordance with the ACTB is provided below:

| Domain/Test | Description | Primary Ability Assessed |
|---|---|---|
| 1) Benchmark<br>KBIT-II verbal subscale<br>KBIT-II nonverbal subscale | Points to pictures based on word or phrase<br>Semantic or visuo-spatial pattern completion | Verbal comprehension<br>Problem solving |
| 2) CANTAB spatial span | Touching boxes in order of changing color on screen | Immediate memory for spatial-temporal sequence |
| 3) Prefrontal Modified dots task | Press button below a cat, shifts to new rule, press across screen for a frog, etc. | Inhibitory control working memory |
| 4) CANTAB IED | Forced-choice discrimination task with change in relevant dimension | Set-shifting |
| 5) Hippocampal CANTAB | Recall for hidden abstract patterns | Spatial associative |

-continued

| Domain/Test | Description | Primary Ability Assessed |
|---|---|---|
| paired associates | | memory |
| 6) Virtual computer-generated arena | Navigation of a virtual arena(via joystick) to find a hidden target | Spatial memory |
| 7) Cerebellar Finger-sequencing task | Sequences generated by tapping a number of fingers (1, 2, 3, 4) to a lever in succession | Motor sequencing |
| 8) NEPSY visuo-motor precision | Follows two tracks with a pen | Visuo-motor tracking, hand-eye coord. |
| 9) CANTAB simple reaction time | Participants press button in response to a box presented on a screen | Motor response time and attention |

The above battery of tests in some embodiments may all be performed in order to assess all major cognitive processes balanced by the practical need for testing under time constraints. The cognitive tests herein may in certain embodiments be used in patients receiving treatment herein to monitor the patient's cognitive status and progression.

In some embodiments, the battery of tests may be conducted with a test group of individuals, and a control group individuals to demonstrate the effectiveness of various aspects and embodiments of the compositions and methods described herein. The test group may be treated with any of the treatment regimens described herein, and the control group is treated with placebo, such as a dextrose 5% saline solution by intranasal administration.

An improvement in cognitive function as defined herein as being at least a 10%, and preferably at least a 20% score improvement, on at least one, and preferably two or more, of the tests listed in the ATCB, for example. Anyone of the domain/tests listed for the ATCB above may be included in assessing whether an improvement occurred. Testing may be conducted after treatment or during treatment to ascertain whether modifications in dosage or frequency of treatment is warranted.

Brain Imaging

Generally, any non-invasive procedure many be used to both establish a baseline of brain pathology (existent or non-existent) from which baseline a treatment protocol is established. However, magnetic resonance imaging (MRI) may in some embodiments be preferred for neuroimaging examination because it allows for accurate measurement of the 3-dimensional (3D) volume of brain structures, especially the hippocampus and related regions. Such techniques are well known as described in U.S. Pat. No. 6,490,472, which patent is incorporated herein in the entirety.

Moreover, non-invasive optical imaging systems may also be used for monitoring neurological pathological events. See, for example, U.S. patent publication 2011/0286932, which is incorporated herein in the entirety. The technique described therein entails administration of a fluorescent marker to a human for staining Aβ peptides, imaging the retina of the DS human with an optical imaging system, and examining the images for stained Aβ peptides in order to determine whether onset of brain pathology (such as AD brain pathology) has occurred.

In certain embodiments, fluorodeoxyglucose positron emission tomography (FDG-PET) may be used for neuroimaging to determine cognitive function and/or identify a neurodegenerative disease in accordance with the compositions and methods described herein. The use of FDG-PET for monitoring cognitive function and/or diagnosing cognitive impairments or neurodegenerative diseases, and/or identifying patients in need of or desiring a treatment to improve cognitive function is described in, for example Brown et al., RadioGraphics, (2014) 34:684-701, and Shivamurthy et al., AJR, (2015) 204:W76-W85; both hereby incorporated by reference in their entirety. In various embodiments, FDG-PET may be used alone or in combination with CT and/or MRI including MRI-ASL and/or MRI-BOLD. For example, FDG-PET and MRI-BOLD may be used, or FDG-PET and MRI-ASL may be used. Alternatively, FDG-PET, MRI-BOLD and MRI-ASL may be used. Alternatively, MRI, including MRI-BOLD and MRI-ASL, may be used alone or in combination, and optionally with CT.

Alzheimer's Disease

AD brain pathology refers to the accumulation of highly degradation-resistant amyloid fibers that cause lesions in areas of the brain proximate thereto. Accumulation of these amyloid fibers to neurotoxic levels leads to destruction of nerve fibers, which, in turn, leads to the observed behavior associated with Alzheimer's dementia. Observed behavioral symptoms, which become progressively more severe with progression of the disease, often include loss of vocabulary, incorrect word substitutions (paraphasias), loss of reading and writing skills, increased risk of falling, wandering, loss of speech, apathy and even loss of muscle mass.

Down Syndrome

Creation of several trisomic mouse models has greatly facilitated progress in the understanding the neurobiological basis of cognitive dysfunction in DS. Among the mouse models, the Ts65Dn mouse is best characterized. It has an extra copy of approximately 140 mouse genes on chromosome 16, orthologous to those on human chromosome 21 (HSA21). Almost all genes in HSA21 with potential role in nervous system abnormalities are also found in Ts65Dn mice. Similar to DS, alterations in the structure and function of the hippocampus and failure in the induction of long-term potentiation (LTP) have been extensively reported in Ts65Dn mice. Ts65Dn mice are the most widely used in DS research and are considered to be an art-accepted model for investigations regarding DS in humans. Olson, L. E., et al., Dev. Dyn. 2004 July; 230(3):581-9.

DS is characterized by degeneration and dysfunction of multiple neuronal populations in the central nervous system (CNS). Among them, the hippocampal formation, i.e., the primary site for processing contextual learning shows significant abnormalities in DS. As a result, failure in contextual learning is a common finding in people with DS. To uncover the neurobiological basis of failed contextual learning in DS, the integrity of subcortical regions extensively projecting to the hippocampal formation have been examined. Through extensive innervation, these subcortical regions impose strong modulatory influence on hippocampal neurons. Among these subcortical regions, LC is of particular importance. LC neurons in the brainstem are the sole supplier of massive norepinephrine (NE)-ergic terminals for the hippocampus and play a significant role in wakefulness, attention, and navigational memory. Significant age-related degeneration of NE-ergic neurons of LC in Ts65Dn mice was found. Interestingly, the loss of LC terminals in Ts65Dn mice leads to further deterioration of cognitive dysfunction in these mice. Similarly, LC neurons undergo extensive age-dependent degeneration in DS. The critical role of NE-ergic system dysfunction in cognitive dysfunction in Ts65Dn has been supported by the fact that increasing brain NE levels with L-threo-3,4-dihydroxyphenylserine (L-DOPS), i.e., a NE prodrug, restored contextual learning in Ts65Dn mice. Although L-DOPS is in phase III clinical trial for the treatment of primary autonomic failure associated with Parkinson's disease, it is yet to be approved by the FDA and its long-term effects particularly in children have yet to be explored.

With respect to the agents described herein, the terms "modulate" and "modulation" refers to the upregulation (i.e., activation or stimulation) or downregulation (i.e., inhibition or suppression) of a response. A "modulator" is an agent, compound, or molecule that modulates, and may be, for example, an agonist, antagonist, activator, stimulator, suppressor, or inhibitor. The terms "inhibit", "reduce", remove as used herein refer to any inhibition, reduction, decrease, suppression, downregulation, or prevention in expression, activity or symptom and include partial or complete inhibition of activity or symptom. Partial inhibition can imply a level of expression, activity or symptom that is, for example, less than 95%, less than 90%, less than 85%, less than 80%, less than 75%, less than 70%, less than 65%, less than 60%, less than 55%, less than 50%, less than 45%, less than 40%, less than 35%, less than 30%, less than 25%, less than 20%, less than 15%, less than 10%, or less than 5% of the uninhibited expression, activity or symptom. The terms "eliminate" or "eradicate" indicate a complete reduction of activity or symptom.

As used herein, the term "a disorder" or "a disease" refers to any derangement or abnormality of function; a morbid physical or mental state. See Dorland's Illustrated Medical Dictionary, (W. B. Saunders Co. 27th ed. 1988).

As used herein, the term "treating" or "treatment" of any disease or disorder refers in one embodiment, to ameliorating the disease or disorder (i.e., slowing or arresting or reducing the development of the disease or at least one of the clinical symptoms thereof). In another embodiment "treating" or "treatment" refers to alleviating or ameliorating at least one physical parameter including those which may not be discernible by the patient. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to preventing or delaying the onset or development or progression of the disease or disorder.

In some embodiments, optically pure (S)-β agonist is used to the extent the $\beta_2$ agonist has a stereocenter, which is substantially free of (R)-β agonist. In some embodiments, optically pure (R)-β agonist is used, which is substantially free of (S)-β agonist. The term "pure", as used herein, refers to substances that have been separated from at least some or most of the components with which they are associated in nature or when originally generated or with which they were associated prior to purification. In general, such purification involves action of the hand of man. Pure agents may be partially purified, substantially purified, or pure. Such agents may be, for example, at least 50%, 60%, 70%, 75%, 80%, 85%, 90%, 95%, 96%, 97%, 98%, 99%, or more than 99% pure. In some embodiments, a nucleic acid, polypeptide, or small molecule is purified such that it constitutes at least 75%, 80%, 85%, 90%, 95%, 96%, 97%, 98%, 99%, or more, of the total nucleic acid, polypeptide, or small molecule material, respectively, present in a preparation. In some embodiments, an organic substance, e.g., a nucleic acid, polypeptide, or small molecule, is purified such that it constitutes at least 75%, 80%, 85%, 90%, 95%, 96%, 97%, 98%, 99%, or more, of the total organic material present in a preparation. Purity may be based on, e.g., dry weight, size of peaks on a chromatography tracing (GC, HPLC, etc.), molecular abundance, electrophoretic methods, intensity of bands on a gel, spectroscopic data (e.g., NMR), elemental analysis, high throughput sequencing, mass spectrometry, or any art-accepted quantification method. In some embodiments, water, buffer substances, ions, and/or small molecules (e.g., synthetic precursors such as nucleotides or amino acids), can optionally be present in a purified preparation. A purified agent may be prepared by separating it from other substances (e.g., other cellular materials), or by producing it in such a manner to achieve a desired degree of purity.

In some embodiments, contemplated methods may include for example, administering prodrugs of the compounds described herein, or a pharmaceutical composition thereof. The term "prodrug" refers to compounds that are transformed in vivo to yield a disclosed compound or a pharmaceutically acceptable salt, hydrate or solvate of the compound. The transformation may occur by various mechanisms (such as by esterase, amidase, phosphatase, oxidative and or reductive metabolism) in various locations (such as in the intestinal lumen or upon transit of the intestine, blood or liver). Prodrugs are well known in the art (for example, see Rautio, Kumpulainen, et al., Nature Reviews Drug Discovery 2008, 7, 255). In some embodiments, the prodrug structures are constructed according to the disclosure in U.S. Pat. No. 9,849,134, which is incorporated by reference herein in the entirety.

For example, if a compound of the disclosure or a pharmaceutically acceptable salt, hydrate or solvate of the compound contains a carboxylic acid functional group, a prodrug can comprise an ester formed by the replacement of the hydrogen atom of the acid group with a group such as $(C_{1-8})$alkyl, $(C_{2-12})$alkylcarbonyloxymethyl, 1-(alkylcarbonyloxy)ethyl having from 4 to 9 carbon atoms, 1-methyl-1-(alkylcarbonyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_{1-2})$alkylamino-$(C_{2-3})$alkyl (such as β-dimethylaminoethyl), carbamoyl-$(C_{1-2})$alkyl, N,N-di$(C_{1-2})$alkylcarbamoyl-$(C_{1-2})$alkyl and piperidino-, pyrrolidino- or morpholino$(C_{2-3})$alkyl.

Similarly, if a compound of the disclosure contains an alcohol functional group, a prodrug can be formed by the replacement of the hydrogen atom of the alcohol group with a group such as $(C_{1-6})$alkylcarbonyloxymethyl, 1-$((C_{1-6})$alkylcarbonyloxy)ethyl, 1-methyl-1-$((C_{1-6})$alkylcarbonyloxy)ethyl $(C_{1-6})$alkoxycarbonyloxy)methyl, N—$(C_{1-6})$alkoxycarbonylaminomethyl, succinoyl, $(C_{1-6})$ alkylcarbonyl, α-amino($C_{1-4}$)alkylcarbonyl, arylalkylcarbonyl and α-aminoalkylcarbonyl, or α-aminoalkylcarbonyl α-aminoalkylcarbonyl, where each α-aminoalkylcarbonyl group is independently selected from the naturally occurring L-amino acids, $P(O)(OH)_2$, —P(O)(O($C_{1-6}$)alkyl$)_2$ or glycosyl (the radical resulting from the removal of a hydroxyl group of the hemiacetal form of a carbohydrate).

If a compound of the disclosure incorporates an amine functional group, a prodrug can be formed, for example, by creation of an amide or carbamate, an N-alkylcarbonyloxyalkyl derivative, an (oxodioxolenyl)methyl derivative, an N-Mannich base, imine or enamine. In addition, a secondary amine can be metabolically cleaved to generate a bioactive primary amine, or a tertiary amine can metabolically cleave to generate a bioactive primary or secondary amine. For examples, see Simplicio, et al., Molecules 2008, 13, 519 and references therein.

"Therapeutically effective amount" as used herein means the amount of a compound or composition (such as described herein) that causes at least one desirable change in a cell, population of cells, tissue, individual, patient or the like. In some embodiments a therapeutically effective amount as used herein means the amount of a compound or composition (such as described herein) that prevents or provides a clinically significant change in a disease or condition (e.g., reduce by at least about 30 percent, at least about 50 percent, or at least about 90 percent) or in one or more features of a disease or condition described herein. In some embodiments, the term "therapeutically effective amount" means an amount of a compound or composition as described herein effective or sufficient to improve cognition and/or treat a neurodegenerative disease in a patient. The term "frequency" as related thereto means the number of times a treatment is administered to a patient in order to obtain the result of improved cognition and/or treating a neurodegenerative disease in a patient.

Diagnostics and Assessment of Treatment

In various aspects, the methods of the disclosure include diagnosing or otherwise identifying whether a patient is in need of or desiring improvement of cognitive function and/or treatment of a neurodegenerative disease. As discussed herein, this may be performed in a variety of ways as discussed herein and generally known in the art. For example, a patient diagnosis may be made by brain imaging. In various embodiments, FDG-PET may be used alone or in combination with CT and/or MRI including MRI-ASL and/or MRI-BOLD. For example, FDG-PET and MRI-BOLD may be used, or FDG-PET and MRI-ASL may be used. Alternatively, FDG-PET, MRI-BOLD and MRI-ASL may be used. Alternatively, MRI, including MRI-BOLD and MRI-ASL, may be used alone or in combination, and optionally with CT.

Along with identifying suitable patients for treatment, diagnosis allows further determinations to be made regarding various aspects of the type and mode of treatment to be administered. For example, depending on the diagnosis, determinations may be made regarding the pharmaceutical active to be administered, the dosage of such actives as well as the timing schedule of administration.

A diagnostic method utilized with the methods of the disclosure may make use of a detectable label to diagnose or otherwise identify a patient that is in need of or desiring improvement of cognitive function and/or treatment of a neurodegenerative disease. The term "label" (also referred to as "detectable label") refers to any moiety that facilitates detection and, optionally, quantification, of an entity that comprises it or to which it is attached. The label can be conjugated to or otherwise attached to a variety of entities, biological or otherwise. In general, a label may be detectable by, e.g., spectroscopic, photochemical, biochemical, immunochemical, electrical, optical, chemical or other means. In some embodiments a detectable label produces an optically detectable signal (e.g., emission and/or absorption of light), which can be detected e.g., visually or using suitable instrumentation such as a light microscope, a spectrophotometer, a fluorescence microscope, a fluorescent sample reader, a fluorescence activated cell sorter, a camera, or any device containing a photodetector. Labels that may be used in various embodiments include, e.g., organic materials (including organic small molecule fluorophores (sometimes termed "dyes"), quenchers (e.g., dark quenchers), polymers, fluorescent proteins); enzymes; inorganic materials such as metal chelates, metal particles, colloidal metal, metal and semiconductor nanocrystals (e.g., quantum dots); compounds that exhibit luminescence upon enzyme-catalyzed oxidation such as naturally occurring or synthetic luciferins (e.g., firefly luciferin or coelenterazine and structurally related compounds); haptens (e.g., biotin, dinitrophenyl, digoxigenin); radioactive atoms (e.g., radioisotopes such as $^3H$, $^{14}C$, $^{32}P$, $^{33}P$, $^{35}S$, $^{125}I$), stable isotopes (e.g., $^{13}C$, $^2H$); magnetic or paramagnetic molecules or particles, and the like. Fluorescent dyes include, e.g., acridine dyes; BODIPY, coumarins, cyanine dyes, napthalenes (e.g., dansyl chloride, dansyl amide), xanthene dyes (e.g., fluorescein, rhodamines), and derivatives of any of the foregoing. Examples of fluorescent dyes include Cy3, Cy3.5, Cy5, Cy5.5, Cy7, Alexa® Fluor dyes, DyLight® Fluor dyes, FITC, TAMRA, Oregon Green dyes, Texas Red, to name but a few. Fluorescent proteins include green fluorescent protein (GFP), blue, sapphire, yellow, red, orange, and cyan fluorescent proteins and fluorescent variants such as enhanced GFP (eGFP), mFruits such as mCherry, mTomato, mStrawberry; R-Phycoerythrin, and the like. Enzymes useful as labels include, e.g., enzymes that act on a substrate to produce a colored, fluorescent, or luminescent substance. Examples include luciferases, β-galactosidase, horseradish peroxidase, and alkaline phosphatase. Luciferases include those from various insects (e.g., fireflies, beetles) and marine organisms (e.g., cnidaria such as *Renilla* (e.g., *Renilla reniformis*, copepods such as *Gaussia* (e.g., *Gaussia princeps*) or *Metridia* (e.g., *Metridia longa, Metridia pacifica*), and modified versions of the naturally occurring proteins. A wide variety of systems for labeling and/or detecting labels or labeled entities are known in the art. Numerous detectable labels and methods for their use, detection, modification, and/or incorporation into or conjugation (e.g., covalent or noncovalent attachment) to biomolecules such as nucleic acids or proteins, and the like, are described in fain Johnson, I., and Spence, M. T. Z. (Eds.), The Molecular Probes® Handbook—A Guide to Fluorescent Probes and Labeling Technologies. 11th edition (Life Technologies/Invitrogen Corp.) available online on the Life Technologies website at invitrogen.com/site/us/en/home/References/Molecular-Probes-The-Handbook.html and Hermanson, G T., Bioconjugate Techniques, $2^{nd}$ ed., Academic Press (2008). Many labels are available as derivatives that are attached to or incorporate a reactive functional group so that the label can be conveniently conjugated to a biomolecule or other entity of interest that comprises an appropriate second functional group (which second functional group may either occur naturally in the biomolecule or may be introduced during or after synthesis). For example, an active ester (e.g., a succinimidyl ester), carboxylate, isothiocyanate, or hydrazine group can be reacted with an amino group; a carbodiimide can be reacted with a carboxyl group; a maleimide, iodoacetamide, or alkyl bromide (e.g., methyl bromide) can be reacted with a thiol (sulfhydryl); an alkyne can be reacted with an azide (via a click chemistry reaction such as a copper-catalyzed or copper-free azide-alkyne cycloaddition). Thus, for example, an N-hydroxysuccinimide (NHS)-functionalized derivative of a fluorophore or hapten (such as biotin) can be reacted with a primary amine such as that present in a lysine side chain in a protein or in an aminoallyl-modified nucleotide incorporated into a nucleic acid during synthesis. A label may be directly attached to an entity or may be attached to an entity via a spacer or linking group, e.g., an alkyl, alkylene, aminoallyl, aminoalkynyl, or oligoethylene glycol spacer or linking group, which may have a length of, e.g., between 1 and 4, 4-8, 8-12, 12-20 atoms, or more in various embodiments. A label or labeled entity may be directly detectable or indirectly detectable in various embodiments. A label or labeling moiety may be directly detectable (i.e., it does not require any further reaction or reagent to be detectable, e.g., a fluorophore is directly detectable) or it may be indirectly detectable (e.g., it is rendered detectable through reaction or binding with another entity that is detectable, e.g., a hapten is detectable by immunostaining after reaction with an appropriate antibody comprising a reporter such as a fluorophore or enzyme; an enzyme acts on a substrate to generate a directly detectable signal). A label may be used for a variety of purposes in addition to or instead of detecting a label or labeled entity. For example, a label can be used to isolate or purify a substance comprising the label or having the label attached thereto.

The term "labeled" is used herein to indicate that an entity (e.g., a molecule, such as a biological or small molecule, organic compound, probe, cell, tissue, and the like) comprises or is physically associated with (e.g., via a covalent bond or noncovalent association) a label, such that the entity can be detected. In some embodiments a detectable label is selected such that it generates a signal that can be measured and whose intensity is related to (e.g., proportional to) the amount of the label. In some embodiments two or more different labels or labeled entities are used or present in a composition. In some embodiments the labels may be selected to be distinguishable from each other. For example, they may absorb or emit light of different wavelengths. In some embodiments the labels may be selected to interact with each other. For example, a first label may be a donor molecule that transfers energy to a second label, which serves as an acceptor molecule through nonradiative dipole—coupling as in resonance energy transfer (RET), e.g., Forster resonance energy transfer (FRET, also commonly called fluorescence resonance energy transfer).

Nuclear imaging is one of the most important tools of diagnostic medicine wherein an estimated 12-14 million nuclear medicine procedures are performed each year in the United States alone. Diagnostic nuclear imaging is therefore crucial for studies which determine the cause of a medical problem based on organ function, in contrast to radiographic studies, which determine the presence of disease based on static structural appearance.

Diagnostic radiopharmaceuticals and radiotracers are often designed or selected capable of selective binding to specific receptors by means of a binding moiety, such as an antibody, a specific inhibitor or other target-specific ligand. These targeted markers can therefore concentrate more rapidly in areas of interest, such as inflamed tissues, tumors, malfunctioning organs or an organ undergoing heightened expression of certain proteins. Thus, a blood circulating radiopharmaceutical is picked up by a specific organ or pathological tissue to a different extent than by other or non-pathological tissue. For example, a highly vascularized tissue (e.g., of a growing tumor) may concentrate more of a radiopharmaceutical while an ischemic tissue may concentrate less of the radiopharmaceutical than the surrounding tissues. Nuclear imaging relies on these general phenomena of varied distribution of radiopharmaceutical according to different tissue as well as different pathologies. As a result, specific tissue types (e.g., tumor tissues) may be distinguished from other tissues in radioactive-emission imaging.

Radiopharmaceuticals, which may be used in the process of differential diagnosis of pathologies may be conjugated to targeting (recognition binding) moieties and include a wide range of radioisotopes as mentioned below. Such radiopharmaceuticals therefore include recognition moieties such as, for example, monoclonal antibodies (which bind to a highly specific pre-determined target), fibrinogen (which is converted into fibrin during blood clotting), glucose and other chemical moieties and agents. Commonly used diagnostic conjugated radiopharmaceuticals include, for example, 2-[$^{18}$F]fluoro-2-deoxy-D-glucose ($^{18}$FDG), $^{111}$In-Pentetreotide ([$^{111}$In-DTPA-D-Phe$^{1}$]-octreotide), L-3-[$^{123}$I]-Iodo-α-methyl-tyrosine (IMT), O-(2-[$^{18}$F]fluoroethyl)-L-tyrosine (L-[$^{18}$F]FET), $^{111}$In-Capromab Pendetide (CYT-356, Prostascint) and $^{111}$In-Satumomab Pendetide (Oncoscint).

Two basic techniques are widely used for nuclear imaging: positron emission tomography (PET) and single photon emission computed tomography (SPECT). PET detects photons generated through positron-electron annihilation of positrons from a diagnostic radiopharmaceutical tracer placed in the subject, e.g., patient, to be imaged, and analyzes the photon energy and trajectory to generate tomographic images of the patient. SPECT generates images by computer analysis of photon emission events from a diagnostic radiopharmaceutical tracer having gamma emitting isotopes. Both PET and SPECT require the detection and analysis of single photon events, which are characterized by low signal to noise ratio and scarcity relative to the background radiation. Other constraints on the PET and SPECT image qualities include the sensitivity, temporal and spatial resolution, dynamic range, response time and counting rate characteristics of the data acquisition probe devices, e.g., photomultipliers and the like.

Radioisotopes that emit both high energy γ and/or low energy γ, β and/or positron radiation and which can be used per se or as a part of a compound as radiopharmaceuticals, include, without limitation, technetium-99m ($^{99m}$Tc), gallium-67 ($^{67}$Ga), thallium-201 ($^{201}$Tl), 111indium-($^{111}$In), iodine-123 ($^{123}$I), iodine-125 ($^{125}$I), iodine-131 ($^{131}$I), xenon-133 ($^{133}$Xe), and fluorine-18 ($^{18}$F). All these isotopes, except $^{99m}$Tc, $^{131}$I and $^{133}$Xe, are produced in particle accelerators.

Non-limiting examples of commonly used radiotracers include $^{99m}$Tc-Arcitumomab (CEA-Scan™) which is a monoclonal antibody for imaging colorectal tissues afflicted with colorectal cancer, $^{99m}$Tc-sestamibi (Cardiolite™) and $^{99m}$Tc-tetrofosmin (Myoview™) for imaging the heart of a subject for myocardial perfusion, $^{111}$In-Capromab pendetide (ProstaScint™) which is a monoclonal antibody for imaging prostate tissues afflicted with prostate cancer, $^{99m}$Tc-Fanolesomab (NeutroSpec™) which is a monoclonal antibody for imaging inflamed and infectious tissues and $^{90}$Y/111In-Zevalin (Ibritumomab Tiuxetan) which is a monoclonal antibody directed against the CD20 antigen, whereby this antigen is found on the surface of normal and malignant B lymphocytes.

Any diagnostic radiopharmaceutical can be utilized in the kit of the present embodiments. Exemplary radiopharmaceuticals that can be utilized in this context of the present invention include, without limitation, $^{3}$H-water, $^{3}$H-inulin, $^{11}$C-carbonmonoxide, $^{13}$N-ammonia, $^{14}$C-inulin, $^{15}$O—$H_2O$, $^{15}$O—$O_2$, $^{18}$F-fluorodeoxyglucose, $^{18}$F-sodium fluoride, $^{51}$Cr-erythrocytes (RBC), $^{57}$Co-vitamin B12 (cyanocobalamin), $^{58}$Co-vitamin B12 (cyanocobalamin), $^{59}$Fe-citrate, $^{60}$Co-vitamin B12 (cyanocobalamin), $^{67}$Ga-citrate, $^{68}$Ga-citrate, $^{75}$Se-selenomethionine, $^{81m}$Kr-krypton for inhalation, oral administration or injections, $^{82}$Rb, $^{85}$Sr-nitrate, $^{90}$Y/$^{111}$In-ibritumomab tiuxetan ($^{90}$Y/$^{111}$In-Zevalin), $^{99m}$Tc-albumin microspheres, $^{99m}$Tc-disofenin, lidofenin and mebrofenin, $^{99}$mTc-DMSA, $^{99m}$Tc-DTPA (injection), $^{99m}$Tc-DTPA (aerosol), $^{99m}$Tc-ECD (ethylene cystate dimer), $^{99m}$Tc-exametazime (HMPAO), $^{99m}$Tc-glucoheptonate, $^{99m}$Tc-HEDP, $^{99m}$Tc-HMDP, $^{99m}$Tc-HSA, $^{99m}$Tc-MAA, $^{99m}$Tc-MAG.sub.3, $^{99m}$Tc-MDP, $^{99m}$Tc-tetrofosmin (Myoview), $^{99m}$Tc-sestamibi (Cardiolite), $^{99m}$Tc-oral administrations, $^{99m}$Tc-pertechnetate, $^{99m}$Tc-pyrophosphate, $^{99m}$Tc-RBC in vitro and in vivo labeling, $^{99m}$Tc-sulfur colloid, $^{99m}$Tc-teboroxime, $^{99m}$Tc-white blood cells, $^{111}$In-ibritumomab tiuxetan ($^{111}$In-Zevalin), $^{111}$In-DTPA, $^{111}$In-platelets, $^{111}$In-RBC, $^{111}$In-white blood cells, $^{123}$I-hippuran, $^{123}$I-IMP, $^{123}$I-mIBG, $^{123}$I-sodium iodide, $^{124}$I-sodium iodide, $^{125}$I-fibrinogen, $^{125}$I-IMP, $^{125}$I-mIBG, $^{125}$I-sodium iodide, $^{126}$I-sodium iodide, $^{130}$-sodium iodide, $^{131}$I-hippuran, $^{131}$I-HSA, $^{131}$I-MAA, $^{131}$I-mIBG, $^{131}$I-Rose Bengal, $^{131}$I-sodium iodide, $^{127}$Xe-inhalation and injection, $^{133}$Xe-inhalation and injection, $^{197}$Hg-chlormerodrin, $^{198}$Au-colloid and $^{201}$Tl-chloride.

The diagnostic methods described herein may also but utilized to assess the effectiveness of a particular therapeutic regimen. For example, a patient that has been identified as being in need of or desiring improvement of cognitive function and/or treatment of a neurodegenerative disease and which is being treated, may be diagnosed or otherwise assessed to determine the effectiveness of the treatment regime. While the diagnosis or assessment may be performed by any method known in the art, cognitive testing or brain imaging may be used to determine improvement of cognitive function or amelioration of a disease. In embodiments, cognitive testing or brain imaging may be used alone or in combination. In embodiments where brain imaging is utilized, FDG-PET may be used alone or in combination with CT and/or MRI including MRI-ASL and/or MRI-BOLD. For example, FDG-PET and MRI-BOLD may be used, or FDG-PET and MRI-ASL may be used. Alternatively, FDG-PET, MRI-BOLD and MRI-ASL may be used. Alternatively, MRI, including MRI-BOLD and MRI-ASL, may be used alone or in combination, and optionally with CT.

The assessment of treatment efficacy may be utilized to alter the treatment regime of a patient. For example, the assessment may be utilized to alter dosing, timing of administration, and/or the actives of the pharmaceutical composition. In embodiments, the dosage of a particular pharmaceutical agent being administered to the patient may be lowered by combining administration with a different agent. In this manner, treatment may be optimized by altering the pharmaceutical composition to include different combinations of $\beta_1$-AR agonist, $\beta_2$-AR agonist, and peripherally acting β-blocker (PABRA). Dosing may also be altered depending on the timing of administration. For example, a shorter duration between each administration of the pharmaceutical composition may require a lower dose of active agent, while a longer duration between each administration of the pharmaceutical composition may require a higher dose of active agent, either of which may improve the treatment regime as determined by diagnosis or assessment of the patient.

In one embodiment, a patient may be assessed a single time during the course of treatment to optimize the treatment regime. Alternatively, the patient may be assessed multiple times over the course of treatment to continually optimize the treatment regime as directed by a medical professional.

Dosage, Administration and Pharmaceutical Formulation

The term "pharmaceutically-accepted salts" means acid addition salts that are commonly used in human or veterinary medicine and are deemed safe for use. Examples for the present disclosure include, but are not limited to, salts obtained from the following acids: acetic, ascorbic, benzenesulfonic, benzoic, camphosulfonic, citric, ethanesulfonic, edisylic, fumaric, gentisic, gluconic, glucoronic, glutamic, hippuric, hydrobromic, isethionic, lactic, nitric, phosphoric, succinic, sulfuric and tartaric, for example. Any hydrated forms of such salts are also included in this definition. Thus, for example, both fumarate and hemifumarate salts are specifically contemplated as well as any hydrates thereof. For example, fumarate dihydrate may be specifically mentioned.

The pharmaceutical preparation in some embodiments may be in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. Preferably, the unit dosage form is a tablet. The composition can, if desired, also contain other compatible therapeutic agents. Preferred pharmaceutical preparations can deliver the compounds of the disclosure in a sustained release formulation.

For a binding agent, composition, or compound according to the present disclosure, the dosage form may optionally be a liquid dosage form. Solutions can be prepared in water suitably mixed with a surfactant such as hydroxypropylcellulose or an emulsifier such as polysorbate. Dispersions can also be prepared in glycerol, liquid polyethylene glycols, DMSO and mixtures thereof with or without alcohol, and in oils. Under ordinary conditions of storage and use, these preparations contain a preservative to prevent the growth of microorganisms. Conventional procedures and ingredients for the selection and preparation of suitable formulations are described, for example, in Remington's Pharmaceutical Sciences (2003-20th edition) and in The United States Pharmacopeia: The National Formulary (USP 24 NF19) published in 1999. Formulations optionally contain excipients including, but not limited to, a buffering agents, an anti-oxidant, a stabilizer, a carrier, a diluent, and an agent for pH adjustment. The pharmaceutical forms suitable for injectable use include sterile aqueous solutions or dispersion and sterile powders for the extemporaneous preparation of sterile injectable solutions or dispersions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl, or benzyl alcohol; alkyl parabens such as methyl or propyl paraben; catechol; resorcinol; cyclohexanol; 3-pentanol; and m-cresol); low molecular weight (less than about 10 residues) polypeptides; proteins such as serum, albumin, gelatin, or immunoglobulins; hydrophilic polymers such as polyvinylpyrrolidone; amino acids such as glycine, glutamine, asparagine, histidine, arginine or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN, PLURONICS or polyethylene glycol (PEG).

In various embodiments, the dose of an agent may be determined by the human patient's body weight. For example, an absolute dose of an agent of about 30 to 160 μg for a pediatric human patient of about 0 to about 5 kg (e.g., about 0, or about 1, or about 2, or about 3, or about 4, or about 5 kg); or about 30 to 160 μg for a pediatric human patient of about 6 to about 8 kg (e.g., about 6, or about 7, or about 8 kg), or about 30 to 160 μg for a pediatric human patient of about 9 to about 13 kg (e.g., 9, or about 10, or about 11, or about 12, or about 13 kg); or about 30 to 160 μg for a pediatric human patient of about 14 to about 20 kg (e.g., about 14, or about 16, or about 18, or about 20 kg), or about 30 to 160 μg for a pediatric human patient of about 21 to about 30 kg (e.g., about 21, or about 23, or about 25, or about 27, or about 30 kg), or about 30 to 160 μg for a pediatric human patient of about 31 to about 33 kg (e.g., about 31, or about 32, or about 33 kg), or about 30 to 160 μg for an adult human patient of about 34 to about 50 kg (e.g., about 34, or about 36, or about 38, or about 40, or about 42, or about 44, or about 46, or about 48, or about 50 kg), or 30 to 160 μg for an adult human patient of about 51 to about 75 kg (e.g., about 51, or about 55, or about 60, or about 65, or about 70, or about 75 kg), or about 30 to 160 μg for an adult human patient of greater than about 114 kg (e.g., about 114, or about 120, or about 130, or about 140, or about 150 kg).

In certain embodiments, an agent in accordance with the methods provided herein is administered orally, subcutaneously (s.c.), intravenously (i.v.), intramuscularly (i.m.), intranasally or topically. Administration of an agent described herein can, independently, be one to four times daily; or one or two times weekly; or one to four times per month; or one to six times per year or once every two, three, four or five years. Administration can be for the duration of one day or one month, two months, three months, six months, one year, two years, three years, and may even be for the life of the human patient. The dosage may be administered as a single dose or divided into multiple doses. In some embodiments, an agent is administered about 1 to about 3 times (e.g., 1, or 2 or 3 times).

EXAMPLES

The present disclosure will be further described in the following examples, which do not limit the scope of the present disclosure.

Example 1

Treatment of Human Patients

Patients are screened using FDG-PET brain imaging. The identified as diagnosed with one or more of MCI, aMCI, Vascular Dementia, Mixed Dementia, FTD (fronto-temporal dementia; Pick's disease), HD (Huntington disease), Rett Syndrome, PSP (progressive supranuclear palsy), CBD (corticobasal degeneration), SCA (spinocerebellar ataxia), MSA (Multiple system atrophy), SDS (Shy-Drager syndrome), olivopontocerebellar atrophy, TBI (traumatic brain injury), CTE (chronic traumatic encephalopathy), stroke, WKS (Wernicke-Korsakoff syndrome; alcoholic dementia & thiamine deficiency), normal pressure hydrocephalus, hypersomnia/narcolepsy, ASD (autistic spectrum disorders), FXS (fragile X syndrome), TSC (tuberous sclerosis complex), prion-related diseases (CJD etc.), depressive disorders, DLB (dementia with Lewy bodies), PD (Parkinson's disease), PDD (PD dementia), or ADHD (attention deficit hyperactivity disorder).

A single dose of clenbuterol was provided to the patients ranging in an amount from 30 to 160 μg. A single dose of nadolol was also administered in some patients in an amount of 5 mg to counter any adverse effects of the clenbuterol. The patient are tracked over the course of 3 days after the single dose of clenbuterol and/or nadolol. The patients demonstrated robust global increase in cerebral blood flow from the baseline following treatment with clenbuterol and/or nadolol.

As shown in FIG. 1, a first group of patients was administered a single dose of clenbuterol in an amount of 160 μg and a second group of patients was administered a single dose of clenbuterol in an amount of 160 μg and nadolol in an amount of 5 mg. Relative to their baseline prior to the single dose of treatment, clenbuterol produces a robust global increase in cerebral blood flow (CBF) relative to the baseline in these patients. The second group of patients also demonstrated a robust global increase in cerebral blood flow (CBF) relative to the baseline in these patients, in which nadolol was also administered with clenbuterol to counter any adverse effects of clenbuterol.

Figure 3:
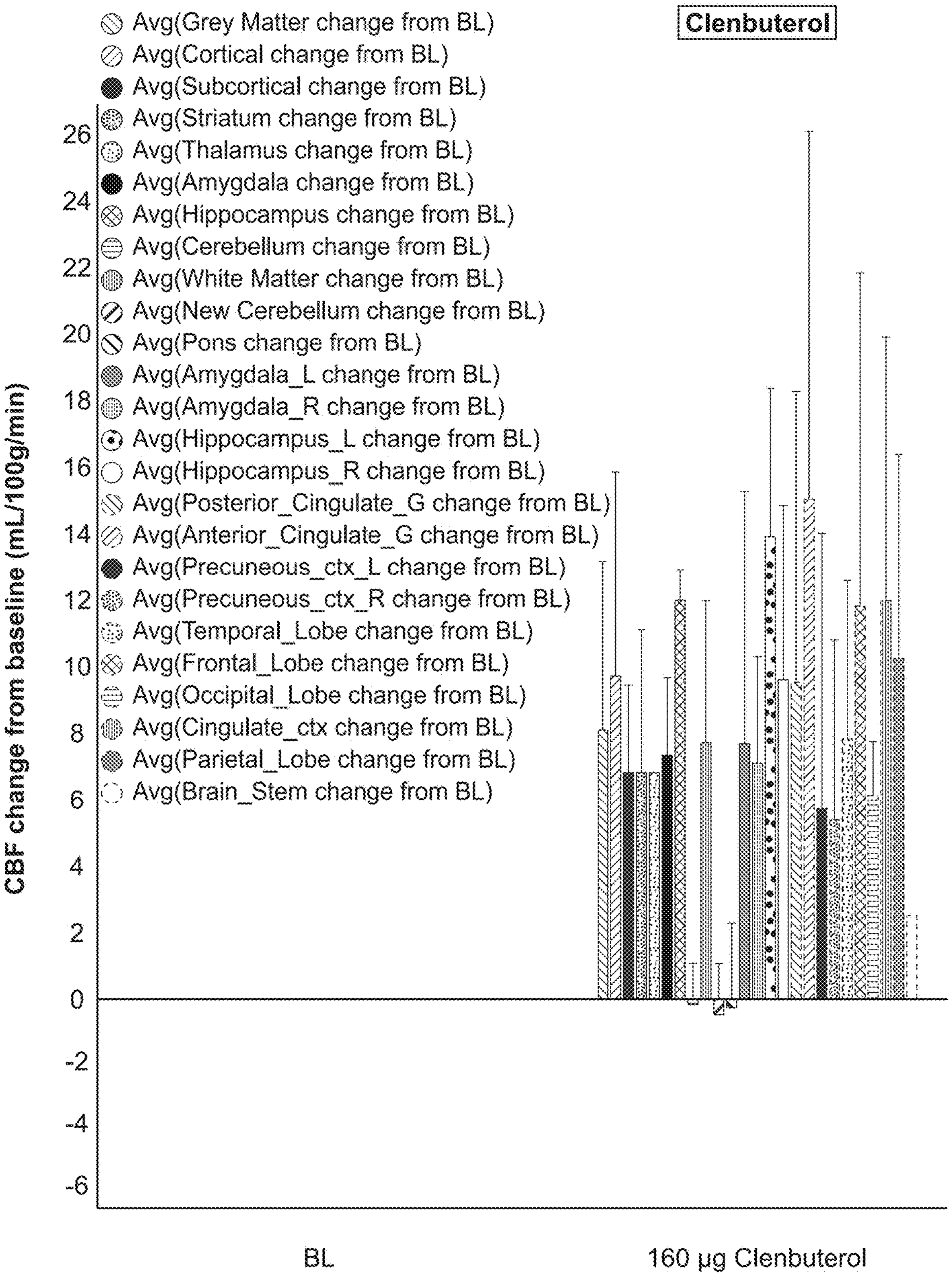
FIG. 3 shows a graph of cerebral blood flow in patients after being administered a single dose of clenbuterol and patients after being administered a single dose of pindolol relative to their baseline.
Figure 3:
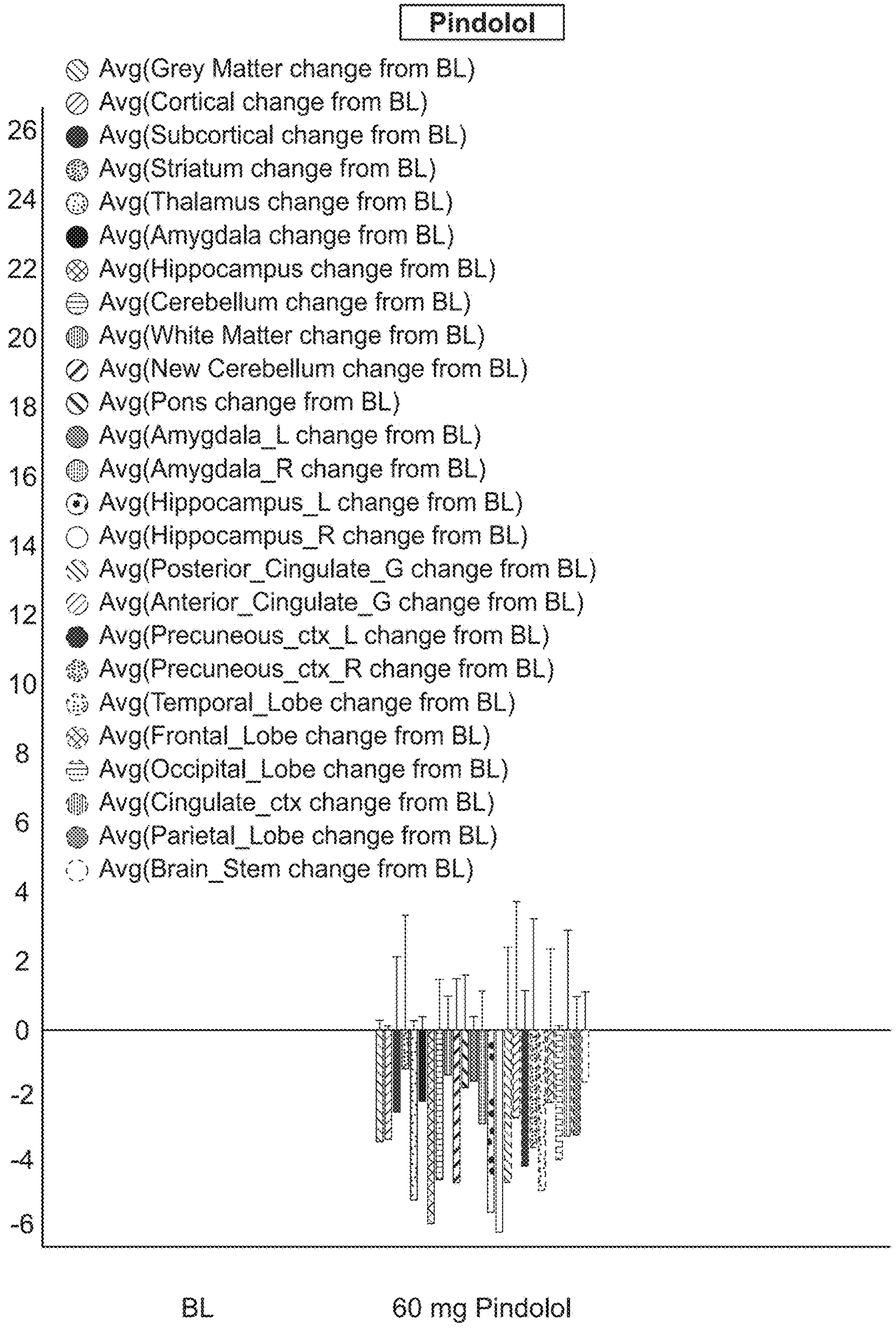

As shown in FIG. 3, a first group of patients was administered a single dose of clenbuterol in an amount of 160 μg and a second group of patients was administered a single dose of pindolol in an amount of 60 mg. Treatment with clenbuterol showed a positive increase in cerebral blood flow relative to the base line. Treatment with pindolol showed a decrease in cerebral blood flow relative to the base line.

Figure 4:
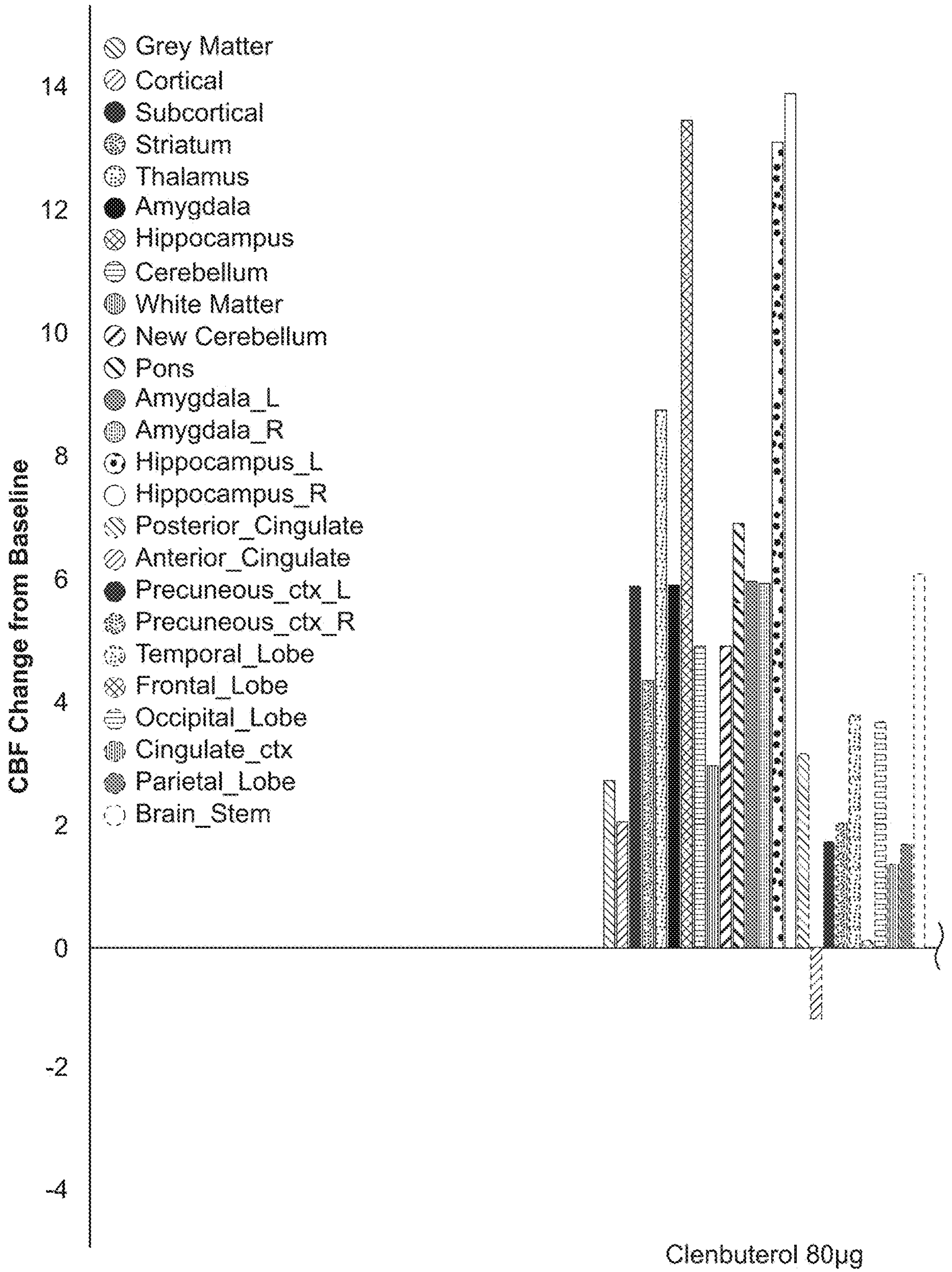
FIG. 4 shows a graph of cerebral blood flow in patients after being administered a single dose of clenbuterol in varying amounts relative to their baseline.
Figure 4:
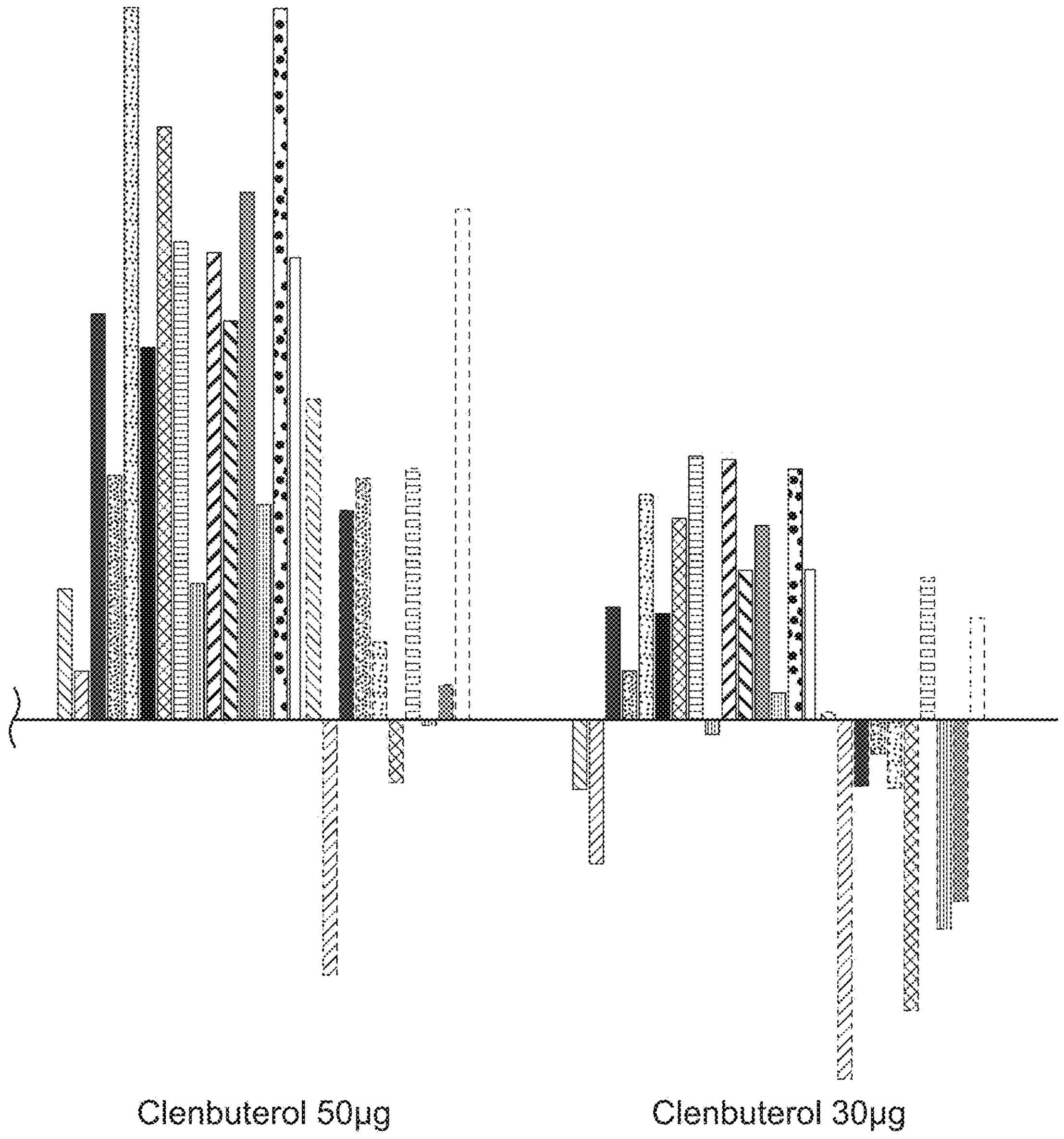
Figure 5:
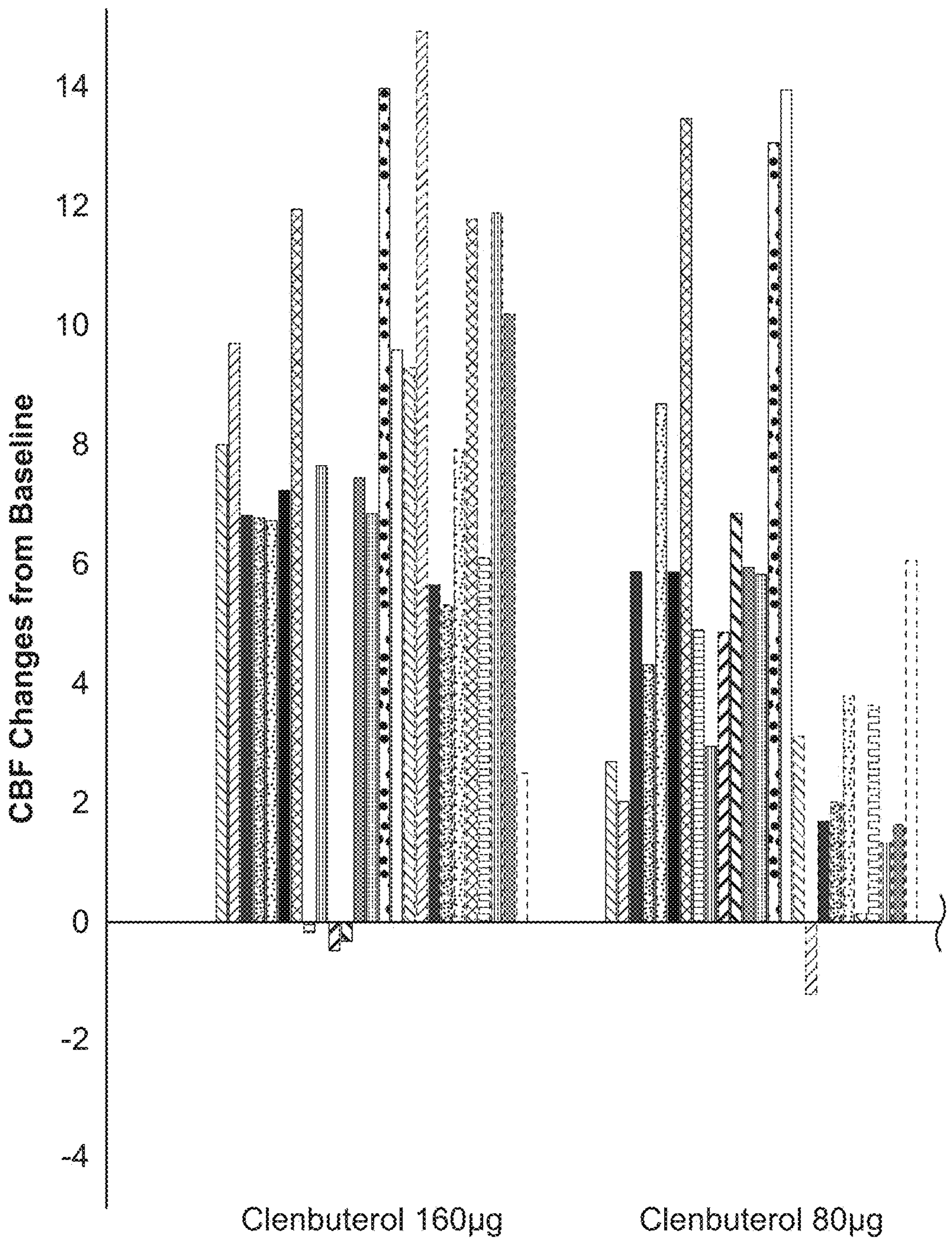
FIG. 5 shows a graph of cerebral blood flow in patients after being administered a single dose of clenbuterol in varying amounts and patients after being administered a single dose of clenbuterol and nadolol relative to their baseline.
Figure 5:
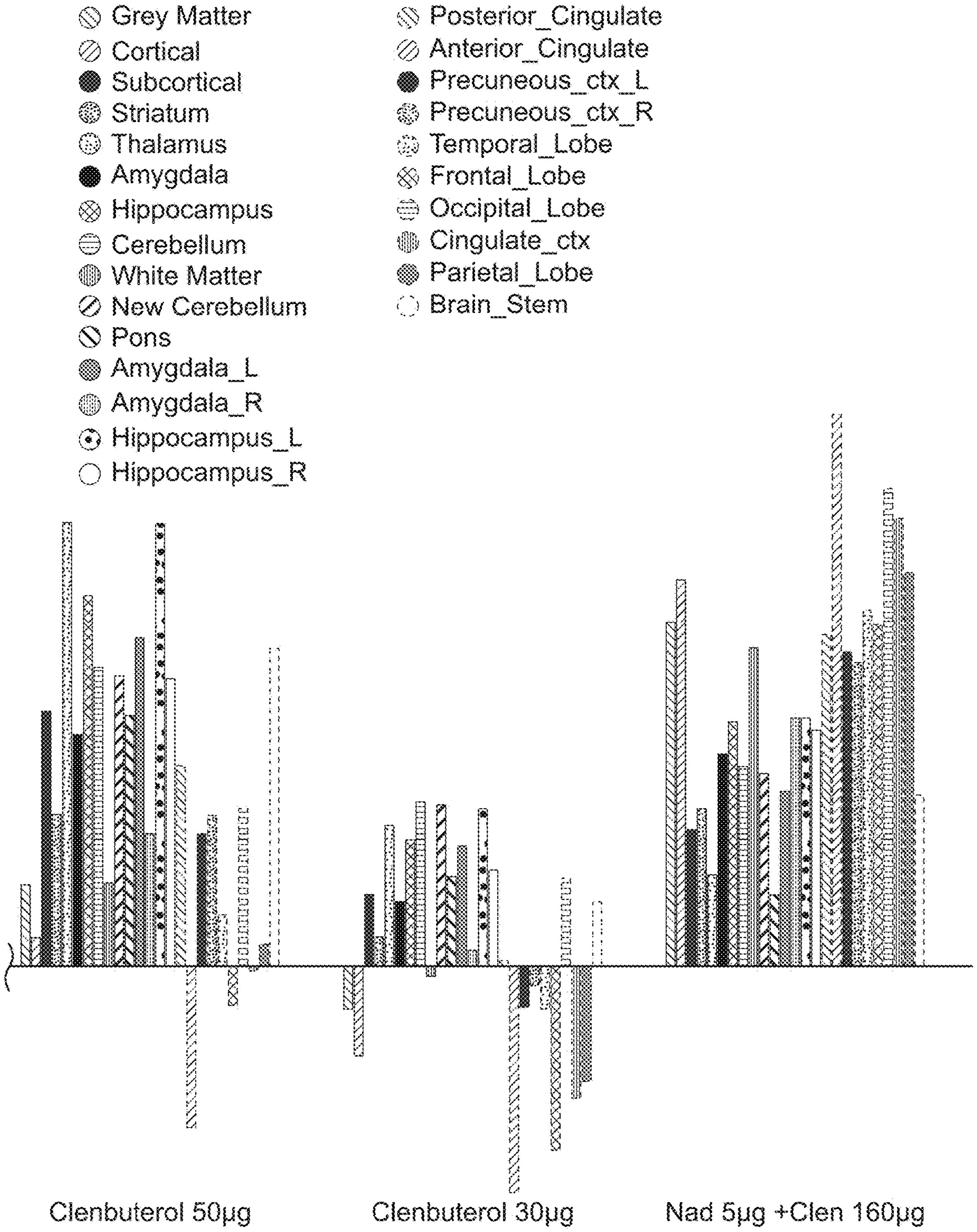

As shown in FIGS. 4 and 5, a groups of patients were administered a single dose of varying amounts of clenbuterol ranging from 30 to 160 μg, and another group of patients was administered a single dose of clenbuterol in an amount of 160 μg and nadolol in an amount of 5 mg to counter any adverse effects of clenbuterol. The patients were tracked over the course of 3 days. Relative to their baseline prior to the single dose of treatment, clenbuterol in an amount ranging from 30 to 160 μg produces a robust global increase in cerebral blood flow (CBF) relative to the baseline in these patients. The patients administered a single dose of clenbuterol in an amount of 160 μg and nadolol in an amount of 5 mg also showed a robust global increase in cerebral blood flow (CBF) relative to the baseline.

In some embodiments, cognitive tests and/or FDG-PET imaging can be used. In some embodiments, magnetic resonance imaging-arterial spin labeling (MRI-ASL) can be used for neuroimaging. In some embodiments, magnetic resonance imaging-blood oxygenation level dependent computerized tomography (MRI-BOLD) can be used for neuroimaging.

Example 2

Preparation of Substantially Free Tulobuterol Stereoisomers

Optically pure (S)-tulobuterol is prepared according to the following scheme using chemical synthesis methods that are well known in the art.

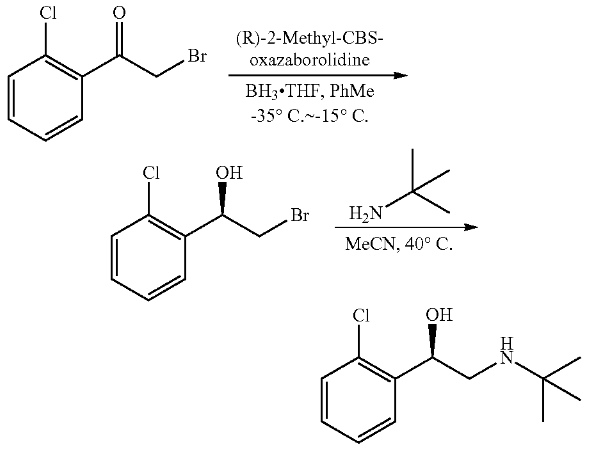

One ordinary skilled in the art can utilize routine purification technology such as HPLC or flash chromatography to purify the mixture from the above reaction to obtain optically pure (S)-tulobuterol that is substantially free of (R)-tulobuterol. Alternatively optically pure (S)-tulobuterol can be isolated from a racemic mixture, for example by following procedures outlined in patent JP 54151935; or using routine chiral HPLC separation technology (Journal of Pharmaceutical and Biomedical Analysis, 2018, 70-81); and using SFC separation technology (Journal of Chromatography A, 2014, 85-97).

Conversely, optically pure (R)-tulobuterol that is substantially free of (S)-tulobuterol is prepared according to the above scheme but replacing (R)-2-Methyl-CBS-oxazaborolidine in the scheme to (S)-2-Methyl-CBS-oxazaborolidine. Optically pure (R)-tulobuterol that is substantially free of (S)-tulobuterol can also be isolated from a racemic mixture using the above methodology to obtain optically pure (S)-tulobuterol.

Example 3

Cerebral Perfusion

Several recent studies have demonstrated the clinical relevance of cerebral perfusion (De Vis 2018, Staffaroni 2019). These studies demonstrate that cerebral perfusion declines with age, is correlated with the progression of AD, and is strongly correlated with cognitive performance such that subjects with higher cerebral perfusion tend to perform better in cognitive tests. Additionally, a study in AD patients demonstrated that the clinical effect of donepezil could be predicted by the perfusion increase seen after a single dose of the drug such that the subjects who had an increase in perfusion after acute administration were the same subjects who had a cognitive improvement after 6 months of treatment with the drug (Tepmongkol 2019). In a clinical study, healthy subjects were administered doses of clenbuterol ranging from 20 to 160 μg and ASL MRI was conducted prior to and after dosing with an objective to ascertain whether this neuroimaging method enables the detection of a clinically relevant CNS signal. The neuroimaging data from the study using ASL MRI demonstrated a clinically relevant signal, an increase in cerebral perfusion after a single dose of clenbuterol. Specifically, 160 μg of clenbuterol causes a robust global increase in cerebral perfusion and in particular in areas such as the hippocampus, thalamus, and cortex, all of which are very relevant in the pathogenesis of neurodegenerative disorders (see FIG. 6).

Figure 6:
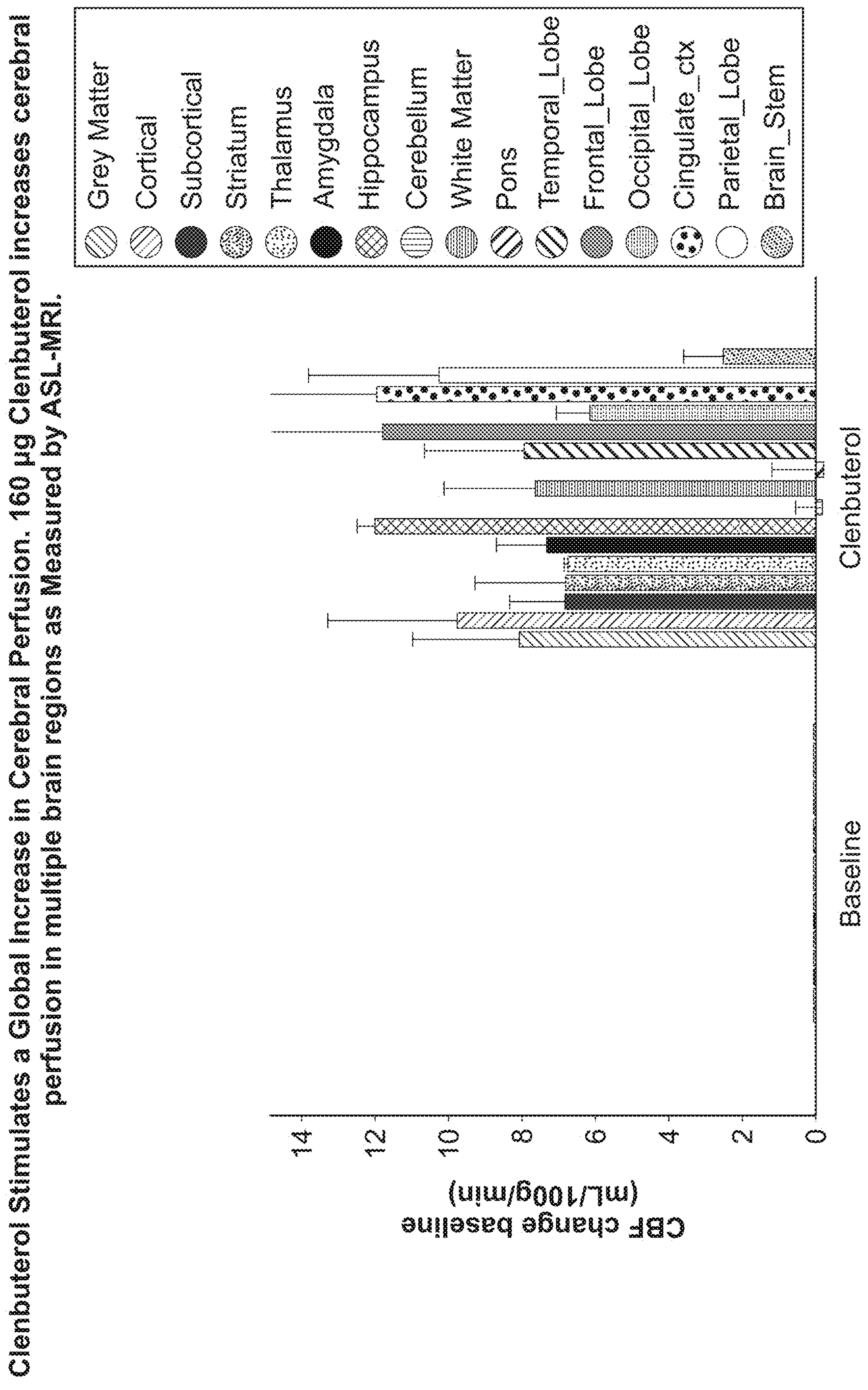
FIG. 6 shows that after dosing with a single dose of 160 μg of clenbuterol there is a global increase in cerebral perfusion. The legend on the right shows the different regions of interest (ROIs). The data are plotted as change from baseline in cerebral blood flow in different regions of the brain
Figure 7:
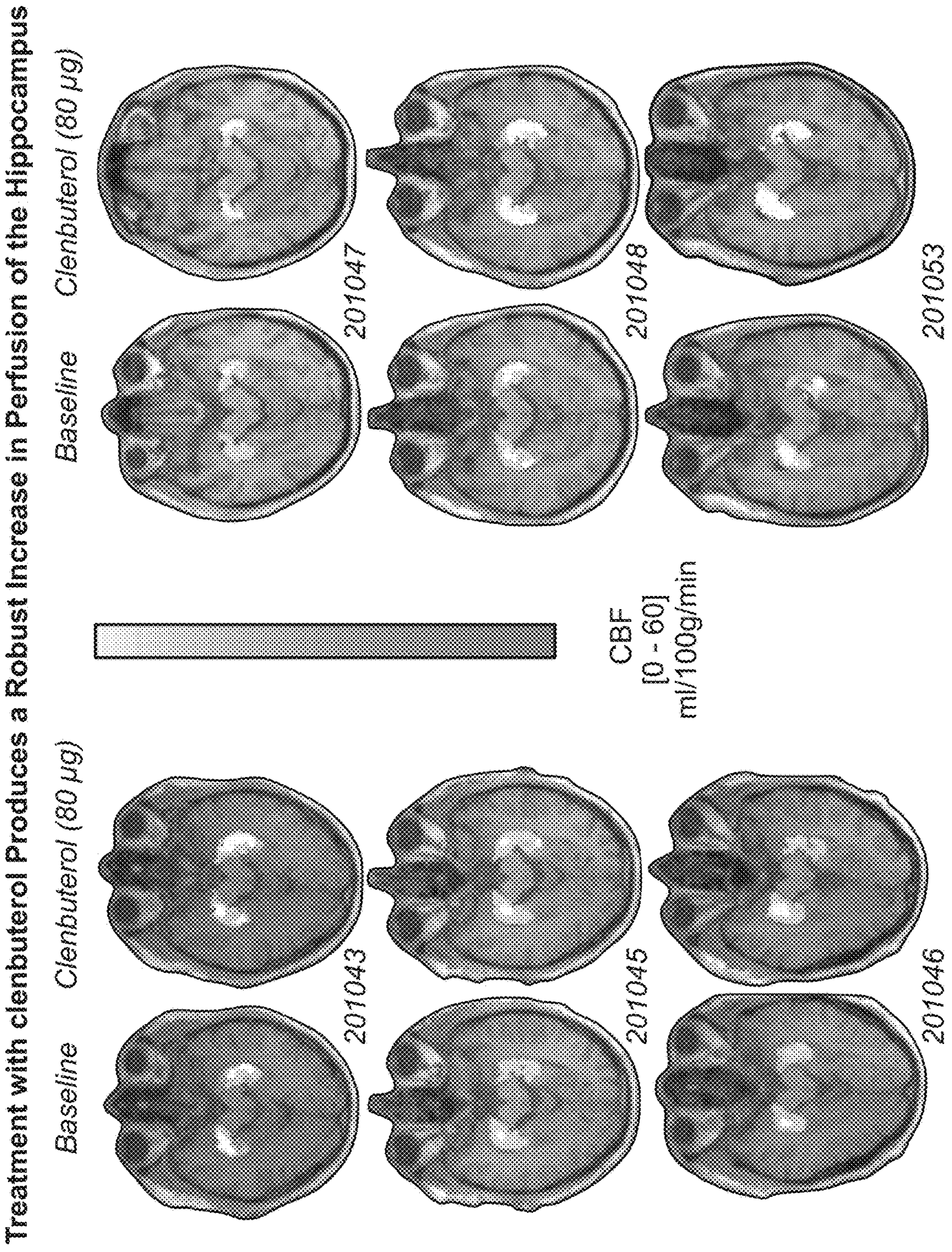
FIG. 7 shows a perfusion MRI-ASL image of the hippocampus as the region of interest (ROI). Six healthy subjects aged 44-52 were treated with a single dose of 80 μg clenbuterol. The Baseline vs. post-dose paired t-tests results: $p=0.019$. The color scale is shown in the middle and indicates cerebral blood flow with low values in red and high values in yellow.
Figure 8:
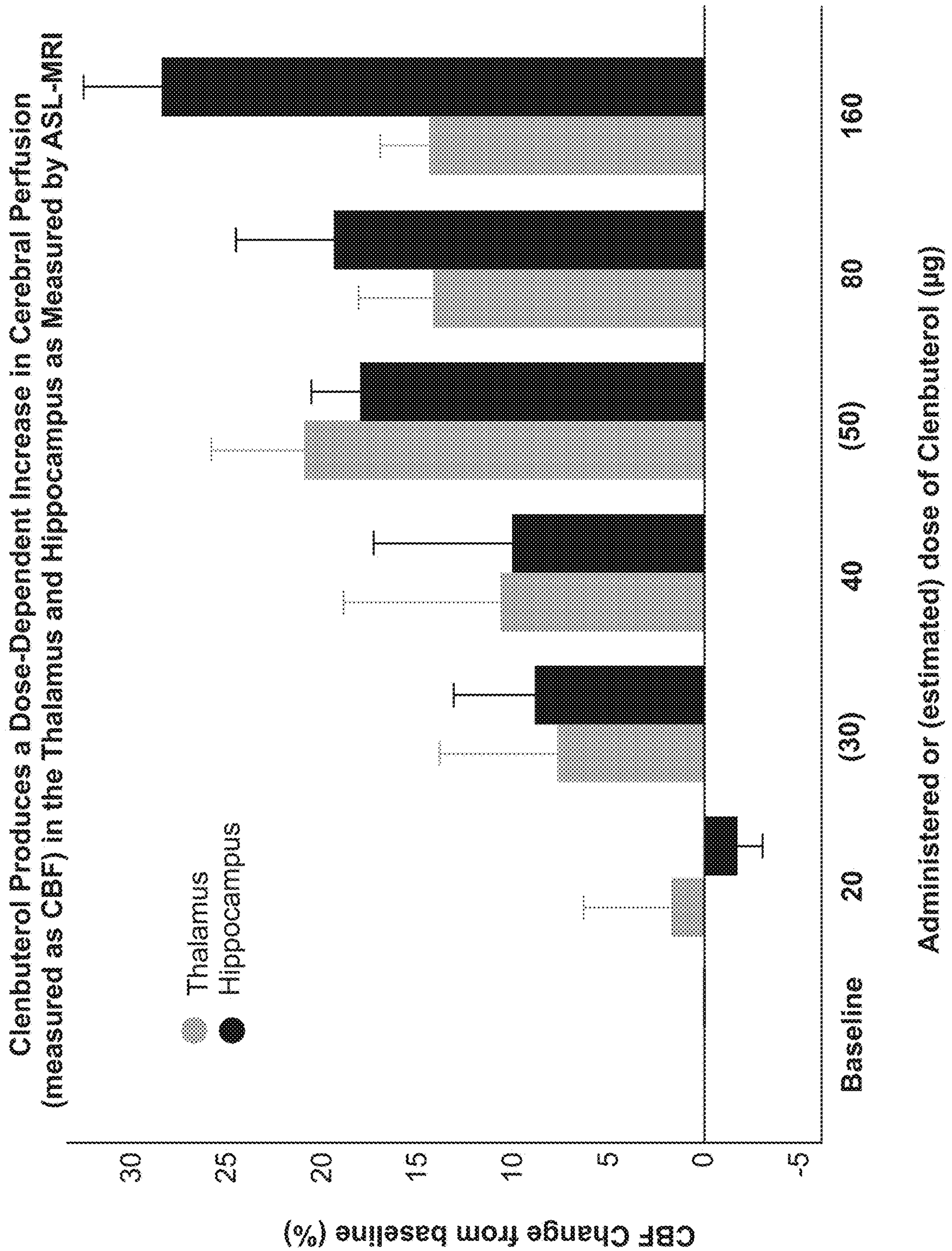
FIG. 8 shows that in a cohort 5 of the study, "estimated doses" of clenbuterol were based on dose equivalents calculated from PK modeling of exposures at 24 hours (estimated dose of 50 μg) and 48 hours (estimated dose of 30 μg) after a single dose of 80 μg clenbuterol administered to subjects on Day 1.

In a region of interest (ROI) analysis focusing on the hippocampus, which is well understood to be affected in neurodegenerative disorders, a single dose of 80 μg of clenbuterol causes a robust increase in perfusion (see FIG. 7). In this cohort of 6 healthy subjects treated with a single dose of 80 μg of clenbuterol every subject had an increase in hippocampal perfusion, which on average was 25%. The neuroimaging data from the study using ASL MRI demonstrated that doses of 80 and 160 μg of clenbuterol stimulate a robust, global increase in perfusion. In particular, areas of the brain thought to be relevant to the neuropathology of neurodegenerative disorders demonstrate significant improvements in perfusion in the range of 25% (FIGS. 6 and 7). An ROI analysis of the hippocampus in 6 healthy subjects aged 44 to 52 demonstrates a robust increase in this area of the brain for each subject FIG. 7. Taken together with other cohorts in which ASL MRI was conducted, a clear dose response relationship is seen between dose of clenbuterol and cerebral perfusion (FIG. 8). Doses below 30 μg do not produce significant cerebral perfusion increases as measured by CBF and a dose of 40 μg produces a minimal increase while doses of 80 and 160 μg produce global increases in cerebral perfusion, with particularly robust increases of 20% to 25% in areas of the brain relevant to neurodegenerative disorders such as the hippocampus and the thalamus (FIG. 8, Bartsch 2015, Leh 2016). Our hypothesis is that by improving cerebral perfusion, particularly in areas of the brain that are relevant for symptoms that are commonly found in neurodegenerative diseases such as PD and AD, the administration of a $\beta_2$-AR agonist will have a positive effect on clinically relevant symptoms such as memory and cognition. In particular for cognition, preliminary data from the study suggest that a single dose of 160 μg of clenbuterol improves cognition in healthy subjects as measured by adaptive tracking and word recall.

Example 4

Clinical Effectiveness

Figure 9:
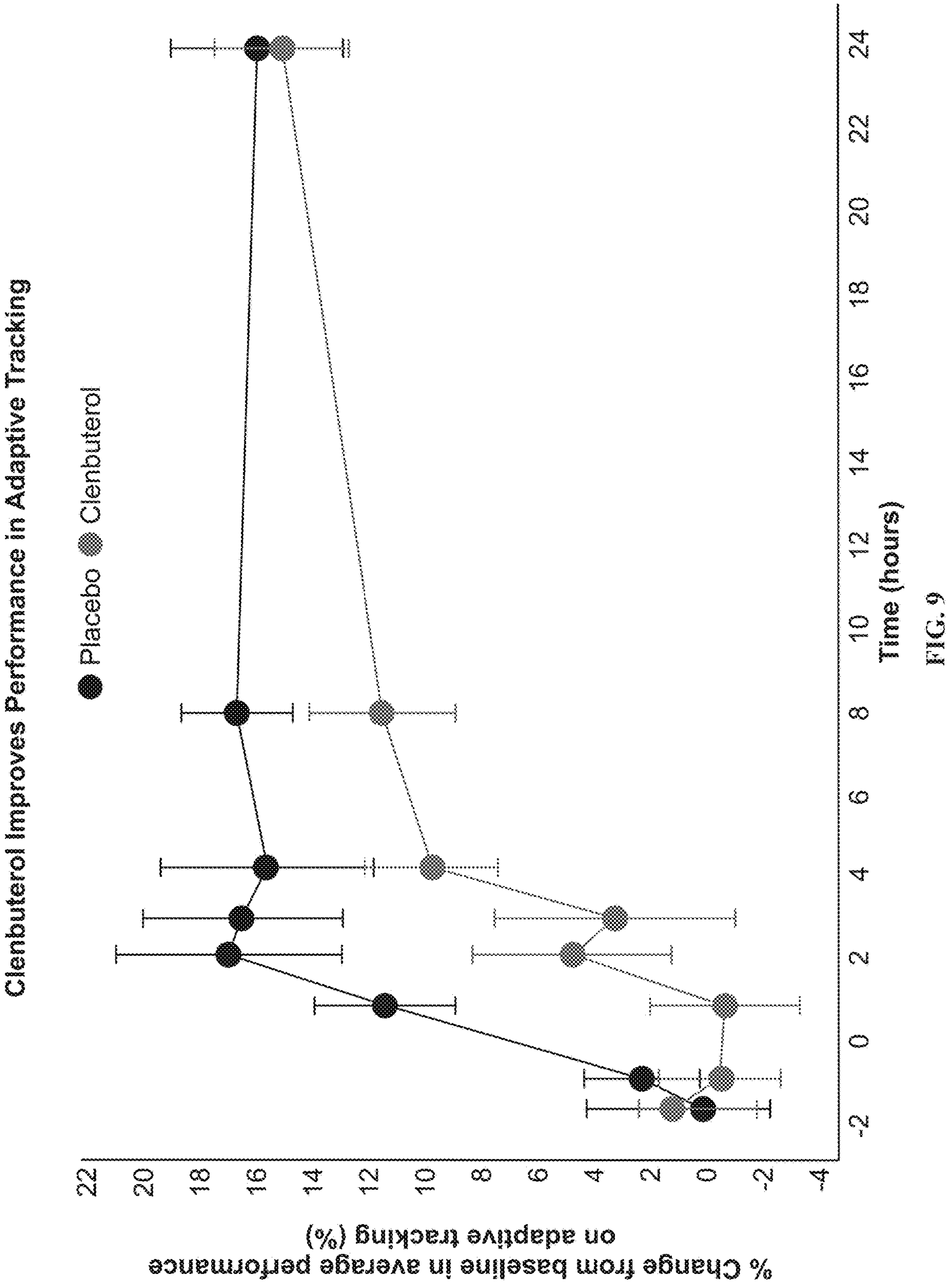
FIG. 9 shows improved adaptive tracking in response to clenbuterol.

Adaptive tracking measures visuomotor coordination and vigilance. In this test, the subject uses a joystick to move a small dot so that it stays within a continuously moving circle on a computer screen (Boland 1984). During the test, the speed of the circle is adjusted in response to the subject's ability to keep the dot in the circle, ensuring that the test is adapted to the individual subject. Results suggest that after a single dose of 160 μg clenbuterol performance in adaptive tracking improves as measured by the percent time that the subject is able to keep the small dot within the moving circle (see FIG. 9). The improvement shown by subjects is in the same range as that seen with subjects treated with the acetylcholinesterase inhibitor donepezil, which is in clinical use for the treatment of mild to moderate AD (Groeneveld 2016).

Figure 10:
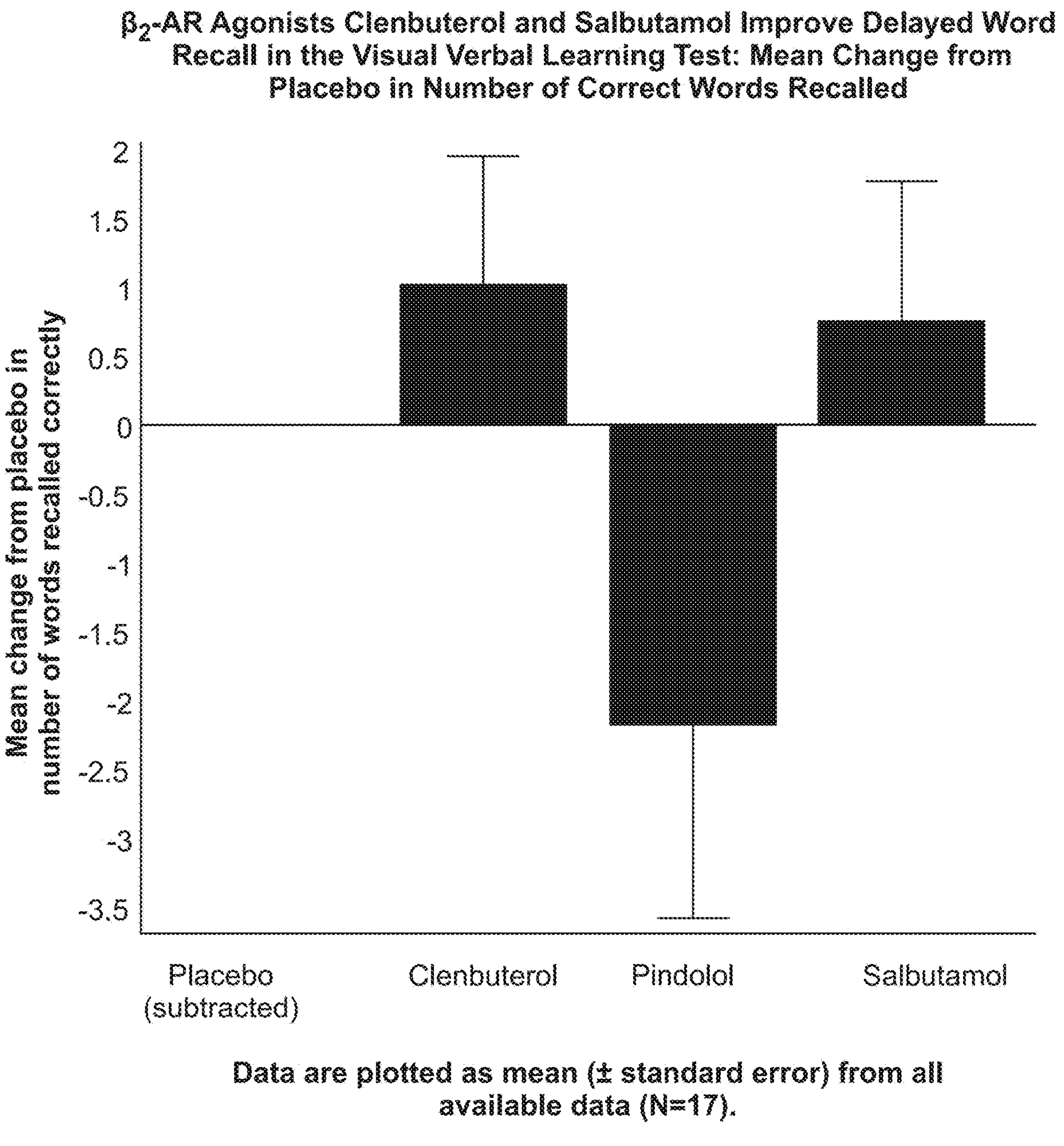
FIG. 10 shows effects of clenbuterol and a $\beta_2$-AR antagonist/$\beta_1$-AR partial agonist on the visual verbal learning test (VVLT).

The visual verbal learning test (VVLT) is a test for learning and memory (de Haas 2009). Subjects are presented 30 words on a screen, one at a time, for 1 second with a 1-second interval between words over a total of 1 minute. This is repeated in 3 trials. After each trial, subjects are asked to recall as many words as they can. After the third trial, there is a delay of 2.5 hours and subjects are then tested once for delayed recall. Clenbuterol improved performance in VVLT in both the immediate recall (Trial 1, not shown) and the delayed recall (see FIG. 10). The effect for clenbuterol is an improvement in approximately 1.5 to 2 correctly recalled words, which is clinically meaningful. Since this was a crossover study, everyone who completed Part A was dosed with the 3 agents plus placebo. Interestingly, both of the $\beta_2$-AR agonists tested in this study, clenbuterol and salbutamol, had positive effects on the VVLT. In contrast, the $\beta_2$-AR antagonist/$\beta_1$-AR partial agonist pindolol had a detrimental effect on this learning and memory test.

Aspects and Embodiments of the Disclosure

In one aspect, the disclosure provides a method that includes: administering to said patient a $\beta_2$-AR agonist and a peripherally acting β-blocker (PABRA), wherein the peripherally acting β-blocker (PABRA) is administered in a dose of about 15 mg or less. The method can further include subjecting a patient to brain imaging to determine cognitive function and/or to identify whether said patient is in need of or desiring improvement of cognitive function and/or treatment of a neurodegenerative disease, and/or identifying a particular type of neurodegenerative disease based on a spatial pattern of the brain imaging result.

In another aspect, the disclosure provides a method including: administering to said patient a $\beta_2$-AR agonist and a peripherally acting β-blocker (PABRA) to improve cognition and/or treat a neurodegenerative disease in said patient, wherein the peripherally acting β-blocker (PABRA) is administered in a dose of about 15 mg or less. The method can further include subjecting a patient to brain imaging to determine cognitive function to identify whether said patient is in need of or desiring improvement of cognitive function and/or treatment of a neurodegenerative disease, identifying a particular type of neurodegenerative disease based on a spatial pattern of the brain imaging result, and/or subsequently re-subjecting said patient to brain imaging to determine any improvement in cognitive function and/or treatment of said neurodegenerative disease.

In yet another aspect, the disclosure provides a method including: subjecting a patient to brain imaging to determine cognitive function in said patient; identifying a particular type of neurodegenerative disease based on a spatial pattern of the brain imaging result; administering to said patient a $\beta_2$-AR agonist and a peripherally acting β-blocker (PABRA), wherein the peripherally acting β-blocker (PABRA) is administered in a dose of about 15 mg or less; and subsequently re-subjecting said patient to brain imaging to determine any improvement in cognitive function.

In still another aspect, the disclosure provides a method including: administering to said patient a $\beta_2$-AR agonist and a peripherally acting β-blocker (PABRA), wherein the peripherally acting β-blocker (PABRA) is administered in a dose of about 15 mg or less. The method can further include subjecting a patient to brain imaging to determine cognitive function and/or to identify whether said patient is in need of or desiring improvement of cognitive function and/or treatment of a neurodegenerative disease, and/or identifying a particular type of neurodegenerative disease based on a spatial pattern of the brain imaging result.

In another aspect, the disclosure provides a method including: administering to said patient a $\beta_2$-AR agonist and a peripherally acting β-blocker (PABRA) to improve cognition and/or treat a neurodegenerative disease in said patient, wherein the peripherally acting β-blocker (PABRA) is administered in a dose of about 15 mg or less. The method can further include subjecting a patient to brain imaging to determine cognitive function and/or to identify whether said patient is in need of or desiring improvement of cognitive function and/or treatment of a neurodegenerative disease, identifying a particular type of neurodegenerative disease based on a spatial pattern of the brain imaging result; and/or subsequently re-subjecting said patient to brain imaging to determine any improvement in cognitive function and/or treatment of said neurodegenerative disease.

In another aspect, the disclosure provides a method including: subjecting a patient to brain imaging to determine cognitive function in said patient; identifying a particular type of neurodegenerative disease based on a spatial pattern of the brain imaging result; administering to said patient a $\beta_2$-AR agonist and a peripherally acting β-blocker (PABRA), wherein the peripherally acting β-blocker (PABRA) is administered in a dose of about 15 mg or less; and subsequently re-subjecting said patient to brain imaging to determine any improvement in cognitive function.

In another aspect, the disclosure provides a method including: administering to said patient clenbuterol and a peripherally acting β-blocker (PABRA), wherein the peripherally acting β-blocker (PABRA) is administered in a dose of about 15 mg or less. The method can further include subjecting a patient to brain imaging to determine cognitive function and/or to identify whether said patient is in need of or desiring improvement of cognitive function and/or treatment of a neurodegenerative disease, and/or identifying a particular type of neurodegenerative disease based on a spatial pattern of the brain imaging result.

In another aspect, the disclosure provides a method including: administering to said patient clenbuterol and a peripherally acting β-blocker (PABRA) to improve cognition and/or treat a neurodegenerative disease in said patient, wherein the peripherally acting β-blocker (PABRA) is administered in a dose of about 15 mg or less. The method can further include subjecting a patient to brain imaging to determine cognitive function and/or to identify whether said patient is in need of or desiring improvement of cognitive function and/or treatment of a neurodegenerative disease, identifying a particular type of neurodegenerative disease based on a spatial pattern of the brain imaging result, and subsequently re-subjecting said patient to brain imaging to determine any improvement in cognitive function and/or treatment of said neurodegenerative disease.

In another aspect, the disclosure provides a method including: subjecting a patient to brain imaging to determine cognitive function in said patient; identifying a particular type of neurodegenerative disease based on a spatial pattern of the brain imaging result; administering to said patient clenbuterol and a peripherally acting β-blocker (PABRA), wherein the peripherally acting β-blocker (PABRA) is administered in a dose of about 15 mg or less; and subsequently re-subjecting said patient to brain imaging to determine any improvement in cognitive function.

In another aspect, the disclosure provides a method including: administering to said patient tulobuterol and a peripherally acting β-blocker (PABRA), wherein the peripherally acting β-blocker (PABRA) is administered in a dose of about 15 mg or less. The method can further include subjecting a patient to brain imaging to determine cognitive function and/or to identify whether said patient is in need of or desiring improvement of cognitive function and/or treatment of a neurodegenerative disease, and/or identifying a particular type of neurodegenerative disease based on a spatial pattern of the brain imaging result; and subsequently administering to said patient tulobuterol and a peripherally acting β-blocker (PABRA).

In another aspect, the disclosure provides a method including: administering to said patient tulobuterol and a peripherally acting β-blocker (PABRA) to improve cognition and/or treat a neurodegenerative disease in said patient, wherein the peripherally acting β-blocker (PABRA) is administered in a dose of about 15 mg or less. The method can further include subjecting a patient to brain imaging to determine cognitive function and/or to identify whether said patient is in need of or desiring improvement of cognitive function and/or treatment of a neurodegenerative disease, identifying a particular type of neurodegenerative disease based on a spatial pattern of the brain imaging result and/or subsequently re-subjecting said patient to brain imaging to determine any improvement in cognitive function and/or treatment of said neurodegenerative disease.

In another aspect, the disclosure provides a method including: subjecting a patient to brain imaging to determine cognitive function in said patient; identifying a particular type of neurodegenerative disease based on a spatial pattern of the brain imaging result; administering to said patient tulobuterol and a peripherally acting β-blocker (PABRA), wherein the peripherally acting β-blocker (PABRA) is administered in a dose of about 15 mg or less; and subsequently re-subjecting said patient to brain imaging to determine any improvement in cognitive function.

In another aspect, the disclosure provides a method including treating a subject identified as having diminished cognitive function and/or being in need of or desiring improvement of cognitive function and/or treatment of a neurodegenerative disease by administering the subject a pharmaceutical composition including a $\beta_1$-AR agonist, a $\beta_2$-AR agonist, a peripherally acting β-blocker (PABRA), or any combination thereof, wherein the peripherally acting β-blocker (PABRA) is administered in a dose of about 15 mg or less. In some embodiments, the method further includes assessing effectiveness of the treatment, the treatment can be assessed by subjecting the subject to a test to assess improved cognitive function or amelioration of the neurodegenerative disease. In some embodiments, the method further includes adjusting administration of the pharmaceutical composition by adjusting dosage of the pharmaceutical composition and/or timing of administration of the pharmaceutical composition.

In one aspect, the disclosure provides a method that includes: administering to said patient a $\beta_2$-AR agonist and a peripherally acting β-blocker (PABRA), wherein the peripherally acting β-blocker (PABRA) is administered in a sub-therapeutic dose. The method can further include subjecting a patient to brain imaging to determine cognitive function and/or to identify whether said patient is in need of or desiring improvement of cognitive function and/or treatment of a neurodegenerative disease, and/or identifying a particular type of neurodegenerative disease based on a spatial pattern of the brain imaging result.

In another aspect, the disclosure provides a method including: administering to said patient a $\beta_2$-AR agonist and a peripherally acting β-blocker (PABRA) to improve cognition and/or treat a neurodegenerative disease in said patient, wherein the peripherally acting β-blocker (PABRA) is administered in a sub-therapeutic dose. The method can further include subjecting a patient to brain imaging to determine cognitive function to identify whether said patient is in need of or desiring improvement of cognitive function and/or treatment of a neurodegenerative disease, identifying a particular type of neurodegenerative disease based on a spatial pattern of the brain imaging result, and/or subsequently re-subjecting said patient to brain imaging to determine any improvement in cognitive function and/or treatment of said neurodegenerative disease.

In yet another aspect, the disclosure provides a method including: subjecting a patient to brain imaging to determine cognitive function in said patient; identifying a particular type of neurodegenerative disease based on a spatial pattern of the brain imaging result; administering to said patient a $\beta_2$-AR agonist and a peripherally acting β-blocker (PABRA), wherein the peripherally acting β-blocker (PABRA) is administered in a sub-therapeutic dose; and subsequently re-subjecting said patient to brain imaging to determine any improvement in cognitive function.

In still another aspect, the disclosure provides a method including: administering to said patient a $\beta_2$-AR agonist and a peripherally acting β-blocker (PABRA), wherein the peripherally acting β-blocker (PABRA) is administered in a sub-therapeutic dose. The method can further include subjecting a patient to brain imaging to determine cognitive function and/or to identify whether said patient is in need of or desiring improvement of cognitive function and/or treatment of a neurodegenerative disease, and/or identifying a particular type of neurodegenerative disease based on a spatial pattern of the brain imaging result.

In another aspect, the disclosure provides a method including: administering to said patient a $\beta_2$-AR agonist and a peripherally acting β-blocker (PABRA) to improve cognition and/or treat a neurodegenerative disease in said patient, wherein the peripherally acting β-blocker (PABRA) is administered in a a sub-therapeutic dose. The method can further include subjecting a patient to brain imaging to determine cognitive function and/or to identify whether said patient is in need of or desiring improvement of cognitive function and/or treatment of a neurodegenerative disease, identifying a particular type of neurodegenerative disease based on a spatial pattern of the brain imaging result; and/or subsequently re-subjecting said patient to brain imaging to determine any improvement in cognitive function and/or treatment of said neurodegenerative disease.

In another aspect, the disclosure provides a method including: subjecting a patient to brain imaging to determine cognitive function in said patient; identifying a particular type of neurodegenerative disease based on a spatial pattern of the brain imaging result; administering to said patient a $\beta_2$-AR agonist and a peripherally acting β-blocker (PABRA), wherein the peripherally acting β-blocker (PABRA) is administered in a a sub-therapeutic dose; and subsequently re-subjecting said patient to brain imaging to determine any improvement in cognitive function.

In another aspect, the disclosure provides a method including: administering to said patient clenbuterol and a peripherally acting β-blocker (PABRA), wherein the peripherally acting β-blocker (PABRA) is administered in a sub-therapeutic dose. The method can further include subjecting a patient to brain imaging to determine cognitive function and/or to identify whether said patient is in need of or desiring improvement of cognitive function and/or treatment of a neurodegenerative disease, and/or identifying a particular type of neurodegenerative disease based on a spatial pattern of the brain imaging result.

In another aspect, the disclosure provides a method including: administering to said patient clenbuterol and a peripherally acting β-blocker (PABRA) to improve cognition and/or treat a neurodegenerative disease in said patient, wherein the peripherally acting β-blocker (PABRA) is administered in a sub-therapeutic dose. The method can further include subjecting a patient to brain imaging to determine cognitive function and/or to identify whether said patient is in need of or desiring improvement of cognitive function and/or treatment of a neurodegenerative disease, identifying a particular type of neurodegenerative disease based on a spatial pattern of the brain imaging result, and subsequently re-subjecting said patient to brain imaging to determine any improvement in cognitive function and/or treatment of said neurodegenerative disease.

In another aspect, the disclosure provides a method including: subjecting a patient to brain imaging to determine cognitive function in said patient; identifying a particular type of neurodegenerative disease based on a spatial pattern of the brain imaging result; administering to said patient clenbuterol and a peripherally acting β-blocker (PABRA), wherein the peripherally acting β-blocker (PABRA) is administered a sub-therapeutic dose; and subsequently re-subjecting said patient to brain imaging to determine any improvement in cognitive function.

In another aspect, the disclosure provides a method including: administering to said patient tulobuterol and a peripherally acting β-blocker (PABRA), wherein the peripherally acting β-blocker (PABRA) is administered in a sub-therapeutic dose. The method can further include subjecting a patient to brain imaging to determine cognitive function and/or to identify whether said patient is in need of or desiring improvement of cognitive function and/or treatment of a neurodegenerative disease, and/or identifying a particular type of neurodegenerative disease based on a spatial pattern of the brain imaging result; and subsequently administering to said patient tulobuterol and a peripherally acting β-blocker (PABRA).

In another aspect, the disclosure provides a method including: administering to said patient tulobuterol and a peripherally acting β-blocker (PABRA) to improve cognition and/or treat a neurodegenerative disease in said patient, wherein the peripherally acting β-blocker (PABRA) is administered in a sub-therapeutic dose. The method can further include subjecting a patient to brain imaging to determine cognitive function and/or to identify whether said patient is in need of or desiring improvement of cognitive function and/or treatment of a neurodegenerative disease, identifying a particular type of neurodegenerative disease based on a spatial pattern of the brain imaging result and/or subsequently re-subjecting said patient to brain imaging to determine any improvement in cognitive function and/or treatment of said neurodegenerative disease.

In another aspect, the disclosure provides a method including: subjecting a patient to brain imaging to determine cognitive function in said patient; identifying a particular type of neurodegenerative disease based on a spatial pattern of the brain imaging result; administering to said patient tulobuterol and a peripherally acting β-blocker (PABRA), wherein the peripherally acting β-blocker (PABRA) is administered in a sub-therapeutic dose; and subsequently re-subjecting said patient to brain imaging to determine any improvement in cognitive function.

In another aspect, the disclosure provides a method including treating a subject identified as having diminished cognitive function and/or being in need of or desiring improvement of cognitive function and/or treatment of a neurodegenerative disease by administering the subject a pharmaceutical composition including a $\beta_1$-AR agonist, a $\beta_2$-AR agonist, a peripherally acting β-blocker (PABRA), or any combination thereof, wherein the peripherally acting β-blocker (PABRA) is administered in a sub-therapeutic dose. In some embodiments, the method further includes assessing effectiveness of the treatment, the treatment can be assessed by subjecting the subject to a test to assess improved cognitive function or amelioration of the neurodegenerative disease. In some embodiments, the method further includes adjusting administration of the pharmaceutical composition by adjusting dosage of the pharmaceutical composition and/or timing of administration of the pharmaceutical composition.

In embodiments of any aspect or embodiment of the disclosure described herein, the brain imaging is fluorodeoxyglucose positron emission tomography (FDG-PET) scan, magnetic resonance imaging-arterial spin labeling (MRI-ASL), or magnetic resonance imaging-blood oxygenation level dependent computerized tomography (MRI-BOLD).

In embodiments of any aspect or embodiment of the disclosure described herein, said $\beta_2$-AR agonist is administered at a dose of from about 30 to 160 μg.

In embodiments of any aspect or embodiment of the disclosure described herein, said $\beta_2$-AR agonist is administered at a dose of from about 50 to 160 μg.

In embodiments of any aspect or embodiment of the disclosure described herein, said $\beta_2$-AR agonist is administered at a dose of from about 30 to 160 μg, 50 to 160 μg, 80 to 160 μg, 100 to 160 μg, 120 to 160 μg, 140 to 160 μg, 30 to 140 μg, 50 to 140 μg, 80 to 140 μg, 100 to 140 μg, 120 to 140 μg, 30 to 120 μg, 50 to 120 μg, 80 to 120 μg, 100 to 120 μg, 30 to 100 μg, 50 to 100 μg, 80 to 100 μg, 30 to 80 μg, 50 to 80 μg, 30 to 50 μg, 30 μg, 40 μg, 50 μg, 60 μg, 70 μg, 80 μg, 90 μg, 100 μg, 110 μg, 120 μg, 130 μg, 140 μg, 150 μg, or 160 μg.

In embodiments of any aspect or embodiment of the disclosure described herein, said $\beta_2$-AR agonist is administered at a dose of from about 0.5-20 mg; or 1-10 mg; or 2-8 mg; or about 1 mg; or about 2 mg; or about 3 mg; or about 4 mg; or about 5 mg; or about 6 mg; or about 7 mg; or about 8 mg; or about 10 mg.

In embodiments of any aspect or embodiment of the disclosure described herein, the above-mentioned dose is a total daily dose of $\beta_2$-AR agonist and is administered daily for a period of weeks or more.

In embodiments of any aspect or embodiment of the disclosure described herein, the above-mentioned dose is a total weekly dose of $\beta_2$-AR agonist and is administered weekly for a period of weeks or more.

In embodiments of any aspect or embodiment of the disclosure described herein, said $\beta_2$-AR agonist is one or more selected from the group consisting of tulobuterol, mabuterol, ritodrine, salmeterol, bambuterol, formoterol and clenbuterol.

In embodiments of any aspect or embodiment of the disclosure described herein, said $\beta_2$-AR agonist is clenbuterol.

In embodiments of any aspect or embodiment of the disclosure described herein, said $\beta_2$-AR agonist is tulobuterol.

In embodiments of any aspect or embodiment of the disclosure described herein, said peripherally acting β-blocker (PABRA) is nadolol.

In embodiments of any aspect or embodiment of the disclosure described herein, nadolol is a mixture of four diastereomers.

In embodiments of any aspect or embodiment of the disclosure described herein, the nadolol administered is a specific enantiomerically pure isomer.

In embodiments of any aspect or embodiment of the disclosure described herein, said peripherally acting β-blocker (PABRA) is administered at a dose of from about 0.1 mg to 15 mg.

In embodiments of any aspect or embodiment of the disclosure described herein, said peripherally acting β-blocker (PABRA) is administered at a dose of from about 0.1 to 15 mg, 0.1-10 mg, 0.1 to 1 mg, 0.1 to 5 mg, 1 to 15 mg, 1 to 10 mg, 1 to 5 mg, 5 to 10 mg, 10 mg or less, 7 mg or less, 5 mg or less, 1 mg or less, 0.1 mg, 0.5 mg, 1 mg, 2 mg, 3 mg, 4 mg, 5 mg, 6 mg, 7 mg, 8 mg, 9 mg, or 10 mg.

In embodiments of any aspect or embodiment of the disclosure described herein, the above-mentioned dose is a total daily dose of said peripherally acting β-blocker (PABRA) and is administered daily for a period of weeks or more.

In embodiments of any aspect or embodiment of the disclosure described herein, said $\beta_1$-AR agonist, $\beta_2$-AR agonist and/or peripherally acting β-blocker (PABRA) are each administered orally.

In embodiments of any aspect or embodiment of the disclosure described herein, said $\beta_2$-AR agonist and peripherally acting β-blocker (PABRA) are each administered orally and both agents are present in a tablet.

In embodiments of any aspect or embodiment of the disclosure described herein, clenbuterol and nadolol are each administered orally and both agents are present in a tablet.

In embodiments of any aspect or embodiment of the disclosure described herein, the tablet includes clenbuterol in an amount from about 30 to 160 μg and nadolol in an amount from about 15 mg or less.

In embodiments of any aspect or embodiment of the disclosure described herein, nadolol is provided in an amount from about 0.1 to 15 mg, 0.1 to 10 mg, 0.1 to 1 mg, 0.1 to 5 mg, 1 to 15 mg, 1 to 10 mg, 1 to 5 mg, 5 to 10 mg, 10 mg or less, 7 mg or less, 5 mg or less, 1 mg or less, 0.1 mg, 0.5 mg, 1 mg, 2 mg, 3 mg, 4 mg, 5 mg, 6 mg, 7 mg, 8 mg, 9 mg, or 10 mg.

In embodiments of any aspect or embodiment of the disclosure described herein, the above-mentioned doses of clenbuterol and nadolol are a total daily dose and is administered daily for a period of weeks or more.

In embodiments of any aspect or embodiment of the disclosure described herein, the above-mentioned doses of clenbuterol and nadolol are a weekly dose and is administered weekly for a period of weeks or more.

In embodiments of any aspect or embodiment of the disclosure described herein, tulobuterol and nadolol are each administered orally and both agents are present in a tablet.

In embodiments of any aspect or embodiment of the disclosure described herein, the tablet includes tulobuterol in an amount that is 0.5-20 mg; or 1-10 mg; or 2-8 mg; or about 1 mg; or about 2 mg; or about 3 mg; or about 4 mg; or about 5 mg; or about 6 mg; or about 7 mg; or about 8 mg; or about 10 mg; and nadolol in an amount from about 15 mg or less.

In embodiments of any aspect or embodiment of the disclosure described herein, nadolol is provided in an amount from about 0.1 to 15 mg, 0.1 to 10 mg, 0.1 to 1 mg, 0.1 to 5 mg, 1 to 15 mg, 1 to 10 mg, 1 to 5 mg, 5 to 10 mg, 10 mg or less, 7 mg or less, 5 mg or less, 1 mg or less, 0.1 mg, 0.5 mg, 1 mg, 2 mg, 3 mg, 4 mg, 5 mg, 6 mg, 7 mg, 8 mg, 9 mg, or 10 mg.

In embodiments of any aspect or embodiment of the disclosure described herein, the above-mentioned doses of tulobuterol and nadolol are a total daily dose and is administered daily for a period of weeks or more.

In embodiments of any aspect or embodiment of the disclosure described herein, the above-mentioned doses of tulobuterol and nadolol are a weekly dose and is administered weekly for a period of weeks or more.

In embodiments of any aspect or embodiment of the disclosure described herein, said neurodegenerative disease is one or more selected from MCI, aMCI, Vascular Dementia, Mixed Dementia, FTD (fronto-temporal dementia; Pick's disease), HD (Huntington disease), Rett Syndrome, PSP (progressive supranuclear palsy), CBD (corticobasal degeneration), SCA (spinocerebellar ataxia), MSA (Multiple system atrophy), SDS (Shy-Drager syndrome), olivopontocerebellar atrophy, TBI (traumatic brain injury), CTE (chronic traumatic encephalopathy), stroke, WKS (Wernicke-Korsakoff syndrome; alcoholic dementia & thiamine deficiency), normal pressure hydrocephalus, hypersomnia/narcolepsy, ASD (autistic spectrum disorders), FXS (fragile X syndrome), TSC (tuberous sclerosis complex), prion-related diseases (CJD etc.), depressive disorders, DLB (dementia with Lewy bodies), PD (Parkinson's disease), PDD (PD dementia), ADHD (attention deficit hyperactivity disorder), and Down Syndrome.

In embodiments of any aspect or embodiment of the disclosure described herein, said neurodegenerative disease is one or more selected from MCI, aMCI, Vascular Dementia, Mixed Dementia, FTD (fronto-temporal dementia; Pick's disease), HD (Huntington disease), Rett Syndrome, PSP (progressive supranuclear palsy), CBD (corticobasal degeneration), SCA (spinocerebellar ataxia), MSA (Multiple system atrophy), SDS (Shy-Drager syndrome), olivopontocerebellar atrophy, TBI (traumatic brain injury), CTE (chronic traumatic encephalopathy), stroke, WKS (Wernicke-Korsakoff syndrome; alcoholic dementia & thiamine deficiency), normal pressure hydrocephalus, hypersomnia/narcolepsy, ASD (autistic spectrum disorders), FXS (fragile X syndrome), TSC (tuberous sclerosis complex), prion-related diseases (CJD etc.), depressive disorders, DLB (dementia with Lewy bodies), PD (Parkinson's disease), PDD (PD dementia), and ADHD (attention deficit hyperactivity disorder).

In embodiments of any aspect or embodiment of the disclosure described herein, said patient does not have Alzheimer's disease.

In embodiments of any aspect or embodiment of the disclosure described herein, said patient does not have Down Syndrome.

In embodiments of any aspect or embodiment of the disclosure described herein, said patient does not have Parkinson's disease.

In embodiments of any aspect or embodiment of the disclosure described herein, said patient does not have dementia with Lewy bodies.

In embodiments of any aspect or embodiment of the disclosure described herein, said tulobuterol is (S)-tulobuterol that is substantially free of (R)-tulobuterol.

In embodiments of any aspect or embodiment of the disclosure described herein, said tulobuterol is (R)-tulobuterol that is substantially free of (S)-tulobuterol.

In embodiments of any aspect or embodiment of the disclosure described herein, a pharmaceutical tablet is provided, comprising: a $\beta_2$-AR agonist in an amount from about 30 to 160 μg, and a peripherally acting β-blocker (PABRA) in an amount from about 15 mg or less.

In embodiments of any aspect or embodiment of the disclosure described herein, the $\beta_2$-AR agonist is in an amount from about 50 to 160 μg.

In embodiments of any aspect or embodiment of the disclosure described herein, the β2-AR agonist is in an amount from about 80 to 160 μg.

In embodiments of any aspect or embodiment of the disclosure described herein, said β2-AR agonist is administered at a dose of from about 30 to 160 μg, 50 to 160 μg, 80 to 160 μg, 100 to 160 μg, 120 to 160 μg, 140 to 160 μg, 30 to 140 μg, 50 to 140 μg, 80 to 140 μg, 100 to 140 μg, 120 to 140 μg, 30 to 120 μg, 50 to 120 μg, 80 to 120 μg, 100 to 120 μg, 30 to 100 μg, 50 to 100 μg, 80 to 100 μg, 30 to 80 μg, 50 to 80 μg, 30 to 50 μg, 30 μg, 40 μg, 50 μg, 60 μg, 70 μg, 80 μg, 90 μg, 100 μg, 110 μg, 120 μg, 130 μg, 140 μg, 150 μg, or 160 μg.

In embodiments of any aspect or embodiment of the disclosure described herein, the above-mentioned dose of β2-AR agonist is a total daily dose and is administered daily for a period of weeks or more.

In embodiments of any aspect or embodiment of the disclosure described herein, the above-mentioned dose of β2-AR agonist is a weekly and is administered weekly for a period of two weeks or more.

In embodiments of any aspect or embodiment of the disclosure described herein, the peripherally acting β-blocker (PABRA) is provided in an amount from about 0.1 to 15 mg, 0.1 to 10 mg, 0.1 to 1 mg, 0.1 to 5 mg, 1 to 15 mg, 1 to 10 mg, 1 to 5 mg, 5 to 10 mg, 10 mg or less, 7 mg or less, 5 mg or less, 1 mg or less, 0.1 mg, 0.5 mg, 1 mg, 2 mg, 3 mg, 4 mg, 5 mg, 6 mg, 7 mg, 8 mg, 9 mg, or 10 mg.

In embodiments of any aspect or embodiment of the disclosure described herein, the peripherally acting β-blocker (PABRA) is provided in an amount from about 0.1 to 15 mg.

In embodiments of any aspect or embodiment of the disclosure described herein, the peripherally acting β-blocker (PABRA) is provided in an amount from about 5 to 10 mg.

In embodiments of any aspect or embodiment of the disclosure described herein, the above-mentioned dose of the peripherally acting β-blocker (PABRA) is a total daily dose and is administered daily for a period of weeks or more.

In embodiments of any aspect or embodiment of the disclosure described herein, the above-mentioned dose of the peripherally acting β-blocker (PABRA) is a weekly dose and is administered weekly for a period of weeks or more.

In embodiments of any aspect or embodiment of the disclosure described herein, the β2-AR agonist is clenbuterol.

In embodiments of any aspect or embodiment of the disclosure described herein, the $\beta_2$-AR agonist is tulobuterol.

In embodiments of any aspect or embodiment of the disclosure described herein, the peripherally acting β-blocker (PABRA) is nadolol.

In embodiments of any aspect or embodiment of the disclosure described herein, nadolol is a mixture of four diastereomers.

In embodiments of any aspect or embodiment of the disclosure described herein, the nadolol administered is a specific enantiomerically pure isomer.

In embodiments of any aspect or embodiment of the disclosure described herein, a joint formulation is provided, comprising: a β2-AR agonist in an amount from about 30 to 160 μg, and a peripherally acting β-blocker (PABRA) in an amount from 15 mg or less.

In embodiments of any aspect or embodiment of the disclosure described herein, the β2-AR agonist is in an amount from about 50 to 160 μg.

In embodiments of any aspect or embodiment of the disclosure described herein, the β2-AR agonist is in an amount from about 80 to 160 μg.

In embodiments of any aspect or embodiment of the disclosure described herein, the β2-AR agonist is in an amount from about 0.5 to 20 mg.

In embodiments of any aspect or embodiment of the disclosure described herein, the β2-AR agonist is in an amount from about 2 to 8 mg.

In embodiments of any aspect or embodiment of the disclosure described herein, the above-mentioned dose of β2-AR agonist is a total daily dose and is administered daily for a period of weeks or more.

In embodiments of any aspect or embodiment of the disclosure described herein, the above-mentioned dose of β2-AR agonist is a weekly dose and is administered weekly for a period of two weeks or more.

In embodiments of any aspect or embodiment of the disclosure described herein, the peripherally acting β-blocker (PABRA) is in an amount from about 0.1 to 15 mg.

In embodiments of any aspect or embodiment of the disclosure described herein, the peripherally acting β-blocker (PABRA) is in an amount from about 5 to 10 mg.

In embodiments of any aspect or embodiment of the disclosure described herein, the above-mentioned dose of the peripherally acting β-blocker (PABRA) is a total daily dose and is administered daily for a period of weeks or more.

In embodiments of any aspect or embodiment of the disclosure described herein, the β2-AR agonist is clenbuterol.

In embodiments of any aspect or embodiment of the disclosure described herein, the β2-AR agonist is tulobuterol.

In embodiments of any aspect or embodiment of the disclosure described herein, the peripherally acting β-blocker (PABRA) is nadolol.

In embodiments of any aspect or embodiment of the disclosure described herein, nadolol is a mixture of four diastereomers.

In embodiments of any aspect or embodiment of the disclosure described herein, the nadolol administered is a specific enantiomerically pure isomer.

In embodiments of any aspect or embodiment of the disclosure described herein, a single formulation is provided, comprising: a β2-AR agonist in an amount from about 30 to 160 μg, and a peripherally acting β-blocker (PABRA) in an amount from 15 mg or less.

In embodiments of any aspect or embodiment of the disclosure described herein, the β2-AR agonist is in an amount from about 50 to 160 μg.

In embodiments of any aspect or embodiment of the disclosure described herein, the β2-AR agonist is in an amount from about 80 to 160 μg.

In embodiments of any aspect or embodiment of the disclosure described herein, the above-mentioned dose of β2-AR agonist is a total daily dose and is administered daily for a period of weeks or more.

In embodiments of any aspect or embodiment of the disclosure described herein, the peripherally acting β-blocker (PABRA) is in an amount from about 0.1 to 15 mg.

In embodiments of any aspect or embodiment of the disclosure described herein, the peripherally acting β-blocker (PABRA) is in an amount from about 5 to 10 mg.

In embodiments of any aspect or embodiment of the disclosure described herein, the above-mentioned dose of the peripherally acting β-blocker (PABRA) is a total daily dose and is administered daily for a period of weeks or more.

In embodiments of any aspect or embodiment of the disclosure described herein, the β2-AR agonist is clenbuterol.

In embodiments of any aspect or embodiment of the disclosure described herein, the β2-AR agonist is tulobuterol.

In embodiments of any aspect or embodiment of the disclosure described herein, the peripherally acting β-blocker (PABRA) is nadolol.

In embodiments of any aspect or embodiment of the disclosure described herein, nadolol is a mixture of four diastereomers.

In embodiments of any aspect or embodiment of the disclosure described herein, the nadolol administered is a specific enantiomerically pure isomer.

While the disclosure has been particularly shown and described with reference to specific embodiments (some of which are preferred embodiments), it should be understood by those having skill in the art that various changes in form and detail may be made therein without departing from the spirit and scope of the present disclosure as disclosed herein.

All references referred to in the present disclosure are hereby incorporated by reference in their entirety. Various embodiments of the present disclosure may be characterized by the potential claims listed in the paragraphs following this paragraph (and before the actual claims provided at the end of this application). These potential claims form a part of the written description of this application. Accordingly, subject matter of the following potential claims may be presented as actual claims in later proceedings involving this application or any application claiming priority based on this application. Inclusion of such potential claims should not be construed to mean that the actual claims do not cover the subject matter of the potential claims. Thus, a decision to not present these potential claims in later proceedings should not be construed as a donation of the subject matter to the public.

The embodiments of the disclosure described above are intended to be merely exemplary; numerous variations and modifications will be apparent to those skilled in the art. All such variations and modifications are intended to be within the scope of the present disclosure as defined in any appended claims.

What is claimed is:

1. A method comprising:

administering clenbuterol and nadolol to a patient, wherein clenbuterol is administered in a dose of about 40 μg or 80 μg, and nadolol is administered in a dose of about 0.1 mg to 10 mg.

2. The method of claim 1, wherein said nadolol is administered in a dose of 1 mg to 10 mg.

3. The method of claim 1, wherein said nadolol is administered in a dose of 1 mg to 5 mg.

4. The method of claim 1, wherein said nadolol is administered in a dose of about 2 mg.

5. The method of claim 1, wherein said nadolol is administered in a dose of about 3 mg.

6. The method of claim 1, wherein said nadolol is administered in a dose of about 4 mg.

7. The method of claim 1, wherein said nadolol is administered in a dose of about 5 mg.

8. The method of claim 1, wherein the patient has been diagnosed with a neurodegenerative disease.

9. The method of claim 8, wherein is said neurodegenerative disease is one or more selected from the group consisting of MCI (mild cognitive impairment), aMCI (amnestic MCI), Vascular Dementia, Mixed Dementia, FTD (fronto-temporal dementia; Pick's disease), HD (Huntington disease), Rett Syndrome, PSP (progressive supranuclear palsy), CBD (corticobasal degeneration), SCA (spinocerebellar ataxia), MSA (Multiple system atrophy), SDS (Shy-Drager syndrome), olivopontocerebellar atrophy, TBI (traumatic brain injury), CTE (chronic traumatic encephalopathy), stroke, WKS (Wernicke-Korsakoff syndrome; alcoholic dementia & thiamine deficiency), normal pressure hydrocephalus, hypersomnia/narcolepsy, ASD (autistic spectrum disorders), FXS (fragile X syndrome), TSC (tuberous sclerosis complex), prion-related diseases, depressive disorders, DLB (dementia with Lewy bodies), PD (Parkinson's disease), PDD (PD dementia), ADHD (attention deficit hyperactivity disorder), Alzheimer's disease (AD), early AD, and Down Syndrome (DS).

10. A method comprising: treating a subject identified as having diminished cognitive function and/or being in need of or desiring improvement of cognitive function and/or treatment of a neurodegenerative disease by administering to the subject clenbuterol and nadolol, wherein clenbuterol is administered in a dose of about 30 μg to 160 μg and nadolol is administered in a dose of about 0.1 mg to 10 mg.

11. The method of claim 10, wherein said nadolol is administered in a dose of 1 mg to 10 mg.

12. The method of claim 10, wherein said nadolol is administered in a dose of 1 mg to 10 mg and said clenbuterol is administered in a dose of 30 to 160 μg.

13. The method of claim 10, wherein said subject is identified as being in need of treatment of a neurodegenerative disease that is one or more selected from the group consisting of MCI (mild cognitive impairment), aMCI (amnestic MCI), Vascular Dementia, Mixed Dementia, FTD (fronto-temporal dementia; Pick's disease), HD (Huntington disease), Rett Syndrome, PSP (progressive supranuclear palsy), CBD (corticobasal degeneration), SCA (spinocerebellar ataxia), MSA (Multiple system atrophy), SDS (Shy-Drager syndrome), olivopontocerebellar atrophy, TBI (traumatic brain injury), CTE (chronic traumatic encephalopathy), stroke, WKS (Wernicke-Korsakoff syndrome; alcoholic dementia & thiamine deficiency), normal pressure hydrocephalus, hypersomnia/narcolepsy, ASD (autistic spectrum disorders), FXS (fragile X syndrome), TSC (tuberous sclerosis complex), prion-related diseases, depressive disorders, DLB (dementia with Lewy bodies), PD (Parkinson's disease), PDD (PD dementia), ADHD (attention deficit hyperactivity disorder), Alzheimer's disease (AD), early AD, and Down Syndrome (DS).

14. The method of claim 9, wherein the prion-related disease is Creutzfeldt-Jakob Disease (CJD).

15. The method of claim 13, wherein the prion-related disease is Creutzfeldt-Jakob Disease (CJD).

16. The method of claim 1, wherein said clenbuterol is administered at about 80 μg and nadolol is administered at 1 mg.

17. The method of claim 1, wherein said clenbuterol is administered at about 40 μg and nadolol is administered at 0.5 mg.

18. A method comprising:

administering clenbuterol and nadolol to a human patient, wherein said clenbuterol is administered in a dose of about 160 μg, and nadolol is administered in a dose of about 2 mg.

19. The method of claim 10, wherein said clenbuterol is administered in a dose of about 160 μg and nadolol is administered in a dose of about 2 mg.

20. The method of claim 10, wherein said clenbuterol is administered in a dose of about 80 μg and nadolol is administered in a dose of about 1 mg.

21. The method of claim 10, wherein said clenbuterol is administered in a dose of about 40 μg and nadolol is administered in a dose of about 0.5 mg.

22. The method of claim 1, 10 or 18, wherein the clenbuterol and the nadolol are administered as daily doses.

23. A method comprising:

administering clenbuterol and nadolol to a human patient, wherein clenbuterol is administered in a dose of about 40 μg to 80 μg or about 80 μg to 160 μg, and nadolol is administered in a dose of about 0.1 mg to 10 mg.

* * * * *